United States Patent
Iacono et al.

(10) Patent No.: US 12,162,829 B2
(45) Date of Patent: Dec. 10, 2024

(54) GAS PHASE PROCESS FOR ACRYLATE PRODUCTION FROM ETHYLENE AND CARBON DIOXIDE

(71) Applicant: CHEVRON PHILLIPS CHEMICAL COMPANY LP, The Woodlands, TX (US)

(72) Inventors: Pasquale Iacono, Bartlesville, OK (US); Jamie N. Sutherland, Kingwood, TX (US); Carlton E. Ash, Owasso, OK (US); Anand Ramanathan, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 350 days.

(21) Appl. No.: 17/553,165

(22) Filed: Dec. 16, 2021

(65) Prior Publication Data

US 2023/0192586 A1  Jun. 22, 2023

(51) Int. Cl.
*C07C 51/15* (2006.01)

(52) U.S. Cl.
CPC .......... *C07C 51/15* (2013.01); *C07C 2521/00* (2013.01); *C07C 2523/00* (2013.01)

(58) Field of Classification Search
None
See application file for complete search history.

(56) References Cited

U.S. PATENT DOCUMENTS

| | | | |
|---|---|---|---|
| 6,107,230 A | 8/2000 | McDaniel | |
| 6,165,929 A | 12/2000 | McDaniel | |
| 6,294,494 B1 | 9/2001 | McDaniel | |
| 6,300,271 B1 | 10/2001 | McDaniel | |
| 6,316,553 B1 | 11/2001 | McDaniel | |
| 6,355,594 B1 | 3/2002 | McDaniel | |

(Continued)

FOREIGN PATENT DOCUMENTS

| | | |
|---|---|---|
| CN | 103785470 A | 5/2014 |
| JP | 2017144397 A | 8/2017 |

(Continued)

OTHER PUBLICATIONS

Bruckmeier, et.al., Organometallics, Aug. 19, 2010, vol. 29, 2199-2202. DOI: 10.1021/om100060y.

(Continued)

*Primary Examiner* — Sudhakar Katakam
*Assistant Examiner* — Jennifer C Sawyer
(74) *Attorney, Agent, or Firm* — Eversheds Sutherland (US) LLP

(57) ABSTRACT

Catalysts and catalytic processes for the synthesis of acrylic acid and other α,β-unsaturated carboxylic acids and their salts, which are carried out in a diluent or in the absence of a diluent. In an aspect, ethylene and $CO_2$ can be contacted with a Group 8-11 transition metal precursor compound or a Group 8-11 transition metal metalalactone compound in the presence of a metal-treated chemically-modified solid oxide (MT-CMSO) or a metal-treated solid oxide (MT-SO), to form a metal acrylate. As the catalytic activity wanes in either the presence or absence of a diluent, pressure cycling—that is, pressurizing the reaction system with $CO_2$ and an olefin such as ethylene for a time period, releasing the pressure, then re-pressurizing with $CO_2$ and ethylene—can rejuvenate the catalyst and restore its declining catalytic activity.

30 Claims, 1 Drawing Sheet

(56) References Cited

U.S. PATENT DOCUMENTS

| | | |
|---|---|---|
| 6,376,415 B1 | 4/2002 | McDaniel |
| 6,391,816 B1 | 5/2002 | McDaniel |
| 6,395,666 B1 | 5/2002 | McDaniel |
| 6,524,987 B1 | 2/2003 | Collins |
| 6,548,441 B1 | 4/2003 | McDaniel |
| 6,750,302 B1 | 6/2004 | McDaniel |
| 6,831,141 B2 | 12/2004 | McDaniel |
| 6,936,667 B2 | 8/2005 | Jensen |
| 6,992,032 B2 | 1/2006 | McDaniel |
| 7,026,494 B1 | 4/2006 | Yang |
| 7,041,617 B2 | 5/2006 | Jensen |
| 7,148,298 B2 | 12/2006 | Jensen |
| 7,199,073 B2 | 4/2007 | Martin |
| 7,226,886 B2 | 6/2007 | Jayaratne |
| 7,250,510 B2 | 7/2007 | Organ |
| 7,294,599 B2 | 11/2007 | Jensen |
| 7,312,283 B2 | 12/2007 | Martin |
| 7,470,758 B2 | 12/2008 | Jensen |
| 7,501,372 B2 | 3/2009 | Thorn |
| 7,517,939 B2 | 4/2009 | Yang |
| 7,576,163 B2 | 8/2009 | Yang |
| 7,601,665 B2 | 10/2009 | McDaniel |
| 7,619,047 B2 | 11/2009 | Yang |
| 7,629,284 B2 | 12/2009 | Jensen |
| 7,884,163 B2 | 2/2011 | McDaniel |
| 8,642,803 B2 | 2/2014 | Limbach |
| 8,697,909 B2 | 4/2014 | Limbach |
| 8,703,886 B1 | 4/2014 | Yang |
| 9,023,959 B2 | 5/2015 | McDaniel |
| 9,416,087 B2 | 8/2016 | Hlavinka |
| 9,725,393 B2 | 8/2017 | Hlavinka |
| 9,758,461 B2 | 9/2017 | Limbach |
| 9,783,478 B2 | 10/2017 | Hlavinka |
| 9,896,405 B2 | 2/2018 | Hlavinka |
| 10,011,551 B2 | 7/2018 | Limbach |
| 10,160,711 B2 | 12/2018 | Iacono |
| 10,392,336 B2 | 8/2019 | Iacono |
| 10,544,080 B2 | 1/2020 | Hlavinka |
| 10,550,061 B2 | 2/2020 | Iacono |
| 10,584,088 B2 | 3/2020 | Hlavinka |
| 2016/0130208 A1 | 5/2016 | Schäffner |
| 2017/0217869 A1 | 8/2017 | Limbach |
| 2018/0362435 A1 | 12/2018 | Iacono |
| 2018/0362436 A1 | 12/2018 | Hlavinka |
| 2019/0062250 A1 | 2/2019 | Hlavinka |
| 2019/0112251 A1 | 4/2019 | Schaub |
| 2020/0115309 A1 | 4/2020 | Iacono |
| 2020/0123091 A1 | 4/2020 | Hlavinka |

FOREIGN PATENT DOCUMENTS

| | | |
|---|---|---|
| JP | 2021046370 A | 3/2021 |
| WO | 2011107559 A2 | 9/2011 |
| WO | 2015173295 A1 | 11/2015 |
| WO | 2015173296 A1 | 11/2015 |
| WO | 2015173307 A1 | 11/2015 |
| WO | 2016180775 A1 | 11/2016 |

OTHER PUBLICATIONS

Fischer, et.al.,Chem. Commun., 2006, 2510-2512. DOI:10.1039/B603540J.

Graham, et.al., "Production of Acrylic Acid through Nickel-Mediated Coupling of Ethylene and Carbon Dioxide—A DFT Study" Organometallics 2007, 26, 27, 6784-6792. DOI: 10.1021/om700592w.

Hendricksen, "Catalytic Formation of Acrylate from Carbon Dioxide and Ethene," Chemistry, A European Journal, 2014, vol. 20, pp. 12037-12040.

Hoberg, et al., Journal of Organometallic Chemistry, 251 (1983) C51-C53. DOI:10.1016/S0022-328X(00)98789-8.

Hopkins, "Synthesis and Reactivity of 1,2-Bis(di-iso-propylphosphino)benzene Nickel Complexes: A Study of Catalytic CO2-Ethylene Coupling", Organometallics 2018, 37, 3573-3580.

Huguet et al., "Nickel-Catalyzed Direct Carboxylation of Olefins with CO2: One-Pot Synthesis of α, β-Unsaturated Carboxylic Acid Salts", Chem. Eur. J., 2014, vol. 20, pp. 16858-16862.

Jin, et.al. Chem. Eur. J., (2014), 20: 3205-3211. https://doi.org/10.1002/chem.201304196.

Jin, et.al., Organometallics, 2013, 32 (7), 2152-2159. DOI: 10.1021/om400025h.

Langer, et.al., Journal of Organometallic Chemistry, 689, Sep. 22, 2004, pp. 2952-2962. doi:10.1016/j.organchem.2004.04.047.

Lejkowski, et.al., Chem. Eur. J., 2012, 18, 14017-14025. https://doi.org/10.1002/chem.201201757.

Pápai, et;al., Organometallics, Sep. 21, 2004, 23, 22, 5252-5259. DOI:10.1021/om049496+.

Plessow et al., "Acrylate Formation from CO2 and Ethylene Mediated by Nickel Complexes: A Theoretical Study", Organometallics, 2014, vol. 33, pp. 3657-3668.

Uttley, "Ancillary Ligand and Base Influences on Nickel-Catalyzed Coupling of CO2 and Ethylene to Acrylate", Organometallics 2020, 39, 1573-1579.

International Search Report and Written Opinion issued in corresponding application No. PCT/US2022/081687 dated Apr. 20, 2023, 10 pages.

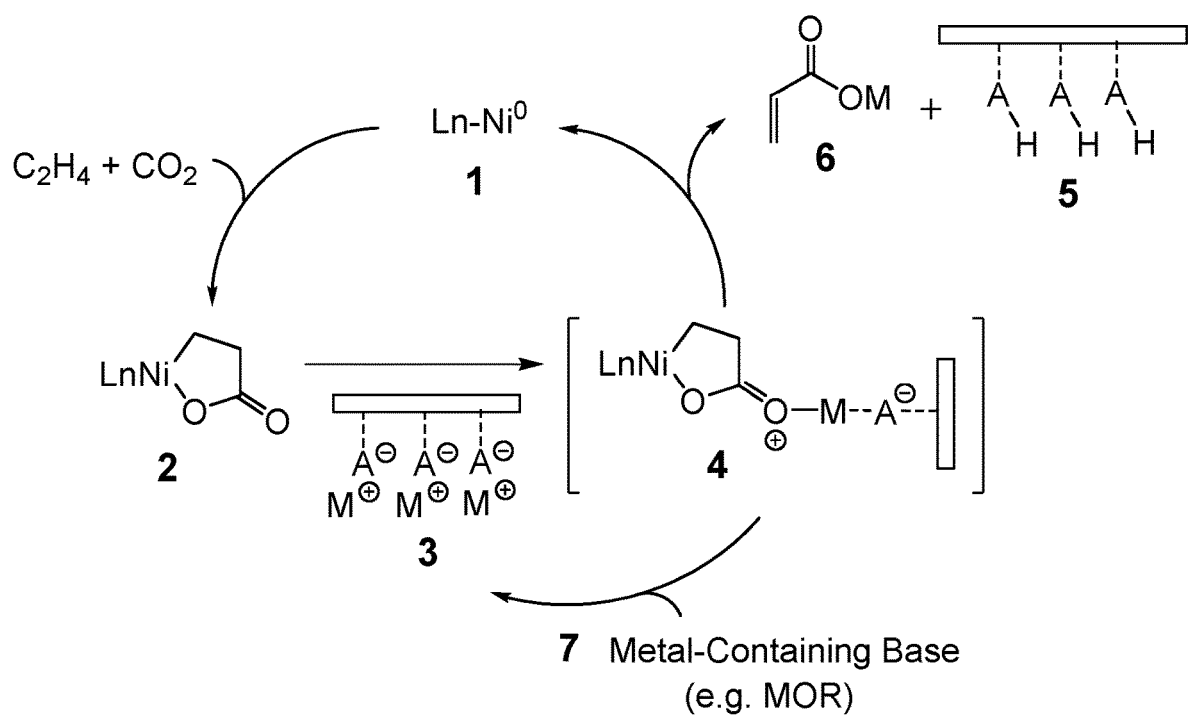

GAS PHASE PROCESS FOR ACRYLATE PRODUCTION FROM ETHYLENE AND CARBON DIOXIDE

CROSS REFERENCE TO RELATED APPLICATION(S)

None.

TECHNICAL FIELD

This disclosure relates to routes for the synthesis of acrylic acid, other α,β-unsaturated carboxylic acids and salts thereof, including catalytic methods.

BACKGROUND

The majority of industrially synthesized chemical compounds are prepared from a limited set of precursors, whose ultimate sources are primarily fossil fuels. As these reserves diminish, it would be beneficial to use a renewable resource, such as carbon dioxide, which is a non-toxic, abundant, and economical $C_1$ synthetic unit. The coupling of carbon dioxide with other unsaturated molecules holds tremendous promise for the direct preparation of molecules currently prepared by traditional methods not involving $CO_2$.

One could envision the direct preparation of acrylates and carboxylic acids through this method when carbon dioxide is coupled with olefins. Currently, acrylic acid is produced commercially by a two-stage oxidation of propylene. The production of acrylic acid directly from carbon dioxide and ethylene would represent a significant improvement due to the greater availability of ethylene and carbon dioxide versus propylene, the use of a renewable material ($CO_2$) in the synthesis, and the replacement of the two-step oxygenation process currently being practiced.

Therefore, what is needed are improved methods for preparing acrylic acid and other α,β-unsaturated carboxylic acids, including catalytic methods.

SUMMARY

This summary is provided to introduce various concepts in a simplified form that are further described below in the detailed description. This summary is not intended to identify required or essential features of the claimed subject matter nor is the summary intended to limit the scope of the claimed subject matter.

This disclosure provides catalyst compositions, processes for preparing the catalyst compositions, and processes for using the catalyst compositions to produce or form an α,β-unsaturated carboxylic acid or a salt thereof including processes in a diluent or in the absence of a diluent. This disclosure also provides catalyst systems which can produce the α,β-unsaturated carboxylic acid or a salt thereof, which include a Group 8-11 transition metal precursor compound or a Group 8-11 transition metal metalalactone compound and an activator. In one aspect, the activator can be a metal-treated chemically-modified solid oxide (MT-CMSO), formed when a chemically-modified solid oxide, comprising a solid oxide which is chemically-modified with an electron-withdrawing anion, is subsequently treated with a metal-containing base or an equivalent thereof, such as a metal salt in combination with a non-metal containing base. For convenience, these materials are termed metal-treated chemically-modified solid oxides, but may also be referred to herein as metal-containing base-treated chemically-modified solid oxides. In another aspect, the activator can be a metal-treated solid oxide (MT-SO), formed when a solid oxide is treated with a metal-containing base or an equivalent thereof such as a metal salt in combination with a non-metal containing base, or treated with a metal-containing salt in the absence of a base. Therefore, in an aspect, it has been found unexpectedly that it is not necessary that the activator solid oxide be chemically-modified with an electron-withdrawing anion prior to treatment with a metal.

When an olefin such as ethylene and carbon dioxide ($CO_2$) are contacted in the presence of the Group 8-11 transition metal or metalalactone precursor compound and the metal-treated chemically-modified solid oxide or a metal-treated solid oxide in a reaction mixture that includes a diluent, under suitable reaction conditions, an α,β-unsaturated carboxylic acid or the salt thereof is formed in which the reaction can be catalytic. The transition metal precursor and any transition metal compound formed in the reaction may be referred to in this disclosure as a catalyst, even when the exact nature of the catalytically-active species is not known and even when the coupling reaction itself may not be catalytic.

In an aspect of this disclosure, it has been determined that during this step of contacting ethylene and $CO_2$ with the catalyst, the Group 8-11 transition metal precursor compound or the Group 8-11 transition metal metalalactone compound can be deposited onto or impregnated into the metal-treated chemically-modified solid oxide (MT-CMSO) or the metal-treated solid oxide (MT-SO) during the process of preparing the catalyst composition. It also has been surprisingly discovered that these supported catalysts are effective at converting ethylene and carbon dioxide to acrylic acid or a salt thereof in the gas phase and in the absence of a diluent, where the reaction involves combining ethylene and carbon dioxide under pressure with the solid catalyst composition. Other unexpected discoveries were made when examining these systems, including the observation that "pressure cycling"—that is, pressurizing with ethylene and $CO_2$ for a time period, releasing the pressure, then re-pressurizing with ethylene and $CO_2$—can rejuvenate the catalyst and restore its declining catalytic activity. Pressure cycling can be carried out many times such that large numbers of turnovers may be realized. Moreover, pressure cycling is effective when the catalytic process is conducted in the presence or absence of a diluent.

Therefore, in an aspect, there is provided a catalyst system of this disclosure, in which the catalyst system can comprise:
  (a) a Group 8-11 transition metal precursor compound comprising at least one first ligand and/or at least one second ligand; and
  (b) (i) a metal-treated chemically-modified solid oxide, wherein the chemically-modified solid oxide comprises at least one solid oxide which has been treated with at least one electron-withdrawing anion or (ii) a metal-treated solid oxide;
  wherein at least a portion of Group 8-11 transition metal precursor compound is deposited on the metal-treated chemically-modified solid oxide or the metal-treated solid oxide.

In another aspect, disclosed herein is a catalyst system, in which the catalyst system can comprise:
  (a) a Group 8-11 transition metal metalalactone compound comprising a metalalactone moiety and at least one ligand in addition to the metalalactone moiety; and
  (b) (i) a metal-treated chemically-modified solid oxide, wherein the chemically-modified solid oxide comprises at least one solid oxide which has been treated with at least one electron-withdrawing anion or (ii) a metal-treated solid oxide;

wherein at least a portion of Group 8-11 transition metal metalalactone compound is deposited on the metal-treated chemically-modified solid oxide or the metal-treated solid oxide.

These catalyst systems can constitute a heterogeneous catalyst composition either in a diluent or in the absence of a diluent. Therefore, these catalyst systems can further comprise a diluent if desired. Alternatively, these catalyst systems can comprise: (a) a solid which is substantially absent a diluent or solvent (as defined herein as comprising less than 10 wt. %, less than 5 wt. %, less than 1 wt. %, or less than 0.5 wt. % diluent or solvent); (b) a free-flowing solid; or (c) both a solid which is substantially absent a diluent or solvent (comprising less than 10 wt. %, less than 5 wt. %, less than 1 wt. %, or less than 0.5 wt. % diluent or solvent) and is a free-flowing solid.

The present disclosure also describes, in other aspects, a process for preparing a catalyst composition, in which the process can comprise contacting in any order:
(i) a Group 8-11 transition metal precursor compound comprising at least one first ligand;
(ii) optionally, at least one second ligand;
(iii) a first olefin;
(iv) carbon dioxide ($CO_2$);
(v) a diluent; and
(vi) [A] a metal-treated chemically-modified solid oxide, wherein the chemically-modified solid oxide comprises at least one solid oxide which has been treated with at least one electron-withdrawing anion or [B] a metal-treated solid oxide, to provide a first reaction mixture;
wherein the contacting is optionally carried out at a total pressure greater than ambient pressure; and
wherein at least a portion of the Group 8-11 transition metal is deposited on the metal-treated chemically-modified solid oxide or the metal-treated solid oxide to provide a catalyst composition.

In this aspect, the process can further comprise the steps of releasing the pressure from the first reaction mixture if applicable, and removing the diluent from the first reaction mixture to provide the catalyst composition as a solid catalyst composition. Also in this aspect, the first reaction mixture can comprise a metalalactone. The first reaction mixture may also comprise an adduct of the metalalactone and the metal-treated chemically-modified solid oxide or the metal-treated solid oxide.

According to another aspect, this disclosure also describes a process for preparing a catalyst composition, in which the process can comprise:
contacting in any order:
(i) a metalalactone compound comprising a Group 8-11 transition metal, a metalalactone moiety, and at least one ligand in addition to the metalalactone moiety; (ii) a first olefin;
(iii) carbon dioxide ($CO_2$);
(iv) a diluent; and
(v) [A] a metal-treated chemically-modified solid oxide, wherein the chemically-modified solid oxide comprises at least one solid oxide which has been treated with at least one electron-withdrawing anion or [B] a metal-treated solid oxide, to provide a first reaction mixture;
wherein the contacting is optionally carried out at a total pressure greater than ambient pressure, and
wherein at least a portion of the Group 8-11 transition metal is deposited on the metal-treated chemically-modified solid oxide or the metal-treated solid oxide to provide a catalyst composition.

In this aspect, the process can further comprise the steps of releasing the pressure from the first reaction mixture if applicable, and removing the diluent from the first reaction mixture to provide the catalyst composition as a solid catalyst composition.

In both these processes for preparing a catalyst composition describe above, first reaction mixture can be pressurized with $CO_2$ to a $CO_2$ partial pressure greater than ambient pressure. In embodiments, the first olefin can be ethylene, in which case the total pressure can be the combined partial pressures of ethylene and $CO_2$. However, the first olefin can comprise or can be independently selected from ethylene, propylene, butene (e.g., 1-butene), pentene, hexene (e.g., 1-hexene), heptene, octene (e.g., 1-octene), or styrene. Where applicable, the first reaction mixture can be pressurized with the first olefin to a total pressure greater than ambient pressure.

In both processes disclosed above for preparing a catalyst composition, any pressure from $CO_2$ and the first olefin can be released from the first reaction mixture, and any diluent can be removed from the first reaction mixture to provide the catalyst composition as a solid catalyst composition. While all the diluent is difficult to remove from the granular solid catalyst composition, by describing the catalyst composition as a solid catalyst it is intended to reflect that the solid catalyst composition (a) can comprise less than 10 wt. %, less than 5 wt. %, less than 1 wt. %, or less than 0.5 wt. % diluent and/or (b) the solid catalyst composition can comprise a free-flowing solid.

In other aspects according to this disclosure, there is provided a process for producing an α,β-unsaturated carboxylic acid or a salt thereof, in which the process can comprise:
(a) contacting in any order (i) a Group 8-11 transition metal precursor compound comprising at least one first ligand, (ii) optionally, at least one second ligand, (iii) a first olefin, (iv) carbon dioxide ($CO_2$), (v) a diluent, and (vi) [A] a metal-treated chemically-modified solid oxide, wherein the chemically-modified solid oxide comprises at least one solid oxide which has been treated with at least one electron-withdrawing anion, or [B] a metal-treated solid oxide, to provide a first reaction mixture,
wherein the contacting is optionally carried out at a total pressure greater than ambient pressure, and
wherein at least a portion of the Group 8-11 transition metal is deposited on the metal-treated chemically-modified solid oxide or the metal-treated solid oxide;
(b) releasing the pressure from the first reaction mixture if applicable, and removing the diluent from the first reaction mixture to provide the catalyst composition as a solid catalyst composition; and
(c) contacting in any order (i) the solid catalyst composition, (ii) a second olefin, and (iii) carbon dioxide ($CO_2$) at a total pressure greater than ambient pressure to provide a second reaction mixture comprising an α,β-unsaturated carboxylic acid or a salt thereof.

In embodiments, the first reaction mixture or the second reaction mixture, independently, can comprise a metalalactone, and in further embodiments, the first reaction mixture or the second reaction mixture, independently, can comprise an adduct of the metalalactone and the metal-treated chemically-modified solid oxide or the metal-treated solid oxide.

In a further aspect, this disclosure provides a process for producing an α,β-unsaturated carboxylic acid or a salt thereof, in which the process can comprise:

(a) contacting in any order (i) a Group 8-11 transition metal metalalactone compound comprising a metalalactone moiety and at least one ligand in addition to the metalalactone moiety, (ii) a first olefin, (iii) carbon dioxide ($CO_2$), (iv) a diluent, and (v) [A] a metal-treated chemically-modified solid oxide, wherein the chemically-modified solid oxide comprises at least one solid oxide which has been treated with at least one electron-withdrawing anion, or [B] a metal-treated solid oxide, to provide a first reaction mixture, wherein the contacting is optionally carried out at a total pressure greater than ambient pressure, and wherein at least a portion of the Group 8-11 transition metal metalalactone compound is deposited on the metal-treated chemically-modified solid oxide or the metal-treated solid oxide;

(b) releasing the pressure from the first reaction mixture if applicable, and removing the diluent from the first reaction mixture to provide the catalyst composition as a solid catalyst composition; and (c) contacting in any order (i) the solid catalyst composition, (ii) the second olefin, and (iii) carbon dioxide ($CO_2$) at a total pressure greater than ambient pressure to provide a second reaction mixture comprising an α,β-unsaturated carboxylic acid or a salt thereof.

In both of these above processes for producing an α,β-unsaturated carboxylic acid or a salt thereof, one starting from the Group 8-11 transition metal precursor compound and one starting from the Group 8-11 transition metal metalalactone compound, it was discovered that a pressure cycling process could be employed to produce additional α,β-unsaturated carboxylic acid or a salt thereof than previously thought possible when no pressure cycling is used. That is, the release and subsequent repressurization of the reaction mixture with $CO_2$ and olefin, when the olefin imparts partial pressure to the system, can be used to rejuvenate the catalyst and produce additional acrylate in this process. For example, in embodiments of both of these above processes for producing an α,β-unsaturated carboxylic acid or a salt thereof, each process can further comprise the steps of:

(d) releasing at least a fraction of the total pressure from the second reaction mixture; and (e) contacting in any order (i) the solid catalyst composition, (ii) the second olefin, and (iii) carbon dioxide ($CO_2$) at a total pressure greater than ambient pressure to provide a subsequent reaction mixture comprising an α,β-unsaturated carboxylic acid or a salt thereof.

Moreover, when steps (d) and (e) are employed, both of these above processes for forming an α,β-unsaturated carboxylic acid or a salt thereof may further comprise the step of:

(f) repeating steps (d) and (e) any number of times, for example from 1 to 30 times, to provide further subsequent reaction mixtures comprising the α,β-unsaturated carboxylic acid or a salt thereof.

In this aspect, steps (d) and (e) can be repeated any number of times, for example, 1, 2, 3, 4, 5, 6, 7, 8, 9, 10, 11, 12, 13, 14, 15, 16, 17, 18, 19, or 20 times. Additional α,β-unsaturated carboxylic acid or a salt thereof, for example, sodium acrylate, can be produced with a number of the additional steps, typically in slowly decreasing amounts, depending upon the reaction conditions.

This disclosure further provides, in another aspect, a process for forming an α,β-unsaturated carboxylic acid or a salt thereof, which utilizes a pressure cycling strategy in the presence of a diluent, as follows. In this aspect, the process can comprise:

(a) contacting in any order (i) a Group 8-11 transition metal precursor compound comprising at least one first ligand, (ii) optionally, at least one second ligand, (iii) a first olefin, (iv) carbon dioxide ($CO_2$), (v) a diluent, and (vi) [A] a metal-treated chemically-modified solid oxide, wherein the chemically-modified solid oxide comprises at least one solid oxide which has been treated with at least one electron-withdrawing anion, or [B] a metal-treated solid oxide, to provide a first reaction mixture;

(b) pressurizing the first reaction mixture with carbon dioxide ($CO_2$) and, if applicable, the first olefin to a total pressure greater than ambient pressure to produce an α,β-unsaturated carboxylic acid or a salt thereof;

(c) releasing at least a fraction of the total pressure from the first reaction mixture to provide a second reaction mixture; and (d) repressurizing the second reaction mixture with carbon dioxide ($CO_2$) and, if applicable, the first olefin to a total pressure greater than ambient pressure to produce additional α,β-unsaturated carboxylic acid or a salt thereof.

Also regarding the process for forming an α,β-unsaturated carboxylic acid or a salt thereof utilizing the pressure cycling strategy in the presence of a diluent, the process can comprise:

(a) contacting in any order (i) a Group 8-11 transition metal metalalactone compound comprising a metalalactone moiety and at least one ligand in addition to the metalalactone moiety, (ii) a first olefin, (iii) carbon dioxide ($CO_2$), (iv) a diluent, and (v) [A] a metal-treated chemically-modified solid oxide, wherein the chemically-modified solid oxide comprises at least one solid oxide which has been treated with at least one electron-withdrawing anion, or [B] a metal-treated solid oxide to provide a first reaction mixture;

(b) pressurizing the first reaction mixture with carbon dioxide ($CO_2$) and, if applicable, the first olefin to a total pressure greater than ambient pressure to produce an α,β-unsaturated carboxylic acid or a salt thereof;

(c) releasing at least a fraction of the total pressure from the first reaction mixture to provide a second reaction mixture; and (d) repressurizing the second reaction mixture with carbon dioxide ($CO_2$) and, if applicable, the first olefin to a total pressure greater than ambient pressure to produce additional α,β-unsaturated carboxylic acid or a salt thereof.

In both of the above processes for forming an α,β-unsaturated carboxylic acid or a salt thereof utilizing the pressure cycling strategy in the presence of a diluent, the processes can independently further comprise the steps of:

(e) releasing at least a fraction of the total pressure from the second reaction mixture to provide a subsequent reaction mixture; and (f) repressurizing the subsequent reaction mixture with carbon dioxide ($CO_2$) and, if applicable, the first olefin to a total pressure greater than ambient pressure to produce additional α,β-unsaturated carboxylic acid or a salt thereof.

Moreover, each process can further independently comprise the step of:

(g) repeating steps (e) and (f) any number of times, for example from 1 to 30 times, to provide further subsequent reaction mixtures and to produce the α,β-unsaturated carboxylic acid or a salt thereof.

Further aspects of this disclosure that are described herein include providing a catalyst system for producing an α,β-unsaturated carboxylic acid or a salt thereof, in which the catalyst system can comprising the contact product of, or the catalyst system prepared by contacting, the various components disclosed hereinabove. For example, there is provided a catalyst system which can comprise the contact product of, or the catalyst system prepared by contacting:
  (i) a Group 8-11 transition metal precursor compound comprising at least one first ligand;
  (ii) optionally, at least one second ligand;
  (iii) a first olefin such as ethylene;
  (iv) carbon dioxide ($CO_2$);
  (v) a diluent; and
  (vi) [A] a metal-treated chemically-modified solid oxide, wherein the chemically-modified solid oxide comprises at least one solid oxide which has been treated with at least one electron-withdrawing anion or [B] a metal-treated solid oxide.

Similarly, there is provided a catalyst system for producing an α,β-unsaturated carboxylic acid or a salt thereof, the catalyst system comprising the contact product of, or the catalyst system prepared by contacting:
  (i) a Group 8-11 transition metal metalalactone compound comprising a metalalactone moiety and at least one ligand in addition to the metalalactone moiety; (ii) optionally, a first olefin such as ethylene;
  (iii) optionally, carbon dioxide ($CO_2$);
  (iv) a diluent; and
  (v) [A] a metal-treated chemically-modified solid oxide, wherein the chemically-modified solid oxide comprises at least one solid oxide which has been treated with at least one electron-withdrawing anion, or [B] a metal-treated solid oxide;
In this aspect, the catalyst system can further comprise the first olefin such as ethylene and can further comprise the $CO_2$ to form the catalyst system.

This summary and the following detailed description provide examples and are explanatory only of the invention. Accordingly, the foregoing summary and the following detailed description should not be considered to be restrictive. Additional features or variations thereof can be provided in addition to those set forth herein, such as for example, various feature combinations and sub-combinations of these described in the detailed description.

BRIEF DESCRIPTION OF THE DRAWINGS

FIG. 1 illustrates one aspect of this disclosure, showing the use of an activator such as a metal-treated chemically-modified solid oxide (MT-CMSO) or a metal-treated solid oxide (MT-SO) in combination with a nickel catalyst which can effect the coupling of ethylene and $CO_2$ to provide a metal acrylate. The reaction is catalytic in nickel and stoichiometric in ethylene, $CO_2$, and the metal-containing base used to form the MT-CMSO or MT-SO. The structures illustrated in this FIGURE are nominal or idealized structures, which are formalized to reflect general stoichiometries and may not suggest actual structural features. Examples of a MT-CMSO include a sodium alkoxide-treated chemically-modified solid oxide (CMSO), in which the CMSO comprises a sulfur oxoacid anion-modified solid oxide, a phosphorus oxoacid anion-modified solid oxide, or a halide ion-modified solid oxide. Examples of a MT-SO include but are not limited to Na—Y zeolite and potassium L-zeolite.

DEFINITIONS

To define more clearly the terms used herein, the following definitions are applicable to this disclosure unless otherwise indicated. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein or render indefinite or non-enabled any claim to which that definition is applied. To the extent that any definition or usage provided by any document incorporated by reference conflicts with the definition or usage provided herein, the definition or usage provided herein controls.

Groups of elements of the periodic table may be indicated using the numbering scheme set out in the version of the periodic table of elements published in *Chemical and Engineering News*, 63(5), 27, 1985. In some instances, a group of elements may be indicated using a common name assigned to the group; for example, alkali metals for Group 1 elements, alkaline earth metals for Group 2 elements, transition metals for Group 3-12 elements, and halogens or halides for Group 17 elements.

Regarding claim transitional terms or phrases, the transitional term "comprising", which is synonymous with "including," "containing," "with", "having", or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Unless specified to the contrary, describing a compound or composition "consisting essentially of" is not to be construed as "comprising," but is intended to describe the recited component that includes materials which do not significantly alter composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of, apply only to feature class to which is utilized and it is possible to have different transitional terms or phrases utilized with different features within a claim. For example, a method can comprise several recited steps (and other non-recited steps) but utilize a catalyst composition preparation consisting of specific steps but utilize a catalyst composition comprising recited components and other non-recited components. While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "an organoaluminum compound" is meant to encompass one organoaluminum compound, or mixtures or combinations of more than one organoaluminum compound unless otherwise specified.

The terms "configured for use" or "adapted for use" and similar language is used herein to reflect that the particular recited structure or procedure is used in an olefin polymerization system or process. For example, unless otherwise specified, a particular structure "configured for use" means it is "configured for use in an olefin polymerization reactor system" and therefore is designed, shaped, arranged, constructed, and/or tailored to effect an olefin polymerization, as would have been understood by the skilled person.

For any particular compound disclosed herein, a general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethyl-propane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

Various numerical ranges are disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. For example, by disclosing a temperature of from 70° C. to 80° C., Applicant's intent is to recite individually 70° C., 71° C., 72° C., 73° C., 74° C., 75° C., 76° C., 77° C., 78° C., 79° C., and 80° C., including any sub-ranges and combinations of sub-ranges encompassed therein, and these methods of describing such ranges are interchangeable. Moreover, all numerical end points of ranges disclosed herein are approximate, unless excluded by proviso. As a representative example, if Applicant states that one or more steps in the processes disclosed herein can be conducted at a temperature in a range from 10° C. to 75° C., this range should be interpreted as encompassing temperatures in a range from "about" 10° C. to "about" 75° C.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In another aspect, use of the term "about" means±15% of the stated value, ±10% of the stated value, 5% of the stated value, or ±3% of the stated value.

Applicant reserves the right to proviso out or exclude any individual members of any such group of values or ranges, including any sub-ranges or combinations of sub-ranges within the group, that can be claimed according to a range or in any similar manner, if for any reason Applicant chooses to claim less than the full measure of the disclosure, for example, to account for a reference that Applicant may be unaware of at the time of the filing of the application. Further, Applicant reserves the right to proviso out or exclude any individual substituents, analogs, compounds, ligands, structures, or groups thereof, or any members of a claimed group, if for any reason Applicant chooses to claim less than the full measure of the disclosure, for example, to account for a reference or prior disclosure that Applicants may be unaware of at the time of the filing of the application.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. Unless otherwise specified, "substituted" is intended to be non-limiting and include inorganic substituents or organic substituents as understood by one of ordinary skill in the art.

A chemical "group" may be described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. For example, an "alkyl group" formally can be derived by removing one hydrogen atom from an alkane, while an "alkanediyl group" (also referred to as a "alkylene group") formally can be derived by removing two hydrogen atoms from an alkane. Moreover, a more general term can be used to encompass a variety of groups that formally are derived by removing any number ("one or more") of hydrogen atoms from a parent compound, which in this example can be described as an "alkane group," which encompasses an "alkyl group," an "alkanediyl group," and materials have three or more hydrogen atoms, as necessary for the situation, removed from the alkane. The disclosure that a substituent, ligand, or other chemical moiety can constitute a particular "group" implies that the known rules of chemical structure and bonding are followed when that group is employed as described. When describing a group as being "derived by," "derived from," "formed by," or "formed from," such terms are used in a formal sense and are not intended to reflect any specific synthetic method or procedure, unless specified otherwise or the context requires otherwise.

Groups may be specified according to the atom that is bonded to the metal or bonded to another chemical moiety as a substituent, such as an "oxygen-bonded group," which is also called an "oxygen group." For example, an oxygen-bonded group includes species such as hydrocarbyloxide (—OR where R is a hydrocarbyl group, also termed hydrocarboxy), alkoxide (—OR where R is an alkyl group), aryloxide (—OAr where Ar is an aryl group), or substituted analogs thereof, which function as ligands or substituents in the specified location. Therefore, an alkoxide group and an aryloxide group are each a subgenus of a hydrocarbyloxide (hydrocarbyloxy) group.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified or unless the context requires otherwise, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. In an aspect, the context could require other ranges or limitations, for example, when the subject carbon-containing group is an aryl group or an alkenyl group, the lower limit of carbons in these subject groups is six carbon atoms and two carbon atoms, respectively. Moreover, other identifiers or qualifying terms may be utilized to indicate the presence or absence of a particular substituent, a particular regiochemistry and/or stereochemistry, or the presence of absence of a branched underlying structure or backbone, and the like.

The term "olefin" is used herein in accordance with the definition specified by IUPAC: acyclic and cyclic hydrocarbons having one or more carbon-carbon double bonds apart from the formal ones in aromatic compounds. The class "olefins" subsumes alkenes and cycloalkenes and the corresponding polyenes. Ethylene, propylene, 1-butene, 2-butene, 1-hexene and the like are non-limiting examples of olefins. The term "alpha olefin" as used in this specification and claims refers to an olefin that has a double bond between the first and second carbon atom of the longest contiguous chain of carbon atoms. The term "alpha olefin" includes linear and branched alpha olefins unless expressly stated otherwise.

A "halide", also referred to as a "halo" group or a halogen substituent or group has its usual meaning. Examples of halides include fluoride, chloride, bromide, and iodide.

The term "co-catalyst" is used generally herein to refer to any additional compounds or components that are used in addition to the carbon dioxide, olefin, and the Group 8-11 transition metal compounds or Group 8-11 transition metal metalalactone compounds used in the catalytic reactions, which may constitute a component of a catalyst composition or a catalyst system. For example in one aspect, the term co-catalyst may refer to an activator-support such as the metal-treated chemically-modified solid oxide described herein. In a further aspect, the term co-catalyst may refer to an activator-support such as the metal-treated solid oxide described herein. The term "co-catalyst" is used regardless of the actual function of the compound or material or any chemical mechanism by which the compound or material may operate in the process.

The terms "chemically-modified solid oxide" (CMSO), "chemically-treated solid oxide" (CTSO), "solid oxide treated with an electron-withdrawing anion", "treated solid oxide", "treated solid oxide compound," and the like, are used herein to indicate a solid, inorganic oxide of relatively high porosity, which can exhibit Lewis acidic or Brønsted acidic behavior, and which has been treated with an electron-withdrawing component such as an electron-withdrawing anion or anion source, and which is then calcined prior to use. These materials are also termed "solid super acid" or "SSA" because of the high acidity and solid form. Thus, the "SSA" or "CMSO" can be prepared from a solid oxide such as alumina, silica, silica-alumina, silica-coated alumina, or aluminosilicates (i.e. zeolites) which has been chemically treated or modified with an electron-withdrawing anion such as sulfate, phosphate fluoride, or chloride. The specific SSA abbreviated S-SSA is sulfated alumina, and the specific SSA abbreviated M-SSA is fluorided silica-coated alumina. This catalyst component also may be referred to as simply the "activator-support", as it comprises, consists of, consists essentially or, or is selected from a solid oxide treated with an electron-withdrawing anion. The terms "support" and "activator-support" are not used to imply that these components are inert, and such components should not be construed as an inert component of the catalyst composition.

As used for the catalytic methods of this disclosure, the "chemically-modified solid oxides" (CMSO) or "solid super acids" (SSA) of this disclosure are further treated with a metal-containing base or an equivalent thereof such as a metal salt in combination with a non-metal containing base, to form what is termed the "metal-treated chemically-modified solid oxides" (MT-CMSO) materials as described herein. In an aspect, a metal-containing base is conveniently used for the preparation of the MT-CMSO materials, for example, sodium tert-butoxide (NaO-t-Bu) or potassium tert-butoxide (KO-t-Bu). Therefore, in this disclosure, the "metal-treated chemically-modified solid oxides" may also be referred to as "metal-containing base-treated chemically-modified solid oxides", and these descriptions are used interchangeably regardless of whether the MT-CMSO is prepared using a metal-containing base or an equivalent thereof such as a metal salt in combination with a non-metal containing base. While not intending to be bound by theory, the description of these activators as a metal-treated chemically-modified solid oxides highlights an activation process which is believed to involve the metal in combination with the chemically-modified solid oxide. Terms such as "metal-treated chemically-modified solid oxides", "metal-containing base-treated chemically-modified solid oxides", "metal-treated solid super acids", or "metal-containing base-treated solid super acids" are used interchangeably. The examples highlight the use of sodium (containing base)-treated chemically-modified solid oxides. Representative preparations of some of the metal-treated chemically-modified solid oxides are disclosed in U.S. Pat. No. 9,725,393, which is incorporated herein in its entirety.

Also as used for the catalytic methods of this disclosure, the "metal-treated solid oxides" (MT-SO) which can be used as activators according to this disclosure can comprise solid oxide materials which are treated or contacted with, for example, (a) a metal-containing base, (b) a metal-containing salt in combination with a non-metal containing base, or (c) a metal-containing salt. Such materials may be referred to as metal-containing base-treated solid oxides, metal-containing salt-treated solids oxides, or metal-salt treated solid oxides, and these terms are used interchangeably. In an aspect, a metal-containing base such as sodium tert-butoxide (NaO-t-Bu) or a metal salt such as sodium nitrate ($NaNO_3$) can be used in preparing the "metal-treated solid oxides" (MT-SO). Again, while not intending to be bound by theory, the description of these activators as simply metal-treated solid oxides highlights an activation process which is believed to involve the metal in combination with the solid oxide.

The terms "catalyst composition," "catalyst mixture," "catalyst system," and the like, do not depend upon the actual product or composition resulting from the contact or reaction of the initial components of the claimed catalyst composition/mixture/system, the nature of the active catalytic site, or the fate of the co-catalyst, the metallocene compound(s), any olefin monomer used to prepare a pre-contacted mixture, or the activator (e.g., activator-support), after combining these components. The use of these terms also does not require that the particular combination of components exhibit catalytic activity in the presence of an α-olefin and $CO_2$. Therefore, the terms "catalyst composition," "catalyst mixture," "catalyst system," and the like, encompass some or all of the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, are used interchangeably throughout this disclosure.

The term "catalyst" may also be used interchangeably with the terms catalyst composition, catalyst mixture, or catalyst system, or the term "catalyst" may be used to refer to the Group 8-11 transition metal precursor compound or the Group 8-11 transition metal metalalactone compound, as the context allows or requires. As with the catalyst composition, the use of the term "catalyst" also does not require that the particular Group 8-11 transition metal precursor compound or the Group 8-11 transition metal metalalactone compound exhibit catalytic activity in the presence of an $\alpha$-olefin and $CO_2$, nor does it not depend upon the actual product or composition resulting from the contact or reaction of the Group 8-11 transition metal precursor compound or the Group 8-11 transition metal metalalactone compound with any other components of the catalyst composition/mixture/system.

The terms "contact product", "contacting", and the like, are used herein to describe compositions and methods wherein the components are combined together in any order, in any manner, and for any length of time, unless specified otherwise. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, use of the term "contact product" does not require that the respective components react with one another. Similarly, the term "contacting" is used herein to refer to materials which can be combined by blending, mixing, slurrying, suspending, dissolving, reacting, allowing to react, treating, or otherwise contacting in some other manner. Consequently, depending upon the circumstances, a "contact product" also can be a mixture, a reaction mixture, or a reaction product.

The term "precontacted" mixture is used herein to describe a first mixture of catalyst components that are contacted for a first period of time prior to the first mixture being used to form a "postcontacted" or second mixture of catalyst components that are contacted for a second period of time. These terms may be used to describe any of a series of contact products which are adjacent in a contacting sequence. Thus, a second mixture of catalyst components may be a "postcontacted" mixture with respect to a first mixture but a "precontacted" mixture with respect to a third mixture upon contact with another component.

The terms "deposit" and "impregnate" are used interchangeably to describe the association, deposition, and/or impregnation of the Group 8-11 transition metal precursor compound or the Group 8-11 transition metalalactone onto or into the metal-treated chemically-modified solid oxide or the metal-treated solid oxide. These terms are used without intending to reflect any specific mechanism of the deposition or any specific physical structure associated with the deposited transition metal catalyst. Therefore, use of one of these terms in place of another is not intended to reflect that the process only on the outer surface metal-treated chemically-modified solid oxide or the metal-treated solid oxide, nor is it intended to reflect that transition metal catalyst is necessarily put down throughout the inner pore structure of the solid oxide matrix. Deposition or impregnation conditions are examined in detail in this disclosure, and it is believed that a range of physical structures associated with the deposited transition metal catalyst can occur.

When a solid material such as a solid supported catalytic material is described as "substantially absent a diluent", "substantially absent a solvent", "substantially diluent-free", substantially solvent free" and the like, it is intended to reflect that diluent or solvent has been removed from the suspended solid and the solid has been dried. Because some solvents are not readily removed and removal of solvent at elevated temperatures is usually avoided, we can define terms such as "substantially absent a diluent" as meaning: (a) a solid which comprises less than 10 wt. %, less than 5 wt. %, less than 1 wt. %, or less than 0.5 wt. % diluent or solvent; (b) a free-flowing solid; or (c) a solid both comprises less than 10 wt. %, less than 5 wt. %, less than 1 wt. %, or less than 0.5 wt. % diluent or solvent and is a free-flowing solid. That is, some residual solvent is acceptable.

As used herein, the term "sulfur oxoacid anion" in the context of suitable sulfur oxoacid anion sources that can be used to prepare the sulfur oxoacid anion-modified solid oxide, include both substituted including halide-substituted and non-substituted sulfur oxoacid anions. For example, the term "sulfur oxoacid anion" is intended to include but not be limited to, sulfate, bisulfate, fluorosulfate, alkyl sulfonate (for example, mesylate or methanesulfonate), aryl sulfonate (for example, tosylate or toluenesulfonate), fluoroalkyl sulfonate (for example, triflate or trifluoromethanesulfonate), fluoroaryl sulfonate (for example, for example, $[CF_3C_6H_4SO_3]^-$), and thiosulfate, and any combination thereof. For example, the alkyl sulfonate can be a $C_1$-$C_{10}$ alkyl sulfonate, the aryl sulfonate can be a $C_6$-$C_{14}$ aryl sulfonate, the fluoroalkyl sulfonate can be a $C_1$-$C_{10}$ fluoroalkyl sulfonate, and the fluoroaryl sulfonate can be a $C_6$-$C_{14}$ fluoroaryl sulfonate.

Also as used herein, the term "phosphorus oxoacid anion" in the context of suitable phosphorus oxoacid anion sources that can be used to prepare the phosphorus oxoacid anion-modified solid oxide, include both substituted including halide-substituted and non-substituted phosphorus oxoacid anions. For example, the term "phosphorus oxoacid anion" is intended to include but not be limited to, phosphate, monofluorophosphate, difluorophosphate, or similar anions, or any combination thereof. Unless specified otherwise, the term "fluorophosphate" or "fluorophosphates" include both monofluorophosphate ($[PO_3F]^{2-}$) and difluorophosphate ($[PO_2F_2]^-$).

The symbol "~" or "≈" are used herein to mean "about". The abbreviation "ca" or "ca." may also be used herein to mean "about".

The Abstract of this application is not intended to be used to construe the scope of the claims or to limit the scope of the subject matter that is disclosed herein, but rather to satisfy the requirements of 37 C.F.R. § 1.72(b), to enable the United States Patent and Trademark Office and the public generally to determine quickly from a cursory inspection the nature and gist of the technical disclosure. Moreover, any headings that are employed herein are also not intended to be used to construe the scope of the claims or to limit the scope of the subject matter that is disclosed herein. Any use of the past tense to describe any example otherwise indicated as constructive or prophetic is not intended to reflect that the constructive or prophetic example has actually been carried out.

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

DETAILED DESCRIPTION

The present disclosure is directed generally to methods for forming α,β-unsaturated carboxylic acids, or salts thereof. An illustrative example of a suitable α,β-unsaturated carboxylic acid is acrylic acid.

This disclosure provides catalyst systems which may be referred to as catalyst compositions, processes for preparing the catalyst compositions, and processes for using the catalyst compositions to produce or form an α,β-unsaturated carboxylic acid or a salt thereof from an α-olefin such as ethylene and carbon dioxide, including catalytic processes in the presence of a diluent or in the absence of a diluent. The catalyst systems which can produce the α,β-unsaturated carboxylic acid or a salt thereof include a Group 8-11 transition metal precursor compound or a Group 8-11 transition metal metalalactone compound and a metal-treated chemically-modified solid oxide (MT-CMSO) or a metal-treated solid oxide (MT-SO), along with ethylene and $CO_2$. The transition metal precursor or metalalactone compound or any transition metal compound formed in the reaction may be referred to in this disclosure as a catalyst, even when the coupling reaction is not catalytic. While not intending to be bound by theory, it is believed that the Group 8-11 transition metal precursor compound forms an intermediate Group 8-11 transition metal metalalactone compound when contacted with ethylene and $CO_2$, including in the presence of a MT-CMSO or a MT-SO.

In an aspect of this disclosure, it has been discovered that the Group 8-11 transition metal precursor compound or metalalactone compound can be deposited onto or impregnated into the MT-CMSO or MT-SO during the process of contacting these components, such as when preparing the catalyst composition. It has also been discovered that the Group 8-11 transition metal precursor compound or metalalactone compound can be deposited onto or impregnated into the MT-CMSO or MT-SO during the step of contacting an C-olefin such as ethylene and $CO_2$ with the Group 8-11 transition metal precursor compound or metalalactone compound in the presence of the MT-CMSO or MT-SO. Therefore, the present disclosure employs a metal-treated, for example sodium-treated, chemically-modified solid oxide or solid oxide that has not been chemically-modified and a transition metal catalyst or catalyst precursor such as a nickel catalyst, which presumably allows the transition metal catalyst to electrostatically bind to the MT-CMSO or MT-SO surface so that it is not leached into the solvent or supernatant.

Previously, metal-treated chemically-modified solid oxides and nickel catalysts were utilized to produce sodium acrylate in the presence of solvents, which were thought to encourage catalysis to proceed through diluent effects normally presumed for most heterogeneous processes. In previous sodium acrylate formation processes which use soluble or homogenous sources of sodium such as sodium alkoxides or sodium aryloxides, a diluent or solvent is needed. In this disclosure, the beneficial effect of removing the solvent for the process after the nickel (or Group 8-11 transition metal) catalyst has been impregnated into the metal-treated chemically-modified solid oxides (MT-CMSO) was discovered. This beneficial effect was also observed when metal-treated solid oxides (MT-SO) were used as activators. Therefore, these supported catalysts are effective at converting ethylene and carbon dioxide to acrylic acid or a salt thereof in the gas phase and therefore in the absence of a diluent, where the reaction involves combining ethylene and carbon dioxide under pressure with the solid catalyst composition.

Previously, the nickel-catalyzed production of sodium acrylate utilizing a sodium base such as sodium-tert-butoxide has achieved only limited catalytic turnovers, for example, roughly 10 to 20 catalytic turnovers. However, disclosed herein is a "pressure cycling" procedure, that is, pressurizing the supported catalyst with an α-olefin such as ethylene and $CO_2$ for a time period, releasing the pressure, then re-pressurizing with ethylene and $CO_2$, which has been discovered to restore activity to the catalyst such that large numbers of turnovers may be realized. This pressure cycling can be effective when the catalytic process is conducted in the presence or absence of a diluent.

One example of the α,β-unsaturated carboxylic acid salt formation from an exemplary nickel compound and nickel metalalactone and a MT-CMSO or MT-SO is illustrated in FIG. 1, which provides for a nickel catalytic coupling reaction between an olefin and $CO_2$ and formation of an acrylate. The structures illustrated in this FIGURE are nominal or idealized structures, which are formalized to reflect general stoichiometries and may not suggest actual structural features. Examples of a MT-CMSO include a sodium alkoxide-treated chemically-modified solid oxide (CMSO), in which the CMSO comprises a sulfur oxoacid anion-modified solid oxide, a phosphorus oxoacid anion-modified solid oxide, or a halide ion-modified solid oxide. Examples of a MT-SO include but are not limited to Na—Y zeolite and potassium L-zeolite. Thus, FIG. 1 is not limiting but is exemplary, and each reactant, catalyst, CMSO, MT-CMSO, and MT-SO and product are provided for illustrative purposes.

FIG. 1 provides a general framework for the catalytic cycle of this disclosure and is not intended to be limited to any specific reaction mechanism or chemical structure of intermediate. The Ni catalyst can be prepared starting with a Ni(0) complex such as $Ni(COD)_2$ (COD is 1,5-cyclooctadiene), which can be reacted with a bis-phosphine ligand such as bis(dicyclohexyl-phosphino)ethane ligand $(C_6H_{11})_2PCH_2CH_2P(C_6H_{11})_2$ (abbreviated "dcpe") and ethylene to form the $(dcpe)Ni(CH_2=CH_2)$. The catalytic reactions disclosed herein are stoichiometric in ethylene, $CO_2$, and metal-containing base, and catalytic in Group 8-11 metal such as nickel. As FIG. 1 illustrates, the desired pathway involves the formation of metal acrylate, such as sodium acrylate, via reaction of an intermediate nickelalactone complex $(dcpe)Ni(OC(O)CH_2CH_2)$ where the $—OC(O)CH_2CH_2—$ ligand forms a metalacyclic structure with the nickel, with the metal-treated chemically-modified solid oxide (MT-CMSO) or the metal-treated solid oxide (MT-SO). The presence of excess ethylene enables release of free sodium acrylate (the desired product) and reforms the initial Ni(0) catalyst which can react with additional ethylene and $CO_2$ to continue the catalytic cycle.

In FIG. 1, a transition metal catalyst as described herein is illustrated generally by a nickel(0) catalyst at compound 1 (Ln is the general representation of n unspecified ligands L) and the olefin disclosed herein, generally an α-olefin, is illustrated by ethylene. In the presence of the catalyst 1, the olefin couples with $CO_2$ to form the metalalactone 2, which is thought to interact with a metal-treated chemically-modified solid oxide (MT-CMSO) or metal-treated solid oxide (MT-SO) illustrated as 3 in FIG. 1. The MT-CMSO and MT-SO activator-supports are described in detail herein. Examples of MT-CMSO include but are not limited to a metal-treated sulfur oxoacid anion-modified solid oxide (including, for example, fluorosulfate-modified solid oxides), a metal-treated phosphorus oxoacid anion-modified solid oxide (including, for example, fluorophosphate-modified solid oxides), or a metal-treated halide ion-modified solid oxide, illustrated as 3 in FIG. 1. The same solid oxides used to prepare the MT-CMSO can be used to prepare the MT-SO in which the solid oxide has not been chemically-modified with an electron-withdrawing anion, examples of which include sodium-treated silicas, sodium-treated silicates, and sodium-treated aluminosilicates such as sodium-treated zeolites.

As illustrated in FIG. 1, it is thought that the metalalactone 2 also can be destabilized by its interaction with the MT-CMSO or MT-SO activator-support. While not intending to be bound by theory, the MT-CMSO and MT-SO solid activators comprise associated metal cations, which are thought to interact with metalalactone 2 in some fashion, for example to form an adduct of some type, such as one illustrated as intermediate 4. Reaction of the combined MT-CMSO or MT-SO solid activator 3 and metalalactone 2 (or intermediate of some type, represented generally as 4) proceeds to eliminate or release the metal acrylate 6, for example, from adduct 4, and regenerates catalyst compound (or catalyst precursor compound) 1 and byproduct solid oxide material 5, which in an aspect can comprise a chemically-modified solid oxide (CMSO) or solid oxide (SO) comprising oxoacid moieties, but generally fewer cationic metal sites than the MT-CMSO or MT-SO. The CMSO or SO may subsequently be regenerated to the MT-CMSO or MT-SO by treatment with a metal-containing base such as a metal hydroxide or metal alkoxide, or metal alkyl amide, 7. While not intending to be theory-bound, the resulting MT-CMSO or MT-SO are believed to have sufficiently accessible metal sites that are capable of interacting with the metalalactone, for example, as illustrated in FIG. 1.

Under certain conditions such as higher temperatures and excess $CO_2$, it was discovered that the nickelalactone complex (dcpe)Ni(OC(O)CH$_2$CH$_2$) (abbreviated herein as "(dcpe)NiLac" and shown below) may undergo a second $CO_2$ insertion reaction into the nickelalactone nickel-carbon bond followed by rearrangement which results in the formation of a nickel(II) methyl malonate complex (dcpe)Ni (OC(O)CH$_2$CH$_2$C(O)O), where the —OC(O)CH$_2$CH$_2$C(O) O— ligand forms a metalacyclic structure with the nickel. This methyl malonate complex is abbreviated "(dcpe)NiM" and is also illustrated below. This reaction may be viewed as an over-oxidation which can be reduced, minimized, or avoided by selecting reaction conditions within which to operate the catalysis and which improve or maximize atom economy for acrylate formation. While not intending to be bound by theory, it is believed that these results suggest that the overall acrylate formation rate in the liquid phase is constrained by pore diffusion limitations.

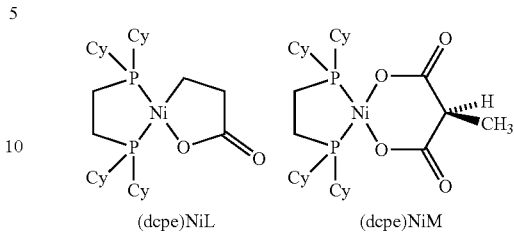

(dcpe)NiL    (dcpe)NiM

FIG. 1 is not intended to reflect a reaction mechanism, and the MT-CMSO and CMSO structures illustrated in FIG. 1 are nominal or idealized structures, which are not intended to and may not reflect actual chemical structures. The participation of the solvent and/or other reaction components in the elimination or release of the metal acrylate 6, is not fully understood but may include direct participation in the reaction or simply solvating an acrylate salt which may be insoluble in the diluent. Other routes of synthesis of acrylic acid, other α,β-unsaturated carboxylic acids and salts thereof are described in U.S. Pat. Nos. 9,416,087; 9,725,393; 9,783,478; and 9,896,405; each of which is incorporated by reference in its entirety.

In one example, it was found that during the catalytic production of sodium acrylate in a diluent that the conversion stopped after about 20 hours ("hr" or "h") at a temperature of about 40° C., for a maximum turnover number (TON) of about 20. However, it was discovered that the catalyst was still active and could be revived by removing all, or a portion, of the ethylene and carbon dioxide pressure from the reactor, and then re-pressurizing the reactor with ethylene and $CO_2$. In some experiments, turnover numbers (TON) of about 80 have been achieved with a total of three pressure swings or "re-pressurizing" sequences over a time period of about 80 hr. While not intending to be bound by a specific mechanism or theory, this cycling of pressure is thought to open restricted pores during the production of the sodium acrylate. Sodium acrylate is thought to solidify on the solid sodium-treated CMSO or sodium-treated SO and may in fact lead to pore plugging in the solid oxide material. Cycling pressures regularly during in the course of the conversion was found to increase the rate and extent of sodium conversion to sodium acrylate.

It was also found during the course of the catalytic sodium acrylate formation reaction that the nickel catalyst moved from being in solution in the organic solvent to being supported on the MT-CMSO. Turnover numbers greater than 100 have been achieved over a 20 h reaction period when solvent was not present or substantially absent as defined here, which represents a considerable increase in catalyst activity relative to corresponding reactions in an organic solvent. Comparable TONs have also been achieved when an external reservoir of premixed ethylene and $CO_2$ feedstock is employed at only 35 psig pressure. These results offer the potential to operate at higher gas pressures, higher reaction temperatures, and to move through gas pressure cycling more easily and rapidly than possible in previous reactions in an organic solvent.

Solid Oxides Used for the Metal-Treated Chemically-Modified Solid Oxides (MT-CMSO) and the Metal-Treated Solid Oxides (MT-SO)

The solid oxides which can be used to prepare the chemically-modified solid oxides (CMSO) and therefore the metal-treated chemically-modified solid oxides (MT-CMSO), may also be used to prepare the metal-treated solid oxides (MT-SO).

Accordingly, this disclosure encompasses processes, catalyst compositions, catalyst systems and the like, wherein the activator or co-catalyst can comprise a solid oxide such as a metal oxide. In an aspect, the activator can comprise a calcined solid oxide. For example, solid oxides can comprise, consist of, consist essentially of, or can be selected from at least one silica, alumina, silica-alumina, silica-coated alumina, silicates, aluminosilicates, zeolites, aluminum phosphate, aluminophosphate, heteropolytungstate, mullite, boehmite, titania, zirconia, magnesia, boria, calcia, zinc oxide, silica-titania, silica-zirconia, silica-magnesia, alumina-titania, alumina-zirconia, zinc-aluminate, alumina-boria, silica-boria, aluminophosphate-silica, magnesium aluminate, titania-zirconia, heteropolytungstate, a mixed oxide thereof, or any combination thereof.

In one aspect, the CMSO, MT-CMSO, and MT-SO materials of this disclosure can comprise a solid inorganic oxide material, a mixed oxide material, a coated oxide material, or a combination of inorganic oxide materials. Thus, the solid oxide of this disclosure encompasses oxide materials such as alumina, "mixed oxide" compounds thereof such as silica-alumina, coated oxide materials such as silica-coated alumina, and combinations and mixtures thereof. The mixed oxide compounds such as silica-alumina can be single or multiple chemical phases with more than one metal combined with oxygen to form a solid oxide compound. Any of the solid oxide materials disclosed herein can be utilized in the CMSO and in the MT-CMSO and MT-SO activator-supports of this disclosure.

Examples of mixed oxides that can be used in the MT-CMSO and MT-SO of this disclosure include, but are not limited to, silica-alumina, silica-titania, silica-zirconia, zeolites, clay minerals, silica-coated alumina, aluminum phosphate, aluminophosphate, heteropolytungstate, mullite, boehmite, alumina-titania, alumina-zirconia, zinc-aluminate and the like; alternatively, examples of mixed oxides that can be used in the activator of the present disclosure include, but are not limited to, silica-alumina, silica-titania, silica-zirconia, alumina-titania, alumina-zirconia, zinc-aluminate and the like; alternatively, examples of mixed oxides that can be used in the activator of the present disclosure include, but are not limited to, silica-alumina, silica-titania, silica-zirconia, alumina-titania, and the like.

In one aspect, the solid oxide can comprise a solid inorganic oxide comprising oxygen and at least one element selected from Group 2, 3, 4, 5, 6, 7, 8, 9, 10, 11, 12, 13, 14, or 15 of the periodic table, or comprising oxygen and at least one element selected from the lanthanide or actinide elements; alternatively, the chemically-modified solid oxide can comprise a solid inorganic oxide comprising oxygen and at least one element selected from Group 4, 5, 6, 12, 13, or 14 of the periodic table, or comprising oxygen and at least one element selected from the lanthanide elements. (See: *Hawley's Condensed Chemical Dictionary*, 11$^{th}$ Ed., John Wiley & Sons; 1995; Cotton, F. A.; Wilkinson, G.; Murillo; C. A.; and Bochmann; M. *Advanced Inorganic Chemistry*, 6$^{th}$ Ed., Wiley-Interscience, 1999.) Usually, the inorganic oxide can comprise oxygen and at least one element selected from Al, B, Be, Bi, Cd, Co, Cr, Cu, Fe, Ga, La, Mn, Mo, Ni, Sb, Si, Sn, Sr, Th, Ti, V, W, P, Y, Zn or Zr; alternatively, the inorganic oxide can comprise oxygen and at least one element selected from Al, B, Si, Ti, P, Zn or Zr.

Suitable examples of solid oxide materials or compounds that can be used in the chemically-modified solid oxide of the present disclosure can comprise, consist of, consist essentially of, or can be selected from $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, $Na_2O$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, $K_2O$, CaO, $La_2O_3$, $Ce_2O_3$, and the like, including mixed oxides thereof (for example, silica-alumina), coated oxides thereof, and combinations thereof.

Alternatively, suitable examples of solid oxide materials or compounds that can be used in the chemically-modified solid oxide of the present disclosure can comprise, consist of, consist essentially of, or can be selected from $Al_2O_3$, $B_2O_3$, $SiO_2$, $SnO_2$, $TiO_2$, $V_2O_5$, $WO_3$, $Y_2O_3$, ZnO, $ZrO_2$, and the like, including mixed oxides thereof, and combinations thereof. Alternatively still, suitable examples of solid oxide materials or compounds that can be used in the chemically-modified solid oxide of the present disclosure include, but are not limited to, $Al_2O_3$, $SiO_2$, $TiO_2$, $ZrO_2$, and the like, including mixed oxides thereof, and combinations thereof.

In a further aspect, the solid oxide of [A] the metal-treated chemically-modified solid oxide or [B] the metal-treated solid oxide can comprise, consist of, consist essentially of, or be selected from a silica, a silicate, or an alumino silicate. In embodiments, the solid oxide can comprise, consist of, consist essentially of, or be selected from a mesoporous silica, a mesostructured cellular foam (MCF) silica, a molecular sieve, a zeolite, or any combination thereof. When these materials are utilized for the metal-treated solid oxide (MT-SO), the metal-treated solid oxide can comprise or can be selected from Na-MCM-41, Na/Al-KIT-6, Na—Y zeolite, Na-SBA-15, Na-treated trimodal porous silica (TMS), potassium L-zeolite, or any combination thereof.

The use of these materials in the CMSO and for the MT-CMSO and MT-SO activator-supports are further described herein.

Chemically-Modified Solid Oxide (CMSO)

The chemically-modified solid oxides (CMSO), also termed chemically-treated solid oxides (CMSOs), of the present disclosure have been described in, for example, U.S. Pat. Nos. 8,703,886, and 9,023,959, which are incorporated herein by reference in their entireties. The CMSO materials described here are used in the formation of the metal-treated CMSO materials that are useful in the acrylate production process of this disclosure. In this disclosure these materials may be referred to as activators, support activators, co-catalysts, and other terms. The solid oxides used in the CMSO, MT-CMSO, and MT-SO can comprise or can be selected from any of the solid oxides disclosed herein.

In an aspect, the activator also can comprise, consist of, consist essentially or, or be selected from a chemically-modified solid oxide or a metal-treated chemically-modified solid oxide. Referencing the definitions section, the term "chemically-modified solid oxide" is used interchangeably with similar terms such as, "solid oxide treated with an electron-withdrawing anion", "treated solid oxide", and the like. While not intending to be bound by theory, it is thought that the chemically-modified solid oxide can serve as an acidic activator-support which allows it to function as the activator in the process disclosed herein.

In one aspect of this disclosure, the activator can comprise at least one chemically-modified solid oxide comprising at least one solid oxide treated with at least one electron-withdrawing anion, wherein the solid oxide can comprise any oxide that is characterized by a high surface area, and the electron-withdrawing anion can comprise any anion that increases the acidity of the solid oxide as compared to the solid oxide that is not treated with at least one electron-withdrawing anion.

The solid oxides described herein are chemically treated with at least one electron-withdrawing anion to provide the support activator. For example, the at least one electron-withdrawing anion can comprise or can be selected from fluoride, chloride, bromide, iodide, trifluoroacetate, sulfate, bisulfate, fluorosulfate, a $C_1$-$C_{10}$ alkyl sulfonate (for example, mesylate or methanesulfonate), a $C_6$-$C_{14}$ aryl sulfonate (for example, tosylate or toluenesulfonate), a $C_1$-$C_{10}$ fluoroalkyl sulfonate (for example, triflate or trifluoromethanesulfonate), a $C_6$-$C_{14}$ fluoroaryl sulfonate (for example, for example, $[CF_3C_6H_4SO_3]^-$), thiosulfate, fluoroborate, phosphate, fluorophosphates (monofluorophosphate and/or difluorophosphate), fluorozirconate, fluorotitanate, phosphotungstate, or similar anions, or any combination thereof.

In an aspect, for example, the chemically-modified solid oxide can comprise a solid oxide that is chemically-modified with an electron-withdrawing anion, and wherein the electron-withdrawing anion comprises or is selected from sulfate, bisulfate, fluorosulfate, phosphate, fluorophosphate, triflate, mesylate, tosylate, thiosulfate, $C_1$-$C_{10}$ alkyl sulfonate, $C_6$-$C_{14}$ aryl sulfonate, fluoride, chloride, or any combination thereof. In a further aspect, the chemically-modified solid oxide can be generated by treatment of a solid oxide with sulfuric acid, sulfate ion, bisulfate ion, fluorosulfuric acid, fluorosulfate ion, phosphoric acid, phosphate ion, fluorophosphoric acid, monofluorophosphate ion, triflic (trifluoromethanesulfonic) acid, triflate trifluoromethanesulfonate) ion, methanesulfonic acid, mesylate (methanesulfonate) ion, toluenesulfonic acid, tosylate (toluenesulfonate) ion, thiosulfate ion, $C_1$-$C_{10}$ alkyl sulfonic acid, $C_1$-$C_{10}$ alkyl sulfonate ion, $C_6$-$C_{14}$ aryl sulfonic acid, $C_6$-$C_{14}$ aryl sulfonate ion, fluoride ion, chloride ion, or any combination thereof.

By way of example, in the process according to this disclosure, the chemically-modified solid oxide can comprise, can consist of, can consist essentially of, or can be selected from fluorided alumina, chlorided alumina, bromided alumina, fluorided-chlorided alumina, sulfated alumina, fluorided silica-alumina, chlorided silica-alumina, bromided silica-alumina, fluorided-chlorided silica-alumina, sulfated silica-alumina, fluorided silica-titania, chlorided silica-titania, bromided silica-titania, fluorided-chlorided silica-titania, sulfated silica-titania, fluorided silica-zirconia, chlorided silica-zirconia, bromided silica-zirconia, fluorided-chlorided silica-zirconia, sulfated silica-zirconia, fluorided silica-coated alumina, chlorided silica-coated alumina, bromided silica-coated alumina, fluorided-chlorided silica-coated alumina, sulfated silica-coated alumina, fluorided mullite, chlorided mullite, bromided mullite, fluorided-chlorided mullite, or sulfated mullite.

In other aspects, for example, in the process according to this disclosure the chemically-modified solid oxide can comprise, can consist of, can consist essentially of, or can be selected from a bisulfated, a fluorosulfated, a phosphated, a fluorophosphated, a $C_1$-$C_{10}$ alkyl sulfonated, a $C_6$-$C_{14}$ aryl sulfonated, a $C_1$-$C_{10}$ fluoroalkyl sulfonated, a $C_6$-$C_{14}$ fluoroaryl sulfonated, or a thiosulfated solid oxide, or a combination thereof, wherein the solid oxide is selected independently from alumina, silica-alumina, silica-titania, silica-zirconia, silica-coated alumina, mullite, or a combination thereof.

In another aspect and in any embodiment of this disclosure, for example, the chemically-modified solid oxide can comprise at least one silica-coated alumina treated with at least one electron-withdrawing anion, wherein: the at least one silica-coated alumina has a weight ratio of alumina to silica in a range from about 1:1 to about 100:1, and the at least one electron-withdrawing anion comprises fluoride, chloride, bromide, phosphate, triflate, bisulfate, sulfate, or any combination thereof.

In a further aspect, the chemically-modified solid oxide comprises, consists of, consists essentially of silica-coated alumina that has been fluorided and chlorided. In this aspect, the silica-coated alumina can comprise from about 10 wt. % to about 80 wt. % silica, based on the weight of the silica-coated alumina; the fluorided-chlorided silica-coated alumina comprises from about 2 wt. % to about 15 wt. % F, based on the weight of the fluorided-chlorided silica-coated alumina; and/or the fluorided-chlorided silica-coated alumina comprises from about 1 wt. % to about 10 wt. % Cl, based on the weight of the fluorided-chlorided silica-coated alumina. In this process, the fluorided-chlorided silica-coated alumina can be produced by a process comprising: (a) calcining a silica-coated alumina at a peak calcining temperature to produce a calcined silica-coated alumina; (b) contacting the calcined silica-coated alumina with a chlorine-containing compound and calcining at a peak chloriding temperature to produce a chlorided silica-coated alumina; and (c) contacting the chlorided silica-coated alumina with a fluorine-containing compound and calcining at a peak fluoriding temperature to produce the fluorided-chlorided silica-coated alumina. The fluorided-chlorided silica-coated alumina can have, for example, a pore volume in a range from about 0.9 mL/g to about 2.0 mL/g; and a surface area in a range from about 200 $m^2$/g to about 700 $m^2$/g.

In yet a further aspect and in any embodiment of this disclosure, the chemically-modified solid oxide can comprise the contact product of at least one solid oxide compound and at least one electron-withdrawing anion source. The solid oxide compound and electron-withdrawing anion source are described independently herein and may be utilized in any combination to further describe the chemically-modified solid oxide comprising the contact product of at least one solid oxide compound and at least one electron-withdrawing anion source. That is, the chemically-modified solid oxide is provided upon contacting or treating the solid oxide with the electron-withdrawing anion source. In an aspect, the solid oxide compound can comprise or can be selected from an inorganic oxide.

In an aspect, the solid oxide compound can be calcined prior to contacting with the electron-withdrawing anion source, though this is not required. In another aspect, the solid oxide compound can be calcined during or after contacting with the electron-withdrawing anion source. Thus, contact product of the solid oxide and the electron-withdrawing anion may be calcined either during or after the solid oxide compound is contacted with the electron-withdrawing anion source. In this aspect, the solid oxide compound may be calcined or uncalcined. In another aspect, the activator may comprise the contact product of at least one calcined solid oxide compound and at least one electron-withdrawing anion source.

While not intending to be bound by theory, the chemically-modified solid oxide is thought to function as a co-catalyst or activator when used as disclosed herein. Moreover, the chemically-modified solid oxide is thought to function as a better co-catalyst or activator as compared to the non-chemically-modified oxide. The activation function of the chemically-modified solid oxide is evident in the enhanced activity of activator as a whole, as compared to an activator containing the corresponding untreated solid oxide.

In one aspect of this disclosure, the chemically-modified solid oxide further also can comprise a metal or metal ion selected from zinc, nickel, vanadium, titanium, silver, copper, gallium, tin, tungsten, molybdenum, or any combination thereof; alternatively, the chemically-modified solid oxide further can comprise a metal or metal ion selected from zinc, nickel, vanadium, titanium, or tin, or any combination thereof; alternatively, the chemically-modified solid oxide can further comprise a metal or metal ion selected from zinc, nickel, vanadium, tin, or any combination thereof.

Examples of chemically-modified solid oxides that further comprise a metal or metal ion include, but are not limited to, zinc-impregnated chlorided alumina, titanium-impregnated fluorided alumina, zinc-impregnated fluorided alumina, zinc-impregnated chlorided silica-alumina, zinc-impregnated fluorided silica-alumina, zinc-impregnated sulfated alumina, chlorided zinc aluminate, fluorided zinc aluminate, sulfated zinc aluminate, or any combination thereof; alternatively, the chemically-modified solid oxide can be selected from fluorided alumina, chlorided alumina, sulfated alumina, fluorided silica-alumina, chlorided silica-alumina, sulfated silica-alumina, fluorided silica-zirconia, sulfated silica-zirconia, or any combination thereof.

In one aspect of this disclosure, the solid oxide material is chemically-modified by contacting it with at least one electron-withdrawing component, typically an electron-withdrawing anion source. Further, the solid oxide material can be chemically-modified with a metal ion if desired, then calcining to form a metal-containing or metal-impregnated chemically-modified solid oxide. Alternatively, a solid oxide material and an electron-withdrawing anion source are contacted and calcined simultaneously. The method by which the oxide is contacted with an electron-withdrawing component, typically a salt or an acid of an electron-withdrawing anion, includes, but is not limited to, gelling, co-gelling, impregnation of one compound onto another, and the like. Typically, following any contacting method, the contacted mixture of oxide compound, electron-withdrawing anion, and the metal ion if present can be calcined.

Without being bound by theory, the electron-withdrawing component used to treat the oxide can be any component that increases the Lewis or Brønsted acidity of the solid oxide upon treatment. In one aspect, the electron-withdrawing component is an electron-withdrawing anion derived from a salt, an acid, or other compound such as a volatile organic compound that may serve as a source or precursor for that anion. Examples of electron-withdrawing anions include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, trifluoroacetate, triflate, and the like, including mixtures and combinations thereof; alternatively, examples of electron-withdrawing anions include, but are not limited to, sulfate, bisulfate, fluoride, chloride, fluorosulfate, fluoroborate, phosphate, fluorophosphate, trifluoroacetate, triflate, fluorozirconate, fluorotitanate, and the like, including mixtures and combinations thereof; alternatively, examples of electron-withdrawing anions include, but are not limited to, fluoride, sources of fluoride, chloride, bisulfate, sulfate, and the like, including mixtures and combinations thereof. In addition, other ionic or non-ionic compounds that serve as sources for these electron-withdrawing anions may also be employed in the present disclosure.

When the electron-withdrawing component can comprise a salt of an electron-withdrawing anion, the counterion or cation of that salt may be selected from any cation that allows the salt to revert or decompose back to the acid during calcining. Factors that dictate the suitability of the particular salt to serve as a source for the electron-withdrawing anion include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion include, but are not limited to, ammonium, trialkyl ammonium, tetraalkyl ammonium, tetraalkyl phosphonium, $H^+$, $[H(OEt_2)_2]^+$, and the like; alternatively, ammonium; alternatively, trialkyl ammonium; alternatively, tetraalkyl ammonium; alternatively, tetraalkyl phosphonium; or alternatively, $H^+$, $[H(OEt_2)_2]^+$.

Further, combinations of one or more different electron-withdrawing anions, in varying proportions, can be used to tailor the specific activity of the chemically-modified solid oxide to the desired level. Combinations of electron-withdrawing components may be contacted with the oxide material simultaneously or individually, and any order that affords the desired chemically-modified solid oxide acidity. For example, one aspect of this disclosure is employing two or more electron-withdrawing anion source compounds in two or more separate contacting steps. Thus, one example of such a process by which an chemically-modified solid oxide can be prepared is as follows: a selected solid oxide compound, or combination of oxide compounds, is contacted with a first electron-withdrawing anion source compound to form a first mixture, this first mixture is then calcined, the calcined first mixture is then contacted with a second electron-withdrawing anion source compound to form a second mixture, followed by calcining said second mixture to form a treated solid oxide compound. In such a process, the first and second electron-withdrawing anion source compounds are typically different compounds, although they may be the same compound.

In one aspect of the disclosure, the chemically-modified solid oxide may be produced by a process comprising:
1) contacting a solid oxide compound with at least one electron-withdrawing anion source compound to form a first mixture; and
2) calcining the first mixture to form the chemically-modified solid oxide.

In another aspect of this disclosure, the chemically-modified solid oxide can be produced by a process comprising:
1) contacting at least one solid oxide compound with a first electron-withdrawing anion source compound to form a first mixture; and
2) calcining the first mixture to produce a calcined first mixture;
3) contacting the calcined first mixture with a second electron-withdrawing anion source compound to form a second mixture; and
4) calcining the second mixture to form the chemically-modified solid oxide.

Thus, the solid oxide activator-support is sometimes referred to simply as a treated solid oxide compound.

In one aspect of this disclosure, once the solid oxide has been treated and dried, it may be subsequently calcined. Calcining the chemically treated solid oxide is generally conducted in an ambient atmosphere; alternatively, in a dry ambient atmosphere. The solid oxide may be calcined at a temperature from about 200° C. to about 900° C.; alternatively, from about 300° C. to about 800° C.; alternatively, from about 400° C. to about 700° C.; or alternatively, from about 350° C. to about 550° C. The period of time at which the solid oxide is maintained at the calcining temperature may be about 1 minute to about 100 hours; alternatively, from about 1 hour to about 50 hours; alternatively, from about 3 hours to about 20 hours; or alternatively, from about 1 to about 10 hours.

Further, any type of suitable ambient atmosphere can be used during calcining. Generally, calcining is conducted in an oxidizing atmosphere, such as air. Alternatively, an inert atmosphere, such as nitrogen or argon, or a reducing atmosphere such as hydrogen or carbon monoxide, may be used.

In another aspect of the disclosure, the solid oxide component used to prepare the chemically-modified solid oxide has a pore volume greater than about 0.1 cc/g. In another aspect, the solid oxide component has a pore volume greater than about 0.5 cc/g, and in yet another aspect, greater than about 1.0 cc/g. In still another aspect, the solid oxide component has a surface area from about 100 $m^2/g$ to about 1000 $m^2/g$. In another aspect, solid oxide component has a surface area from about 200 $m^2/g$ to about 800 $m^2/g$, and in still another aspect, from about 250 $m^2/g$ to about 600 $m^2/g$.

The solid oxide material may be treated with a source of halide ion or sulfate ion, or a combination of anions, and optionally treated with a metal ion, then calcined to provide the chemically-modified solid oxide in the form of a particulate solid. In one aspect, the solid oxide material is treated with a source of sulfate, termed a sulfating agent, a source of chloride ion, termed a chloriding agent, a source of fluoride ion, termed a fluoriding agent, or a combination thereof, and calcined to provide the solid oxide activator.

In one aspect, the chemically-modified solid oxide can comprise a fluorided solid oxide in the form of a particulate solid, thus a source of fluoride ion is added to the oxide by treatment with a fluoriding agent. In still another aspect, fluoride ion may be added to the oxide by forming a slurry of the oxide in a suitable solvent such as alcohol or water, including, but are not limited to, the one to three carbon alcohols because of their volatility and low surface tension. Examples of fluoriding agents that can be used in this disclosure include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4$)$_2SiF_6$), ammonium hexafluorophosphate ($NH_4PF_6$), analogs thereof, and combinations thereof; alternatively, hydrofluoric acid (HF), ammonium fluoride ($NH_4F$), ammonium bifluoride ($NH_4HF_2$), ammonium tetrafluoroborate ($NH_4BF_4$), analogs thereof, and combinations thereof. For example, ammonium bifluoride $NH_4HF_2$ may be used as the fluoriding agent, due to its ease of use and ready availability.

In another aspect of the present disclosure, the solid oxide can be treated with a fluoriding agent during the calcining step. Any fluoriding agent capable of thoroughly contacting the solid oxide during the calcining step can be used. For example, in addition to those fluoriding agents described previously, volatile organic fluoriding agents may be used. Examples of volatile organic fluoriding agents useful in this aspect of the disclosure include, but are not limited to, freons, perfluorohexane, perfluorobenzene, fluoromethane, trifluoroethanol, and combinations thereof. Gaseous hydrogen fluoride or fluorine itself can also be used with the solid oxide is fluorided during calcining. One convenient method of contacting the solid oxide with the fluoriding agent is to vaporize a fluoriding agent into a gas stream used to fluidize the solid oxide during calcination.

Similarly, in another aspect of this disclosure, the chemically-modified solid oxide can comprise a chlorided solid oxide in the form of a particulate solid, thus a source of chloride ion is added to the oxide by treatment with a chloriding agent. The chloride ion may be added to the oxide by forming a slurry of the oxide in a suitable solvent. In another aspect of the present disclosure, the solid oxide can be treated with a chloriding agent during the calcining step. Any chloriding agent capable of serving as a source of chloride and thoroughly contacting the oxide during the calcining step can be used. For example, volatile organic chloriding agents may be used. Examples of volatile organic chloriding agents useful in this aspect of the disclosure include, but are not limited to, certain freons, perchlorobenzene, chloromethane, dichloromethane, chloroform, carbon tetrachloride, trichloroethanol, or any combination thereof. Gaseous hydrogen chloride or chlorine itself can also be used with the solid oxide during calcining. One convenient method of contacting the oxide with the chloriding agent is to vaporize a chloriding agent into a gas stream used to fluidize the solid oxide during calcination.

In one aspect, the amount of fluoride or chloride ion present before calcining the solid oxide is generally from about 2% by weight to about 50% by weight, where the weight percents are based on the weight of the solid oxide, for example silica-alumina, before calcining. In another aspect, the amount of fluoride or chloride ion present before calcining the solid oxide is from about 3% by weight to about 25% by weight, and in another aspect, from about 4% by weight to about 20% by weight. Once impregnated with halide, the halided oxide may be dried by any method known in the art including, but not limited to, suction filtration followed by evaporation, drying under vacuum, spray drying, and the like, although it is also possible to initiate the calcining step immediately without drying the impregnated solid oxide.

In an aspect, silica-alumina may be utilized as the solid oxide material. The silica-alumina used to prepare the treated silica-alumina can have a pore volume greater than about 0.5 cc/g. In one aspect, the pore volume may be greater than about 0.8 cc/g, and in another aspect, the pore volume may be greater than about 1.0 cc/g. Further, the silica-alumina may have a surface area greater than about 100 $m^2/g$. In one aspect, the surface area is greater than about 250 $m^2/g$, and in another aspect, the surface area may be greater than about 350 $m^2/g$. Generally, the silica-alumina of this disclosure has an alumina content from about 5 to about 95%. In one aspect, the alumina content of the silica-alumina may be from about 5 to about 50%, and in another aspect, the alumina content of the silica-alumina may be from about 8% to about 30% alumina by weight. In yet another aspect, the solid oxide component can comprise alumina without silica and in another aspect, the solid oxide component can comprise silica without alumina.

The sulfated solid oxide can comprise sulfate and a solid oxide component such as alumina or silica-alumina, in the form of a particulate solid. The sulfated oxide can be further treated with a metal ion if desired such that the calcined sulfated oxide can comprise a metal. In one aspect, the sulfated solid oxide can comprise sulfate and alumina. In one aspect of this disclosure, the sulfated alumina is formed by a process wherein the alumina is treated with a sulfate source, for example selected from, but not limited to, sulfuric acid or a sulfate salt such as ammonium sulfate. In one aspect, this process may be performed by forming a slurry of the alumina in a suitable solvent such as alcohol or water, in which the desired concentration of the sulfating agent has been added. Suitable organic solvents include, but are not limited to, the one to three carbon alcohols because of their volatility and low surface tension.

In one aspect of the disclosure, the amount of sulfate ion present before calcining is generally from about 0.5 parts by weight to about 100 parts by weight sulfate ion to about 100 parts by weight solid oxide. In another aspect, the amount of sulfate ion present before calcining is generally from about 1 part by weight to about 50 parts by weight sulfate ion to about 100 parts by weight solid oxide, and in still another aspect, from about 5 parts by weight to about 30 parts by weight sulfate ion to about 100 parts by weight solid oxide. These weight ratios are based on the weight of the solid oxide before calcining. Once impregnated with sulfate, the sulfated oxide may be dried by any method known in the art including, but not limited to, suction filtration followed by evaporation, drying under vacuum, spray drying, and the like, although it is also possible to initiate the calcining step immediately.

In addition to being treated with an electron-withdrawing component (for example, halide or sulfate ion), the solid inorganic oxide of this disclosure can be treated with a metal source if desired, including metal salts or metal-containing compounds. In one aspect of the disclosure, these compounds may be added to or impregnated onto the solid oxide in solution form, and subsequently converted into the supported metal upon calcining. The solid oxide may be treated with metal salts or metal-containing compounds before, after, or at the same time that the solid oxide is treated with the electron-withdrawing anion.

Further, any method of impregnating the solid oxide material with a metal may be used. The method by which the oxide is contacted with a metal source, typically a salt or metal-containing compound, includes, but is not limited to, gelling, co-gelling, impregnation of one compound onto another, and the like. Following any contacting method, the contacted mixture of oxide compound, electron-withdrawing anion, and the metal ion is typically calcined. Alternatively, a solid oxide material, an electron-withdrawing anion source, and the metal salt or metal-containing compound are contacted and calcined simultaneously.

Various processes to prepare solid oxide activator-supports that can be employed in this disclosure have been reported. For example, U.S. Pat. Nos. 6,107,230, 6,165,929, 6,294,494, 6,300,271, 6,316,553, 6,355,594, 6,376,415, 6,391,816, 6,395,666, 6,524,987, 6,548,441, 6,750,302, 6,831,141, 6,936,667, 6,992,032, 7,601,665, 7,026,494, 7,148,298, 7,470,758, 7,517,939, 7,576,163, 7,294,599, 7,629,284, 7,501,372, 7,041,617, 7,226,886, 7,199,073, 7,312,283, 7,619,047, 7,884,163, 8,703,886, and 9,023,959 describe such methods, each of which is incorporated by reference herein, in pertinent part.

Metal-Treated Chemically-Modified Solid Oxides (MT-CMSO) and Metal-Treated Solid Oxides (MT-SO)

The disclosed catalyst systems and processes for producing α,β-unsaturated carboxylic acids or salts thereof can utilize as an activator a chemically-modified solid oxide (CMSO) or a solid oxide (SO) which has been treated with a metal base or equivalent such as a metal salt and a non-metal-containing base. In some embodiments, the CMSO or the SO can be treated with a metal salt to form their respective metal-treated materials. The metal-treated solid oxides include a solid oxide that has not been chemically-modified with an electron-withdrawing anion prior to treatment with a metal-containing base, a metal salt, a metal salt in combination with a nonmetal-containing base, or an equivalent thereof. In this aspect, the solid oxide of the metal-treated solid oxide can comprise or can be selected from the same solid oxides as used in the metal-treated chemically-modified solid oxides (MT-CMSO), and therefore the solid oxides as used in the chemically-modified solid oxides (CMSO).

According to one aspect, for example, the chemically-modified solid oxides (CMSO) such as sulfur oxoacid anion-modified solid oxides, phosphorus oxoacid anion-modified solid oxides, or a halide ion-modified solid oxides, can be further treated with a source of a metal cation and a base, for example, a metal hydroxide or metal alkoxide comprising a metal cation selected from a Group 1, 2, 12 or 13 metal, to form metal-treated chemically-modified solid oxides (MT-CMSO). Similarly, metal oxides such as a silica, alumina, silica-alumina, silica-coated alumina, a silicate, an aluminosilicate or any metal oxide disclosed herein, such as a mesoporous silica, a mesostructured cellular foam (MCF) silica, a molecular sieve, or a zeolite can be further treated with a source of a metal cation and a base, for example, a metal hydroxide or metal alkoxide comprising a metal cation selected from a Group 1, 2, 12 or 13 metal, to form metal-treated solid oxide (MT-SO). When these materials are utilized for the metal-treated solid oxide (MT-SO), examples of the MT-SO include but are not limited to Na-MCM-41, Na/Al-KIT-6, Na—Y zeolite, Na-SBA-15, Na-treated trimodal porous silica (TMS), potassium L-zeolite, or any combination thereof.

In an aspect, the metal-treated chemically-modified solid oxides can be produced by, for example, contacting any suitable solid oxide and any suitable electron-withdrawing anion as described herein and calcining (concurrently and/or subsequently) to form the chemically-modified solid oxide CMSO. The CMSO may then contacted with any suitable source of the metal, that is, a metal-containing base which includes a basic moiety and a metal cation. Similarly, the metal-treated solid oxides can be produced by, for example, contacting any suitable solid oxide with any suitable source of the metal as described herein. For example, suitable metals for treating the CMSO or SO to form the MT-CMSO or MT-SO include, but are not limited to, the hydroxides, alkoxides, aryloxides, hydrides, amides, alkyl- or aryl-amides, dialkyl- or diaryl-amides, etc. of Group 1 (alkali) metals, Group 2 (alkaline earth) metals, Group 12 metals, and/or Group 13 metals, including any combinations thereof. Optionally, a further calcining step can be used. In one aspect, the MT-CMSO or the MT-SO can be prepared and used in the absence of a metal hydride.

The metal-treated chemically-modified solid oxide or the metal-treated solid oxide can comprise an alkali metal, an alkaline earth metal, a transition metal, or any combination thereof (e.g., a transition metal and an alkali metal). When the MT-CMSO or MT-SO comprise an alkali metal, these metal-treated materials may be referred to as an alkali metal-treated chemically-modified solid oxide or an alkali metal-treated solid oxide, and the alkali metal often comprises sodium, potassium, or cesium, either singly or in combination. Similarly, when the MT-CMSO or the MT-SO comprise an alkaline earth metal, these metal-treated materials may be referred to as an alkaline earth metal-treated chemically-modified solid oxide or an alkaline earth metal-treated solid oxide, and the alkaline earth metal often comprises magnesium, calcium, or barium, either singly or in combination.

Illustrative and non-limiting examples of metal-treated chemically-modified solid oxides can include sodium-treated chlorided alumina, sodium-treated sulfated alumina, sodium-treated sulfated silica-coated alumina, sodium-treated fluorided silica-coated alumina, sodium-treated fluorided silica-alumina, sodium-treated fluorided-chlorided silica-coated alumina, and the like, as well as combinations thereof. Illustrative and non-limiting examples of metal-treated solid oxides can include, for example, sodium-treated alumina, sodium-treated silica, sodium-treated silica-coated alumina, sodium-treated or potassium-treated zeolites, Na-MCM-41, Na/Al-KIT-6, Na—Y zeolite, Na-SBA-15, sodium (Na)-treated trimodal porous silica (TMS), potassium L-zeolite, or any combination thereof.

The MT-CMSO or the MT-SO can be prepared from the CMSO or SO, respectively, as shown in FIG. 1, which illustrates the regeneration of the MT-CMSO or MT-SO from the CMSO or SO, namely by their respective treatment with a metal-containing base such as a metal hydroxide or metal alkoxide 7, or metal alkyl amide or the like, or the equivalent such as the treatment of the CMSO or SO with a metal salt and a non-metal-containing base. While not intending to be theory-bound, the resulting MT-CMSO or MT-SO is believed to have accessible metal sites that are capable of interacting with the metalalactone, for example, as illustrated in FIG. 1. Also while not intending to be bound by theory, the CMSO is generally a Lewis acidic solid oxide ("solid super acid"), which forms when a solid oxide is treated with an electron-withdrawing anion in acid form or salt form, in which cation of the salt form reverts or decomposes back to the acid during calcining. Thus, it is believed that treatment of the acidic CMSO with a metal-containing base such as a metal hydroxide or metal alkoxide forms the metalated form of the CMSO referred to herein as the MT-CMSO. Similarly, it is believed that treatment of the generally acidic solid oxide (SO) with a metal-containing base such as a metal hydroxide or metal alkoxide or in some embodiments forms the metalated form of the SO, of the MT-SO.

In one aspect, the metal-treated chemically-modified solid oxide can be prepared by [a] contacting a solid oxide with a sulfur oxoacid anion, a phosphorus oxoacid anion, or a halide ion to provide the chemically-modified solid oxide, followed by [b] contacting the chemically-modified solid oxide with a metal-containing base. In this aspect, the sulfur oxoacid anion can be provided by sulfuric acid or a sulfate salt, the phosphorus oxoacid anion can be provided by phosphoric acid or a phosphate salt, and the halide ion can be provided by a hydrohalic acid or a halide salt. In a similar manner, once the reaction mixture has been subjected to reaction conditions suitable to form the α,β-unsaturated carboxylic acid or the salt thereof, the remaining oxide co-catalyst can be regenerated to the metal-treated chemically-modified solid oxide, by, for example, contacting the solid oxide remaining following the elimination step with a metal-containing base. For example, referring again to FIG. 1, the CMSO can be regenerated to the MT-CMSO by treatment with a metal-containing base.

According to a further aspect, the metal-treated chemically-modified solid oxide and the metal-treated solid oxide can comprise any suitable Lewis acidic metal cation or any Lewis acidic metal cation disclosed herein. In one aspect, the metal-treated chemically-modified solid oxide can comprise a metal cation selected from a Group 1, 2, 12 or 13 metal. The MT-CMSO and the MT-SO can comprise an alkali metal cation, an alkaline earth metal cation, or any combination thereof. In another aspect, the MT-CMSO and the MT-SO can comprise at least one cation selected from lithium, sodium, potassium, rubidium, cesium, magnesium, calcium, strontium, barium, copper, zinc, aluminum, or gallium. In particular, the, the MT-CMSO and the MT-SO can comprise sodium ions or potassium ions.

In one aspect, the metal-containing base that can be used to convert the CMSO to the MT-CMSO and convert the SO to the MT-SO as described can comprise or can be selected from any suitable base or any base disclosed herein, e.g., carbonates (e.g., $Na_2CO_3$, $K_2CO_3$, $Cs_2CO_3$, $CaCO_3$, $MgCO_3$), hydroxides (e.g., NaOH, KOH, $Mg(OH)_2$), alkoxides (e.g., $Na(O^tBu)$, $K(O^tBu)$, $Mg(OEt)_2$, $Al(O^iPr)_3$), aryloxides which can be unsubstituted, hydrocarbyl-substituted, or halide-substituted (e.g. $Na(OC_6H_5)$, $K(OC_6H_5)$, $Na(O-2-C_6H_4F)$, $K(O-2-C_6H_4F)$, $Na(O-2-C_6H_4Cl)$, $K(O-2-C_6H_4Cl)$, $Na(O-4-C_6H_4F)$, $K(O-4-C_6H_4F)$, $Na(O-4-C_6H_4Cl)$, $K(O-4-C_6H_4Cl)$, $Na(O-2-C_6H_4Me)$, $K(O-2-C_6H_4Me)$, $Na(O-4-C_6H_4Me)$, $K(O-4-C_6H_4Me)$, $Na(O-2,6-C_6H_3Me_2)$, $K(O-2,6-C_6H_3Me_2)$, $Na(O-2,4,6-C_6H_2Me_3)$, $K(O-2,4,6-C_6H_2Me_3)$, $Na(O-2,6-C_6H_4-i-Pr_2)$, $K(O-2,6-C_6H_4-i-Pr_2)$, $Na(O-3,5-C_6H_3Me_2)$, $K(O-3,5-C_6H_3Me_2)$, sulfates (e.g. $Na_2SO_4$, $K_2SO_4$, $CaSO_4$, $MgSO_4$), and phosphates (e.g. $Na_3PO_4$, $K_3PO_4$), and the like.

According to another aspect, the metal-containing bases can comprise or can be selected from alkali metal hydroxides or alkali metal alkoxides. In one aspect, the metal-containing bases can comprise or can be selected from alkali metal alkoxide, alkali metal aryloxide, alkali metal amide, alkali metal alkyl amide, alkali metal arylamide, alkali metal hydride, and the like. In another aspect, metal-containing bases can comprise or can be selected from any metal-containing alkoxide, aryloxide, alkylamide, arylamide, hydride or polyhydride, and/or substituted analogs thereof. Further, the metal-containing bases used according to this disclosure can be absent any specific metal-containing alkoxide, aryloxide, alkylamide, arylamide, hydride, or polyhydride, and/or substituted analogs thereof. For example, the metal-containing base can be absent a hydride compound such as NaH or KH. In another aspect, the MT-CMSO or the MT-SO can be generated by contacting a CMSO or contacting a SO with a metal-containing base, wherein the metal-containing base is absent sodium hydride, an aryloxide salt (such as a sodium aryloxide), an alkoxide salt (such as a sodium tert-butoxide), and/or a phosphazene.

In an aspect, in the processes described herein, the metal-treated chemically-modified solid oxide or the metal-treated solid oxide can be produced by a process comprising contacting any suitable chemically-modified solid oxide or any chemically-modified solid oxide disclosed herein, or contacting any suitable solid oxide or any solid oxide disclosed herein, with any suitable metal-containing basic compound or any metal-containing basic compound disclosed herein to provide a mixture, and concurrently and/or subsequently drying and/or calcining the mixture. In an aspect, the MT-CMSO can be produced by a process comprising contacting any suitable solid oxide with an electron-withdrawing anion to form a first mixture and concurrently and/or subsequently drying and/or calcining the first mixture, followed by contacting the dried and/or calcined first mixture with any suitable metal-containing basic compound to provide a second mixture, and concurrently and/or subsequently drying and/or calcining the second mixture. According to another aspect, the MT-CMSO can be produced by a process comprising contacting any suitable solid oxide and any suitable electron-withdrawing anion and calcining (concurrently and/or subsequently) to form the chemically-modified solid oxide (CMSO), and contacting the chemically-modified solid oxide with any suitable metal-containing compound.

The metal-treated chemically-modified solid oxide or the metal-treated solid oxide can comprise a chemically-modified solid oxide (CMSO) or a solid oxide (SO), respectively, treated with a metal-containing base or an equivalent, such as an alkali metal base, an alkaline earth metal base, or any combination thereof in a total amount of from 1 wt. % to 35 wt. %, from 2 wt. % to 30 wt. %, from 3 wt. % to 25 wt. %, or from 5 wt. % to 20 wt. %, based on the total weight of the metal-treated chemically-modified solid oxide or the metal-treated solid oxide. In another aspect, any metal present in the MT-CMSO or the MT-SO can be present in an amount of at least about 0.1 wt. %, at least about 0.25 wt. %, at least 0.5 wt. %, at least 1 wt. %, or at least 2 wt. %, and can be present in concentrations up to 35 wt. %, up to 30 wt. %, up to 25 wt. %, up to 20 wt. %, up to 15 wt. %, up to 12 wt. %, up to 10 wt. %, up to 8 wt. %, up to 7 wt. %, or up to up to 5 wt. %. For instance, the MT-CMSO or the MT-SO generally can contain from 1 wt. % to 25 wt. %, from 2 wt. % to 30 wt. %, from 2 wt. % to 25 wt. %, from 5 to 30 wt. %, from 5 wt. % to 25 wt. %, from 3 wt. % to 15 wt. %, from 5 wt. % to 12 wt. %, or from 6 wt. % to 18 wt. %, of the metal from the metal-containing base, based on the total weight of the metal-treated chemically-modified solid oxide.

Diluents

In an aspect, the process to prepare a catalyst system in which at least a portion of the Group 8-11 transition metal in some form is deposited onto or impregnated into the MT-CMSO or the MT-SO is carried out in the presence of a diluent. In embodiments, this process can be carried out in the presence or absence of an olefin and $CO_2$ and if desired can be carried out at a total pressure greater than ambient pressure. Once the Group 8-11 transition metal catalyst or catalyst precursor is deposited onto or impregnated into the MT-CMSO or the MT-SO activator-support, the catalytic formation of an $\alpha,\beta$-unsaturated carboxylic acids and salts thereof can be carried out in the presence or absence of a diluent.

Mixtures and combinations of diluents can be utilized in these processes. The diluent can comprise, consist essentially of, or consist of, any suitable solvent or any solvent disclosed herein, unless otherwise specified. For example, the diluent can comprise, consist essentially of, or consist of a non-protic solvent, a protic solvent, a non-coordinating solvent, or a coordinating solvent. For instance, in accordance with one aspect of this disclosure, the diluent can comprise a non-protic solvent. Representative and non-limiting examples of non-protic solvents can include tetrahydrofuran (THF), 2,5-Me$_2$THF, acetone, toluene, chlorobenzene, pyridine, acetonitrile, carbon dioxide, olefin, and the like, as well as combinations thereof. In accordance with another aspect, the diluent can comprise a weakly coordinating or non-coordinating solvent. Representative and non-limiting examples of weakly coordinating or non-coordinating solvents can include toluene, chlorobenzene, paraffins, halogenated paraffins, and the like, as well as combinations thereof.

In accordance with yet another aspect, the diluent can comprise a carbonyl-containing solvent, for instance, ketones, esters, amides, and the like, as well as combinations thereof. Representative and non-limiting examples of carbonyl-containing solvents can include acetone, ethyl methyl ketone, ethyl acetate, propyl acetate, butyl acetate, isobutyl isobutyrate, methyl lactate, ethyl lactate, N,N-dimethylformamide, and the like, as well as combinations thereof. In still another aspect, the diluent can comprise THF, 2,5-Me$_2$THF, methanol, acetone, toluene, chlorobenzene, pyridine, anisole, or a combination thereof; alternatively, THF; alternatively, 2,5-Me$_2$THF; alternatively, methanol; alternatively, acetone; alternatively, toluene; alternatively, chlorobenzene; or alternatively, pyridine.

In an aspect, the diluent can comprise (or consist essentially of, or consist of) an aromatic hydrocarbon solvent. Non-limiting examples of suitable aromatic hydrocarbon solvents that can be utilized singly or in any combination include benzene, toluene, xylene (inclusive of ortho-xylene, meta-xylene, para-xylene, or mixtures thereof), and ethylbenzene, or combinations thereof; alternatively, benzene; alternatively, toluene; alternatively, xylene; or alternatively, ethylbenzene.

In an aspect, the diluent can comprise (or consist essentially of, or consist of) a halogenated aromatic hydrocarbon solvent. Non-limiting examples of suitable halogenated aromatic hydrocarbon solvents that can be utilized singly or in any combination include chlorobenzene, dichlorobenzene, and combinations thereof; alternatively, chlorobenzene; or alternatively, dichlorobenzene.

In an aspect, the diluent can comprise (or consist essentially of, or consist of) an ether solvent. Non-limiting examples of suitable ether solvents that can be utilized singly or in any combination include dimethyl ether, diethyl ether, diisopropyl ether, di-n-propyl ether, di-n-butyl ether, diphenyl ether, methyl ethyl ether, methyl t-butyl ether, dihydrofuran, tetrahydrofuran (THF), 2,5-Me$_2$THF, 1,2-dimethoxyethane, 1,4-dioxane, anisole, and combinations thereof; alternatively, diethyl ether, dibutyl ether, THF, 2,5-Me$_2$THF, 1,2-dimethoxyethane, 1,4-dioxane, and combinations thereof; alternatively, THF; or alternatively, diethyl ether.

In a further aspect, any of these aforementioned diluents can be excluded from the diluent or diluent mixture. For example, the diluent can be absent a phenol or a substituted phenol, an alcohol or a substituted alcohol, an amine or a substituted amine, water, an ether, an aliphatic hydrocarbon solvent, an aromatic hydrocarbon solvent, an aldehyde or ketone, an ester or amide, and/or absent a halogenated aromatic hydrocarbon, or any substituted analogs of these diluents halogenated analogs, including any of the aforementioned diluents. Therefore, Applicant reserves the right to exclude any of the diluents provided herein.

The diluent can comprise carbon dioxide, and can also comprise $CO_2$ under pressure. The diluent also can comprise the $\alpha,\beta$-unsaturated carboxylic acid or the salt thereof, formed in the process. The diluent can comprise any suitable non-protic solvent, any non-protic solvent disclosed herein, and/or carbon dioxide ($CO_2$) under pressure. The diluent can comprise any suitable non-protic solvent, any non-protic solvent disclosed herein, the olefin such as ethylene, and/or carbon dioxide ($CO_2$) under pressure. Specifically, the diluent can comprise the olefin such as ethylene and carbon dioxide ($CO_2$) under pressure. The diluent also can comprise any suitable weakly coordinating or non-coordinating solvent, or any weakly coordinating or non-coordinating solvent disclosed herein.

Moreover, a first diluent can be used to prepare a catalyst system in which at least a portion of the Group 8-11 transition metal in some form is impregnated into the MT-CMSO or the MT-SO. In embodiments, this first diluent can be removed, and the catalytic formation of an $\alpha,\beta$-unsaturated carboxylic acids and salts thereof can be carried out in the presence of a second diluent. The first diluent and the second diluent can comprise or can be selected from any of the diluents disclosed herein, and the second diluent can be the same as or can be different from the first diluent.

In all aspects and embodiments disclosed herein, the diluent can include or comprise carbon dioxide, olefin such as ethylene or other α-olefin, or combinations thereof. At least a portion of the diluent can comprise the α,β-unsaturated carboxylic acid or the salt thereof, formed in the process.

Group 8-11 Transition Metal Precursor Compounds and Metalalactone Compounds

In an aspect, the processes and catalysts of this disclosure can employ a metalalactone or a transition metal precursor compound from which a metalalactone can be formed in the presence of an olefin such as ethylene and $CO_2$. In the process for preparing a catalyst composition, a Group 8-11 transition metal precursor compound comprising at least one first ligand can be used in the formation of the catalyst composition, and at least one optional second ligand can be present. Similarly, a metalalactone compound comprising a Group 8-11 transition metal, a metalalactone moiety, and at least one ligand in addition to the metalalactone moiety can be used in the formation of the catalyst composition. These catalyst composition preparation processes involve contacting these transition metal compounds with a MT-CMSO or a MT-SO, wherein at least a portion of the Group 8-11 transition metal in some form is deposited on the MT-CMSO or a MT-SO.

In one aspect, some or all of the ligands on the Group 8-11 transition metal precursor compound can be displaced or some of the ligands can be retained when forming the Group 8-11 metalalactone compound from the transition metal precursor compound. In another aspect, at least some of the ligands on the Group 8-11 transition metal precursor compound or the Group 8-11 metalalactone compound can be displaced or retained when the at least a portion of the Group 8-11 transition metal in some form is deposited on the MT-CMSO or a MT-SO.

Accordingly in some embodiments, ligands for the Group 8-11 transition metal precursor compound such as the first ligand can be neutral electron donor ligands which may be relatively labile and can be displaced by more Lewis basic ligands, for example the optional second ligand. For example, the relatively labile 1,5-cyclooctadiene (abbreviated "COD") first ligand(s) of the Group 8 transition metal precursor compound $Ni(COD)_2$ can be displaced in the presence of the Lewis basic $(C_6H_{11})_2PCH_2CH_2P(C_6H_{11})_2)$ (abbreviated "dcpe") second ligand and ethylene to form $(dcpe)Ni(CH_2=CH_2)$. In the presence of $CO_2$, coupling the ethylene and $CO_2$ occurs to form the metalalactone complex $(dcpe)Ni(OC(O)CH_2CH_2)$. Accordingly, $Ni(COD)_2$ is a prototypical example of a transition metal precursor compound which loses its initial (first) ligands in the coupling reaction in the presence of a second (added) ligand, wherein the metalalactone incorporates the second (added) ligand(s) dcpe.

While the first ligand(s) can be less basic neutral electron donor ligands which can be replaced by the more Lewis basic second ligands, in some aspects, some of the first ligands of the transition metal precursor compound carry over and are retained by the metalalactone following the coupling reaction. Moreover, the ligands disclosed herein may function as a first ligand, may function a second ligand, or may function a ligand in addition to the metalalactone moiety of the Group 8-11 transition metal metalalactone compound. For example, the first ligand can be Lewis basic and can be displaced by another Lewis basic ligand such as a bidentate Lewis base or a more Lewis basic second ligand.

Therefore, the disclosure of a ligand as a neutral electron donor ligand or a first ligand does not preclude the ligand as being selected as a Lewis basic second ligand. The disclosure of a ligand as a Lewis basic second ligand does not preclude the ligand as being selected as a neutral electron donor first ligand. When describing ligands without specifically ascribing them as first ligands, second ligands, or a ligand in addition to the metalalactone moiety, it is intended that such ligands can function as either neutral electron donor first ligand or Lewis basic second ligand or the metalalactone ligand in addition to the metalalactone moiety.

As an example, metalalactones can be synthesized according to the following general reaction scheme shown in Scheme 1, which is illustrated with nickel as the transition metal and two 1,5-cyclooctadiene (COD) ligands as the at least one first ligand. Therefore, the Group 8-11 transition metal precursor compound in this reaction scheme is $Ni(COD)_2$, which is bis(1,5-cyclooctadiene) nickel(0). When the $Ni(COD)_2$ is contacted with ethylene and $CO_2$ in the presence of at least one second ligand represented as Ln in Scheme 1, the metalalactone compound $LnNi(OC(O)CH_2CH_2)$ is formed. In this example, and when the catalyst composition is prepared from the metalalactone compound $LnNi(OC(O)CH_2CH_2)$, the "ligand in addition to the metalalactone moiety" in the metalalactone compound is the same as the "second ligand" used in combination with $Ni(COD)_2$, ethylene, and $CO_2$ to form the metalalactone. Therefore, in an aspect, a ligand on a metalalactone compound (not including the metalalactone moiety) can comprise or can be selected from, but is not limited to, the same ligands as the second ligand used "second ligand" used with $Ni(COD)_2$, ethylene, and $CO_2$ to form the metalalactone.

Scheme 1

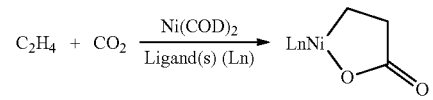

In another aspect, the first ligand can be 1,5-cyclooctadiene or TMEDA, and the second ligand or the ligand in addition to the metalalactone moiety can be a bidentate ligand such as a bidentate N,N compound or a bidentate P,P compound. For example, the second ligand or the ligand in addition to the metalalactone moiety can be 1,2-bis(dicyclohexylphosphino)ethane (dcpe) or TMEDA. Thus, some of the first ligand TMEDA can be retained in the metalalactone compound or some of the first ligand TMEDA can be replaced by dcpe.

The catalyst composition preparation involves contacting these transition metal compounds with a MT-CMSO or a MT-SO, wherein at least a portion of the Group 8-11 transition metal in some form is deposited on the MT-CMSO or a MT-SO. While the exact nature of the immobilized or deposited form of the Group 8-11 transition metal is unknown, some of the first or second ligands may be carried over and retained by the transition metal in the deposited or impregnated form. Alternatively, some of the first or second ligands may be released when the transition metal in the deposited or impregnated.

According to a further aspect, the transition metal catalyst or compound used in the processes can be used without being immobilized on a solid support. That is the transition metal catalyst can be used is its usual form, which is soluble in most useful solvents, without being bonded to or supported on any insoluble support, such as an inorganic oxide or mixed oxide material.

The transition metal of the metalalactone or of the transition metal precursor compound can be a Group 8, Group 9, Group 10, or Group 11 transition metal or any combination thereof, such as a Group 8 to Group 11 transition metal or a group 8 to Group 10 transition metal. In one aspect, for instance, the transition metal can be Fe, Co, Ni, Cu, Ru, Rh, Pd, Ag, Ir, Pt, or Au, while in another aspect, the transition metal can be Fe, Ni, or Rh. Alternatively, the transition metal can be Fe; alternatively, the transition metal can be Co; alternatively, the transition metal can be Ni; alternatively, the transition metal can be Cu; alternatively, the transition metal can be Ru; alternatively, the transition metal can be Rh; alternatively, the transition metal can be Pd; alternatively, the transition metal can be Ag; alternatively, the transition metal can be Ir; alternatively, the transition metal can be Pt; or alternatively, the transition metal can Au. In particular aspects contemplated herein, the transition metal can be Ni. Hence, the metalalactone can be a nickelalactone and the transition metal precursor compound can be a Ni-ligand complex.

In a further aspect, the at least one first ligand can comprise or can be selected from neutral electron donor ligands, and the at least one second ligand can comprise or can be selected from a Lewis basic second ligand, including bidentate ligands and ligands which are more Lewis basic than the first ligand(s). Ligands described as suitable neutral electron donor first ligands or ligands described as suitable Lewis basic second ligands are not intended to be limited to only first ligands and second ligands, respectively, as suitable neutral electron donor first ligands may function as second ligands and suitable Lewis basic second ligands may be used as first ligands. Therefore, in an aspect, any of the ligands disclosed herein may function as a first ligand or may function as a second ligand.

The first or second ligand of the metalalactone and the transition metal precursor compound can be any suitable neutral electron donor ligand or any suitable Lewis base. For instance, the suitable neutral electron donor ligands can include sigma-donor solvents that contain a coordinating atom (or atoms) that can coordinate to the transition metal of the metalalactone (or of the transition metal precursor compound).

Examples of suitable coordinating atoms in the ligands in the first ligand or the second ligand can include, but are not limited to, C, O, N, S, and P, or combinations of these atoms. In some aspects, the first ligand and the second ligand, independently, can be monodentate or bidentate ligand. The bidentate ligands can comprise two coordinating donor atoms that are the same (for example, N,N or P,P) or can comprise two coordinating donor atoms that are different (for example, N,P). In another aspect, the first ligand and the second ligand, independently, can be an acyclic ligand such as (for example, $Et_2O$) or a cyclic ligand (for example, THF).

In an aspect, the first ligand or the second ligand can comprise or be selected from an ether, an organic carbonyl, a thioether, an amine, a nitrile, a phosphine, or an olefin. The first ligand and the second ligand independently can be a monodentate ligand comprising one of these coordinating donor groups or a bidentate ligand comprising two of these coordinating donor groups. In another aspect, the first ligand or the second ligand can be an acyclic ether, a cyclic ether, an acyclic organic carbonyl, a cyclic organic carbonyl, an acyclic thioether, a cyclic thioether, a nitrile, an acyclic amine, a cyclic amine, an acyclic phosphine, a cyclic phosphine, an acyclic olefin, or a cyclic olefin or diolefin. In another aspect, the first ligand can be a diene ligand and the second ligand or the ligand in addition to the metalalactone moiety can be a diphosphine ligand.

Suitable ethers can include, but are not limited to, dimethyl ether, diethyl ether, dipropyl ether, dibutyl ether, methyl ethyl ether, methyl propyl ether, methyl butyl ether, diphenyl ether, ditolyl ether, tetrahydrofuran, 2-methyltetrahydrofuran, 2,5-dimethyltetrahydrofuran, 2,3-dihydrofuran, 2,5-dihydrofuran, furan, benzofuran, isobenzofuran, dibenzofuran, tetrahydropyran, 3,4-dihydro-2H-pyran, 3,6-dihydro-2H-pyran, 2H-pyran, 4H-pyran, 1,3-dioxane, 1,4-dioxane, morpholine, and the like, including substituted derivatives thereof.

Suitable organic carbonyls can include ketones, aldehydes, esters, and amides, either alone or in combination, and illustrative examples can include, but are not limited to, acetone, acetophenone, benzophenone, N,N-dimethylformamide, N,N-dimethylacetamide, methyl acetate, ethyl acetate, and the like, including substituted derivatives thereof.

Suitable thioethers can include, but are not limited to, dimethyl thioether, diethyl thioether, dipropyl thioether, dibutyl thioether, methyl ethyl thioether, methyl propyl thioether, methyl butyl thioether, diphenyl thioether, ditolyl thioether, thiophene, benzothiophene, tetrahydrothiophene, thiane, and the like, including substituted derivatives thereof.

Suitable nitriles can include, but are not limited to, acetonitrile, propionitrile, butyronitrile, benzonitrile, 4-methylbenzonitrile, and the like, including substituted derivatives thereof.

Suitable amines can include, but are not limited to, methyl amine, ethyl amine, propyl amine, butyl amine, dimethyl amine, diethyl amine, dipropyl amine, dibutyl amine, trimethyl amine, triethyl amine, tripropyl amine, tributyl amine, aniline, diphenylamine, triphenylamine, tolylamine, xylylamine, ditolylamine, pyridine, quinoline, pyrrole, indole, 2-methylpyridine, 3-methylpyridine, 4-methylpyridine, 2,5-dimethylpyrrole, 2,5-diethylpyrrole, 2,5-dipropylpyrrole, 2,5-dibutylpyrrole, 2,4-dimethylpyrrole, 2,4-diethylpyrrole, 2,4-dipropylpyrrole, 2,4-dibutylpyrrole, 3,4-dimethylpyrrole, 3,4-diethylpyrrole, 3,4-dipropylpyrrole, 3,4-dibutylpyrrole, 2-methylpyrrole, 2-ethylpyrrole, 2-propylpyrrole, 2-butylpyrrole, 3-methylpyrrole, 3-ethylpyrrole, 3-propylpyrrole, 3-butylpyrrole, 3-ethyl-2,4-dimethylpyrrole, 2,3,4,5-tetramethylpyrrole, 2,3,4,5-tetraethylpyrrole, 2,2'-bipyridine, 1,8-Diazabicyclo[5.4.0]undec-7-ene, di(2-pyridyl)dimethylsilane, N,N,N',N'-tetramethylethylenediamine, 1,10-phenanthroline, 2,9-dimethyl-1,10-phenanthroline, glyoxal-bis(mesityl)-1,2-diimine and the like, including substituted derivatives thereof. Suitable amines can be primary amines, secondary amines, or tertiary amines.

Suitable phosphines and other phosphorus compounds can include, but are not limited to, trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, tricyclohexylphosphine, trimethyl phosphite, triethyl phosphite, tripropyl phosphite, triisopropyl phosphite, tributyl phosphite and tricyclohexyl phosphite, 2-(di-t-butylphosphino)biphenyl, 2-di-t-butylphosphino-1,1'-binaphthyl, 2-(di-t-butylphosphino)-3,6-dimethoxy-2',4',6'-tri-i-propyl-1,1'-biphenyl, 2-di-t-butylphosphino-2'-methylbiphenyl, 2-(di-t- butylphosphinomethyl)pyridine, 2-di-t-butylphosphino-2', 4',6'-tri-i-propyl-1,1'-biphenyl, 2-(dicyclohexylphosphino) biphenyl, (S)-(+)-(3,5-dioxa-4-phospha-cyclohepta[2,1-a;3, 4-a']dinaphthalen-4-yl)dimethylamine, 2-(diphenylphosphino)-2'-methoxy-1,1'-binaphthyl, 1,2,3,4, 5-pentaphenyl-1'-(di-t-butylphosphino)ferrocene, 2,2'-bis (diphenylphosphino)-1,1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(di-t-butyl-phosphino)ethane, 1,2-bis(dicyclohexylphosphino)ethane, 1,3-bis(dicyclohexylphosphino)propane, 1,4-bis(dicyclohexylphosphino)butane, 1,3-bis (diisopropylphosphino)propane, 1,3-bis (diphenylphosphino)propane, 1,3-bis(di-t-butylphosphino) propane, 1,4-bis(diisopropylphosphino)butane, 1,4-bis (diphenylphosphino)butane, 2,2'-bis[bis(3,5-dimethylphenyl)phosphino]-4,4',6,6'-tetramethoxybiphenyl, 2,6-bis(di-t-butylphosphinomethyl)pyridine, 2,2'-bis(dicyclohexylphosphino)-1,1'-biphenyl, bis(2-dicyclohexylphosphinophenyl)ether, 5,5'-bis(diphenylphosphino)-4,4'-bi-1,3-benzodioxole, 2-t-butylphosphinomethylpyridine, bis (diphenylphosphino)ferrocene, bis(diphenylphosphino) methane, bis(dicyclohexylphosphino)methane, bis(di-t-butylphosphino)methane, or TMEDA and the like, including substituted derivatives thereof.

In a further aspect, the first ligand, the second ligand, or the ligand in addition to the metalalactone moiety, independently, can comprise or can be selected from

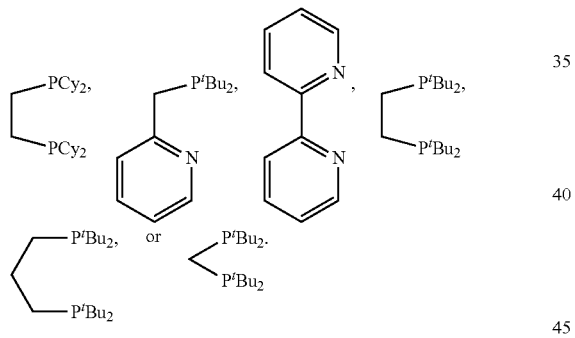

According to another aspect, the first ligand, the second ligand, or the ligand in addition to the metalalactone moiety, independently, can comprise or can be selected from:
(1R,1'R,2S,2'S)-2,2'-Di-tert-butyl-2,3,2',3'-tetrahydro-1H, 1'H-(1,1')biisophosphindolyl (also designated (1R,1'R,2S, 2'S)-DuanPhos or simply DuanPhos in the structures provided herein);
(3S,3'S,4S,4'S,11bS,11'bS)-(+)-4,4'-Di-t-butyl-4,4',5,5'-tetrahydro-3,3'-bi-3H-dinaphtho[2,1-c:1',2'-e]phosphepin (also designated (S)-BINAPINE or simply Binapine in the structures provided herein);
(1S,1S',2R,2R')-1,1'-Di-tert-butyl-(2,2')-diphospholane (also designated (S,S',R,R')-TangPhos or simply TangPhos in the structures provided herein);
(−)-1,2-Bis[(2S,5S)-2,5-diisopropylphospholano]benzene (also designated (S,S)-i-Pr-DUPHOS or simply iPr-DUPHOS in the structures provided herein);
(+)-1,2-Bis[(2R,5R)-2,5-diisopropylphospholano]benzene (also designated (R,R)-i-Pr-DUPHOS);
a racemic mixture of (S,S)-i-Pr-DUPHOS and (R,R)-i-Pr-DUPHOS);
(−)-1,2-Bis[(2S,5S)-2,5-dimethylphospholano]benzene (also designated (S,S)-Me-DUPHOS);
(+)-1,2-Bis[(2R,5R)-2,5-dimethylphospholano]benzene (also designated (R,R)-Me-DUPHOS or simply Me-DUPHOS in the structures provided herein);
A racemic mixture of (S,S)-Me-DUPHOS) and (R,R)-Me-DUPHOS;
(R,R)-(−)-2,3-Bis(tert-butylmethylphosphino)quinoxaline (also designated (R)-QuinoxP or simply QuinoxP in the structures provided herein); or
(R,R)-(+)-1,2-Bis(t-butylmethylphosphino)benzene (also designated (R,R)-BenzP* or simply BenzP* in the structures provided herein).

The structures of the designated ligands are illustrated as follows.

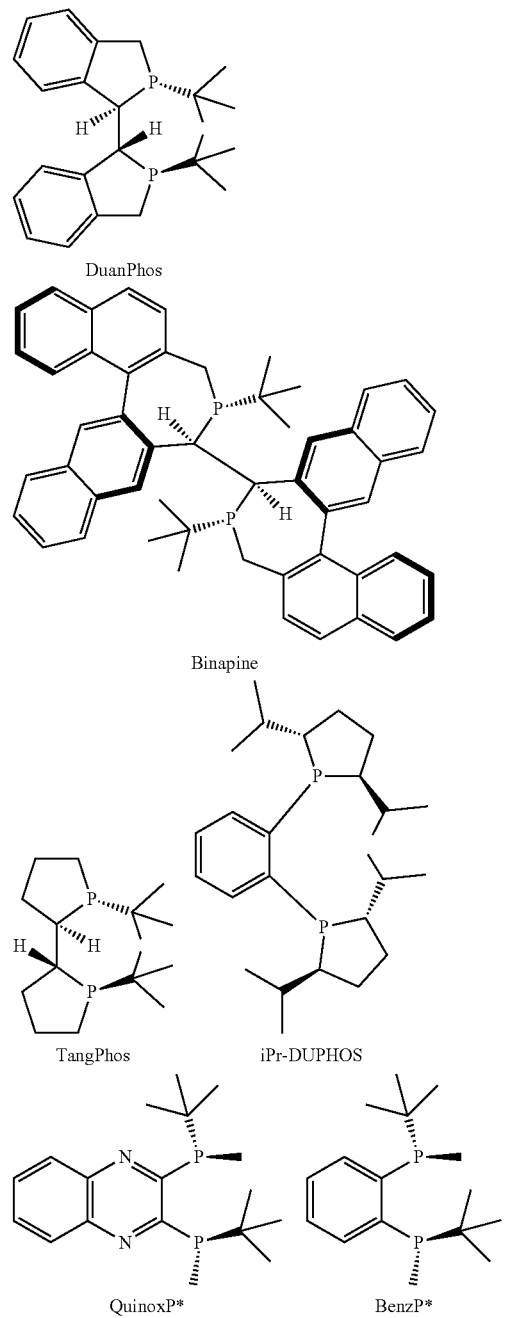

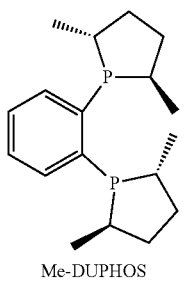

Me-DUPHOS

In other aspects, the first ligand or the second ligand or the metalalactone compound ligand in addition to the metalalactone moiety can be a carbene ligand, for example, a N-heterocyclic carbene (NHC) compound. Representative and non-limiting examples of suitable N-heterocyclic carbene (NHC) materials include the following:

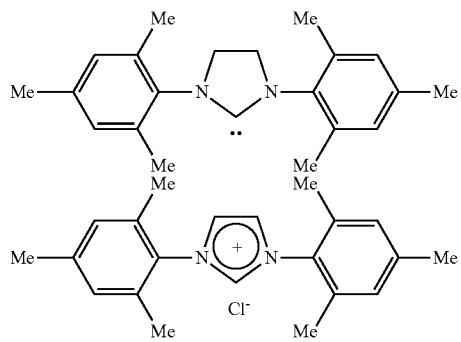

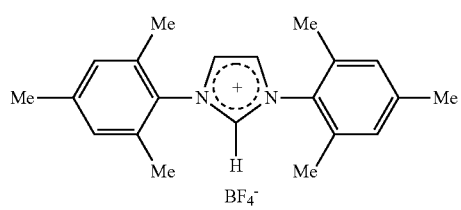

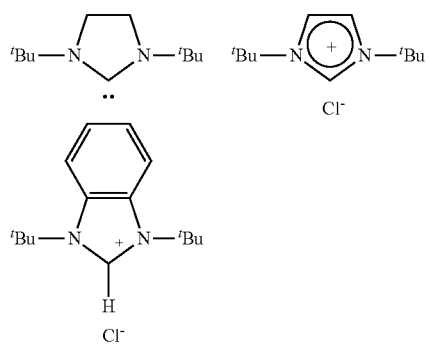

Illustrative and non-limiting examples of metalalactone complexes (representative nickelalactones) suitable for use as described herein include the following compounds (Cy=cyclohexyl, $^t$Bu=tert-butyl):

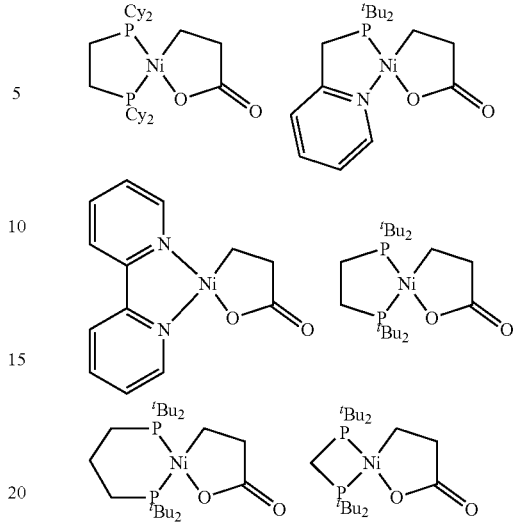

In these nickelalactones, a Group 8-11 transition metal precursor compound comprising at least one first ligand that can be used to prepare a catalyst composition can be $Ni(COD)_2$, and each of the P,P, N,P, and N,N bidentate ligands in addition to the nickelalactone moiety can be the second ligand. When $Ni(COD)_2$ is contacted with ethylene and $CO_2$ in the presence of these P,P, N,P, and N,N bidentate second ligands, the respective metalalactones are formed.

Suitable ligands, transition metal precursor compounds, and metalalactones are not limited solely to those ligands, transition metal precursor compounds, and metalalactones disclosed herein. Other suitable ligands, transition metal precursor compounds, and metalalactones are described, for example, in U.S. Pat. Nos. 7,250,510, 8,642,803, and 8,697,909; Journal of Organometallic Chemistry, 1983, 251, C51-C53; Z. Anorg. Allg. Chem., 1989, 577, 111-114; Journal of Organometallic Chemistry, 2004, 689, 2952-2962; Organometallics, 2004, Vol. 23, 5252-5259; Chem. Commun., 2006, 2510-2512; Organometallics, 2010, Vol. 29, 2199-2202; Chem. Eur. J., 2012, 18, 14017-14025; Organometallics, 2013, 32 (7), 2152-2159; and Chem. Eur. J., 2014, Vol. 20, 11, 3205-3211; the disclosures of which are incorporated herein by reference in their entirety.

The features of the processes disclosed herein (e.g., Group 8-11 transition metal precursor compound, the Group 8-11 metalalactone compound, the first ligand, the second ligand, the ligand in addition to the metalalactone moiety, the diluent, the MT-CMSO of the MT-SO, the $\alpha,\beta$-unsaturated carboxylic acid or the salt thereof, the olefin, and the reaction conditions under which the $\alpha,\beta$-unsaturated carboxylic acid, or a salt thereof, is formed, among others) are independently described, and these features can be combined in any combination to further describe the disclosed processes.

The following references provide information related to the structure and/or activity relationships in the olefin and $CO_2$ coupling process, as observed by changes in phenoxide structure, the phosphine ligand structure, and other ligand structures: Manzini, S.; Huguet, N.; Trapp, O.; Schaub, T. Eur. J. Org. Chem. 2015, 7122; and Al-Ghamdi, M.; Vummaleti, S. V. C.; Falivene, L.; Pasha, F. A.; Beetstra, D. J.; Cavallo, L. Organometallics 2017, 36, 1107-1112. These references are incorporated herein by reference in their entireties.

Process Steps and Conditions

The following aspects explain processes for effecting metalalactone elimination reactions to form an α,β-unsaturated carboxylic acid or a salt thereof is formed, including catalytic processes. Once the Group 8-11 transition metal is deposited on the metal-treated chemically-modified solid oxide or the metal-treated solid oxide and the supported catalyst system is formed, the solid catalyst composition can be isolated and the α,β-unsaturated carboxylic acid or a salt can be formed in the absence of a diluent in a gas phase process as in aspects I and II below, or in the presence of diluent as in aspects III and IV below. Aspects V and VI below are drawn to preparing the catalyst composition.

I. In one aspect, the process for forming an α,β-unsaturated carboxylic acid or a salt thereof can comprise (or consist essentially of, or consist of):
- (a) contacting in any order (i) a Group 8-11 transition metal precursor compound comprising at least one first ligand, (ii) optionally, at least one second ligand, (iii) a first olefin, (iv) carbon dioxide ($CO_2$), (v) a diluent, and (vi) [A] a metal-treated chemically-modified solid oxide, wherein the chemically-modified solid oxide comprises at least one solid oxide which has been treated with at least one electron-withdrawing anion, or [B] a metal-treated solid oxide, to provide a first reaction mixture,
- wherein the contacting is optionally carried out at a total pressure greater than ambient pressure, and
- wherein at least a portion of the Group 8-11 transition metal is deposited on the metal-treated chemically-modified solid oxide or the metal-treated solid oxide;
- (b) releasing the pressure from the first reaction mixture if applicable, and removing the diluent from the first reaction mixture to provide the catalyst composition as a solid catalyst composition; and
- (c) contacting in any order (i) the solid catalyst composition, (ii) a second olefin, and (iii) carbon dioxide ($CO_2$) at a total pressure greater than ambient pressure to provide a second reaction mixture comprising an α,β-unsaturated carboxylic acid or a salt thereof.

In this aspect, the first reaction mixture or the second reaction mixture, independently, can comprise a metalalactone.

II. In a further aspect, the process for forming an α,β-unsaturated carboxylic acid or a salt thereof can comprise (or consist essentially of, or consist of):
- (a) contacting in any order (i) a Group 8-11 transition metal metalalactone compound comprising a metalalactone moiety and at least one ligand in addition to the metalalactone moiety, (ii) a first olefin, (iii) carbon dioxide ($CO_2$), (iv) a diluent, and (v) [A] a metal-treated chemically-modified solid oxide, wherein the chemically-modified solid oxide comprises at least one solid oxide which has been treated with at least one electron-withdrawing anion, or [B] a metal-treated solid oxide, to provide a first reaction mixture,
- wherein the contacting is optionally carried out at a total pressure greater than ambient pressure, and
- wherein at least a portion of the Group 8-11 transition metal metalalactone compound is deposited on the metal-treated chemically-modified solid oxide or the metal-treated solid oxide;
- (b) releasing the pressure from the first reaction mixture if applicable, and removing the diluent from the first reaction mixture to provide the catalyst composition as a solid catalyst composition; and
- (c) contacting in any order (i) the solid catalyst composition, (ii) the second olefin, and (iii) carbon dioxide ($CO_2$) at a total pressure greater than ambient pressure to provide a second reaction mixture comprising an α,β-unsaturated carboxylic acid or a salt thereof.

According to the processes I and II, pressure cycling can be used to rejuvenate the catalyst and produce additional acrylate, and this pressure cycling can be carried out a large number of times. For example, the above aspects I and II can further comprising the steps of:
- (d) releasing at least a fraction of the total pressure from the second reaction mixture; and
- (e) contacting in any order (i) the solid catalyst composition, (ii) the second olefin, and (iii) carbon dioxide ($CO_2$) at a total pressure greater than ambient pressure to provide a subsequent reaction mixture comprising an α,β-unsaturated carboxylic acid or a salt thereof.

When processes I and II are carried out with the additional pressure cycling steps (d) and (e), the processes can further comprise the step of:
- (f) repeating steps (d) and (e) any number of times, for example from 1 to 30 times, to provide further subsequent reaction mixtures comprising the α,β-unsaturated carboxylic acid or a salt thereof.

Also according to processes I and II, in each occurrence, the step of contacting the solid catalyst composition, the second olefin, and carbon dioxide ($CO_2$) independently can be carried out in the substantial absence of a diluent other than the second olefin and carbon dioxide, and wherein in the substantial absence of a diluent (a) the solid catalyst composition resulting from removing the diluent from the first reaction mixture comprises less than 10 wt. %, less than 5 wt. %, less than 1 wt. %, or less than 0.5 wt. % diluent and/or (b) the solid catalyst composition comprises a free-flowing solid. Alternatively, the step of contacting the solid catalyst composition, the second olefin, and carbon dioxide ($CO_2$) independently can be carried out in the presence of a diluent, which is further described in aspects III and IV below.

III. According to yet another aspect, there is provided a process for forming an α,β-unsaturated carboxylic acid or a salt thereof, which utilizes a pressure cycling strategy in the presence of a diluent, as follows. In this aspect, the process can comprise (or consist essentially of, or consist of):
- (a) contacting in any order (i) a Group 8-11 transition metal precursor compound comprising at least one first ligand, (ii) optionally, at least one second ligand, (iii) a first olefin, (iv) carbon dioxide ($CO_2$), (v) a diluent, and (vi) [A] a metal-treated chemically-modified solid oxide, wherein the chemically-modified solid oxide comprises at least one solid oxide which has been treated with at least one electron-withdrawing anion, or [B] a metal-treated solid oxide, to provide a first reaction mixture;
- (b) pressurizing the first reaction mixture with carbon dioxide ($CO_2$) and, if applicable, the first olefin to a total pressure greater than ambient pressure to produce an α,β-unsaturated carboxylic acid or a salt thereof;
- (c) releasing at least a fraction of the total pressure from the first reaction mixture to provide a second reaction mixture; and
- (d) repressurizing the second reaction mixture with carbon dioxide ($CO_2$) and, if applicable, the first olefin to a total pressure greater than ambient pressure to produce additional α,β-unsaturated carboxylic acid or a salt thereof.

IV. In a further aspect regarding the process for forming an α,β-unsaturated carboxylic acid or a salt thereof utilizing the pressure cycling strategy in the presence of a diluent, the process can comprise (or consist essentially of, or consist of):

(a) contacting in any order (i) a Group 8-11 transition metal metalalactone compound comprising a metalalactone moiety and at least one ligand in addition to the metalalactone moiety, (ii) a first olefin, (iii) carbon dioxide ($CO_2$), (iv) a diluent, and (v) [A] a metal-treated chemically-modified solid oxide, wherein the chemically-modified solid oxide comprises at least one solid oxide which has been treated with at least one electron-withdrawing anion, or [B] a metal-treated solid oxide to provide a first reaction mixture;

(b) pressurizing the first reaction mixture with carbon dioxide ($CO_2$) and, if applicable, the first olefin to a total pressure greater than ambient pressure to produce an α,β-unsaturated carboxylic acid or a salt thereof;

(c) releasing at least a fraction of the total pressure from the first reaction mixture to provide a second reaction mixture; and (d) repressurizing the second reaction mixture with carbon dioxide ($CO_2$) and, if applicable, the first olefin to a total pressure greater than ambient pressure to produce additional α,β-unsaturated carboxylic acid or a salt thereof.

According to processes III and IV set out here, the pressure cycling also can rejuvenate the catalyst and produce additional acrylate, and this pressure cycling can be carried out a large number of times. For example, the above aspects III and IV can further comprising the steps of:

(e) releasing at least a fraction of the total pressure from the second reaction mixture to provide a subsequent reaction mixture; and (f) repressurizing the subsequent reaction mixture with carbon dioxide ($CO_2$) and, if applicable, the first olefin to a total pressure greater than ambient pressure to produce additional α,β-unsaturated carboxylic acid or a salt thereof.

Moreover, these processes III and IV with additional steps (e) and (f) can further comprise the step of:

(g) repeating steps (e) and (f) any number of times, for example from 1 to 30 times, to provide further subsequent reaction mixtures and to produce the α,β-unsaturated carboxylic acid or a salt thereof.

V. In a further aspect, there is provided a process for preparing the catalyst composition that can be used to form an α,β-unsaturated carboxylic acid or a salt thereof, and this process can comprise (or consist essentially of, or consist of) contacting in any order:

(i) a Group 8-11 transition metal precursor compound comprising at least one first ligand;

(ii) optionally, at least one second ligand;

(iii) a first olefin;

(iv) carbon dioxide ($CO_2$);

(v) a diluent; and (vi) [A] a metal-treated chemically-modified solid oxide (MT-CMSO), wherein the chemically-modified solid oxide comprises at least one solid oxide which has been treated with at least one electron-withdrawing anion or [B] a metal-treated solid oxide (MT-SO), to provide a first reaction mixture;

wherein the contacting is optionally carried out at a total pressure greater than ambient pressure; and wherein at least a portion of the Group 8-11 transition metal is deposited on the metal-treated chemically-modified solid oxide or the metal-treated solid oxide to provide a catalyst composition.

The first reaction mixture can comprise a metalalactone, and the first reaction mixture can comprise an adduct of a metalalactone and the MT-CMSO or the MT-SO. However this process for preparing the catalyst composition may also start with a metalalactone compound as follows.

VI. In still a further aspect, regarding a process for preparing the catalyst composition that can be used to form an α,β-unsaturated carboxylic acid or a salt thereof, this process can comprise (or consist essentially of, or consist of) contacting in any order:

(i) a metalalactone compound comprising a Group 8-11 transition metal, a metalalactone moiety, and at least one ligand in addition to the metalalactone moiety;

(ii) a first olefin;

(iii) carbon dioxide ($CO_2$);

(iv) a diluent; and (v) [A] a metal-treated chemically-modified solid oxide, wherein the chemically-modified solid oxide comprises at least one solid oxide which has been treated with at least one electron-withdrawing anion or [B] a metal-treated solid oxide, to provide a first reaction mixture;

wherein the contacting is optionally carried out at a total pressure greater than ambient pressure, and wherein at least a portion of the Group 8-11 transition metal is deposited on the metal-treated chemically-modified solid oxide or the metal-treated solid oxide to provide a catalyst composition.

Suitable transition metal precursor compounds, metalalactone compounds, olefins, diluents, solid oxides, MT-CMSO and MT-SO for these aspects I through VI are discussed hereinabove.

Any suitable reactor, vessel, or container can be used to in the first contacting step to form the catalyst composition from the transition metal precursor compound or the metalalactone compound, and any suitable reactor, vessel, or container can be used to in the second contacting step to form the α,β-unsaturated carboxylic acid or a salt thereof. In an aspect, the first contacting step to form the catalyst composition and the second contacting step to form the α,β-unsaturated carboxylic acid or salt can be carried out in the same reaction vessel or in different reaction vessels. Non-limiting examples of suitable reactors, vessels, or containers can include a flow reactor, a continuous reactor, a fixed bed reactor, a moving reactor bed, a stirred bed reactor, a spinning catalyst basket reactor, a stationary catalyst basket reactor, a bubbling bed reactor, and a stirred tank reactor, including more than one reactor in series or in parallel, and including any combination of reactor types and arrangements.

In particular aspects consistent with this disclosure, the metalalactone and the diluent can contact a fixed bed of the MT-CMSO or MT-SO, for instance, in a suitable vessel, such as in a continuous fixed bed reactor. In other aspects, consistent with this disclosure, the metalalactone and the diluent can contact a moving bed of the MT-CMSO or MT-SO, for instance, in a suitable vessel, such as in a moving reactor bed, a stirred bed reactor, or a bubbling bed reactor. In further aspects, combinations of more than one MT-CMSO or more than one MT-SO can be used, such as a mixed bed of a first MT-CMSO and a second MT-CMSO, or sequential beds of a first MT-CMSO and a second MT-CMSO. Similarly, a combination or mixed bed of a first MT-SO and a second MT-SO, or sequential beds of a first MT-SO and a second MT-SO can be used. In a further aspect, a combination or mixed bed of a first MT-CMSO and a second MT-SO, or a first MT-SO and a second MT-CMSO can be used.

In still further aspects, the MT-CMSO or MT-SO of any contacting step can be arranged as a fixed bed, a bubbling bed, a moving bed, or a stirred bed. In an aspect, the feed stream can flow upward or downward through the fixed bed. For instance, the metalalactone and the diluent can contact the first MT-CMSO or MT-SO and then the second MT-CMSO or MT-SO in a downward flow orientation, and the reverse in an upward flow orientation. In a different aspect, the metalalactone and the MT-CMSO or MT-SO can be contacted by mixing or stirring in the diluent, for instance, in a suitable vessel, such as a stirred tank reactor.

In the process for producing an $\alpha,\beta$-unsaturated carboxylic acid or a salt thereof, it is believed that an adduct of the metalalactone and the MT-CMSO or MT-SO forms wherein the MT-CMSO or MT-SO comprises associated metal cations from the metal-containing base. Without intending to be bound by theory, there is some interaction between the metalalactone and the MT-CMSO or MT-SO and its associated metal cations that are believed to destabilize the metalalactone for its elimination of the metal acrylate. This interaction can be referred to generally as an adduct of the metalalactone and MT-CMSO or MT-SO or an adduct of the $\alpha,\beta$-unsaturated carboxylic acid with the MT-CMSO or MT-SO. This adduct can contain all or a portion of the $\alpha,\beta$-unsaturated carboxylic acid and can be inclusive of salts of the $\alpha,\beta$-unsaturated carboxylic acid.

Accordingly, applying reaction conditions to the reaction mixture suitable to form an $\alpha,\beta$-unsaturated carboxylic acid or a salt thereof is intended to reflect any concomitant or subsequent conditions which release the $\alpha,\beta$-unsaturated carboxylic acid or a salt thereof from the adduct, regardless of the specific nature of the adduct.

For example, the process of applying reaction conditions to the reaction mixture suitable to form an $\alpha,\beta$-unsaturated carboxylic acid or a salt thereof, the adduct of the metalalactone and the MT-CMSO or MT-SO and its associated metal cations as defined herein is subjected to some chemical or other conditions or treatment to produce the $\alpha,\beta$-unsaturated carboxylic acid or its salt. Various methods can be used to liberate the $\alpha,\beta$-unsaturated carboxylic acid or its salt, from the MT-CMSO or MT-SO. In one aspect, for instance, the treating step can comprise contacting the adduct of the metalalactone and the MT-CMSO or MT-SO and its associated metal cations with an acid. Representative and non-limiting examples of suitable acids can include HCl, acetic acid, and the like, as well as combinations thereof. In another aspect, the treating step can comprise contacting the adduct of the metalalactone and the MT-CMSO or MT-SO and its associated metal cations with a base, particularly a metal-containing base. Representative and non-limiting examples of suitable bases can include carbonates (e.g., $Na_2CO_3$, $Cs_2CO_3$, $MgCO_3$), hydroxides (e.g., $Mg(OH)_2$, $Na(OH)$, alkoxides (e.g., $Al(O^iPr)_3$, $Na(O^tBu)$, $Mg(OEt)_2$), and the like, as well as combinations thereof ($^iPr$=isopropyl, $^tBu$=tert-butyl, Et=ethyl). In yet another aspect, the treating step can comprise contacting the adduct of the metalalactone and the MT-CMSO or MT-SO and its associated metal cations with a suitable solvent. Representative and non-limiting examples of suitable solvents can include carbonyl-containing solvents such as ketones, esters, amides, etc. (e.g., acetone, ethyl acetate, N,N-dimethylformamide, etc., as described herein above), alcohol solvents, water, and the like, as well as combinations thereof.

In still another aspect, the deposition conditions, the coupling conditions, or both can comprise heating the adduct of the metalalactone and the MT-CMSO or MT-SO and its associated metal cations to any suitable temperature. This temperature can be to or at any suitable temperature, such as for example to or at any temperature within a range of from 5° C. to 750° C., from 10° C. to 500° C., from 15° C. to 200° C., from 20° C. to 100° C., from 25° C. to 75° C., from 25° C. to 50° C., or the like. Higher temperatures can be used if desired. The duration of this heating step is not limited to any particular period of time, as long of the period of time is sufficient to effect the deposition, the coupling, or both, for example, to liberate the $\alpha,\beta$-unsaturated carboxylic acid from the MT-CMSO or MT-SO. As those of skill in the art recognize, the appropriate temperature depends upon several factors, such as the particular diluent used in the process, and the particular MT-CMSO or MT-SO used in the process, amongst other considerations. One further treatment step can comprise, for example, a workup step with additional olefin to displace an alkene-bound nickel acrylate.

In these processes for performing a metalalactone elimination reaction and for producing an $\alpha,\beta$-unsaturated carboxylic acid (or a salt thereof), additional process steps can be conducted before, during, and/or after any of the steps described herein. As an example, these processes can further comprise a step (e.g., prior to step a)) of contacting a transition metal precursor compound with an olefin and carbon dioxide to form the metalalactone. Transition metal precursor compound are described hereinabove. Illustrative and non-limiting examples of suitable olefins can include ethylene, propylene, butene (e.g., 1-butene), pentene, hexene (e.g., 1-hexene), heptane, octene (e.g., 1-octene), and styrene and the like, as well as combinations thereof.

In aspects of the processes that utilize a transition metal precursor compound comprising at least one first ligand, the olefin can be ethylene, and the step of contacting a transition metal precursor compound with an olefin and carbon dioxide ($CO_2$) can be conducted using any suitable pressure of ethylene, or any pressure of ethylene disclosed herein, e.g., from 5 psig (34 KPa) to 1,000 psig (6,895 KPa), from 15 psig (103 KPa) to 500 psig (3,447 KPa), from 25 psig (172 KPa) to 250 psig (1,724 KPa), or from 50 psig (345 KPa) to 150 psig (1,034 KPa), and the like. Further, the olefin can be ethylene, and the step of contacting a transition metal precursor compound with an olefin and carbon dioxide ($CO_2$) can be conducted using a constant addition of the olefin, a constant addition of carbon dioxide, or a constant addition of both the olefin and carbon dioxide, to provide the reaction mixture. By way of example, in a process wherein the ethylene and carbon dioxide ($CO_2$) are constantly added, the process can utilize an ethylene:$CO_2$ molar ratio of from 5:1 to 1:5, from 3:1 to 1:3, from 2:1 to 1:2, or about 1:1, to provide the reaction mixture.

According to a further aspect of the above processes that utilizes a transition metal precursor compound or a metalalactone compound, the process can include the step of contacting a transition metal precursor compound with an olefin and carbon dioxide ($CO_2$) conducted using any suitable pressure of $CO_2$, or any pressure of $CO_2$ disclosed herein, e.g., from 5 psig (34 KPa) to 2,000 psig (13,790 KPa), from 15 psig (103 KPa) to 750 psig (5,171 KPa), from 25 psig (172 KPa) to 250 psig (1,724 KPa), or from 50 psig (345 KPa) to 150 psig (1,034 KPa), and the like. In any of the processes disclosed herein, the processes can further comprise a step of monitoring the concentration of at least one reaction mixture component, at least one elimination reaction product, or a combination thereof, for any reason, such as to adjust process parameters in real time, to determine extent or reaction, or to stop the reaction at the desired point.

According to a further aspect of the above processes that utilizes a transition metal precursor compound or a metalalactone compound, the process can include the step of contacting a transition metal precursor compound with an olefin and carbon dioxide ($CO_2$) conducted using a range of total pressures. When the olefin is ethylene, the ethylene and the $CO_2$ can have different partial pressures or the same partial pressures. In an aspect, for example, in the process for preparing a catalyst composition or the process for producing an α,β-unsaturated carboxylic acid or a salt thereof, the deposition conditions and the coupling conditions, independently, can include pressurizing the first reaction mixture or the second reaction mixture to a total pressure of carbon dioxide ($CO_2$) and the first olefin such as ethylene to or at any suitable total pressure, such as, for example, from 5 (34 KPa) to 3,000 psig (20,684 KPa), from 15 (103 KPa) to 1,500 psig (10,342 KPa), from 25 (172 KPa) to 750 psig (5,171 KPa), from 50 (345 KPa) to 500 psig (3,447 KPa), or from 75 (34 KPa) to 250 psig (1,723 KPa), and the like.

As illustrated, this process that utilizes a transition metal precursor compound comprising at least one first ligand includes one aspect in which no second ligand is employed in the contacting step, and another aspect in which a second ligand is used in the contacting step. That is, one aspect involves the contacting step of the process comprising contacting the transition metal precursor compound comprising at least one first ligand with the at least one second ligand. The order of contacting can be varied. For example, the contacting step of the process disclosed above can comprise contacting 1) the transition metal precursor compound comprising at least one first ligand with 2) the at least one second ligand to form a pre-contacted mixture, followed by contacting the pre-contacted mixture with the remaining components 3)-6) in any order to provide the reaction mixture.

Further embodiments related to the order of contacting, for example, the contacting step can include or comprise contacting the metalalactone, the diluent, and the MT-CMSO or MT-SO in any order. The contacting step can also comprise contacting the metalalactone and the diluent to form a first mixture, followed by contacting the first mixture with the MT-CMSO or MT-SO to form the reaction mixture. In a further aspect, the contacting step can comprise contacting the diluent and the MT-CMSO or MT-SO to form a first mixture, followed by contacting the first mixture with the metalalactone to form the reaction mixture. In yet a further aspect, the contacting step of the process further comprises contacting any number of additives, for example, additives that can be selected from an acid, a base, or a reductant.

Suitable transition metal precursors, first ligands, second ligands, olefins, diluents, MT-CMSOs or MT-SOs with the associated metal cations are disclosed hereinabove. In some aspects, the contacting step—step (a)—of this process can include contacting, in any order, the transition metal-ligand, the olefin, the diluent, the MT-CMSO or MT-SO, and carbon dioxide, and additional unrecited materials. In other aspects, the contacting step can consist essentially of, or consist of, contacting, in any order, the transition metal-ligand, the olefin, the diluent, the MT-CMSO or MT-SO, and carbon dioxide. Likewise, additional materials or features can be employed in the forming step of step b) of this process. Further, it is contemplated that this processes for producing an α,β-unsaturated carboxylic acid, or a salt thereof, can employ more than one transition metal-ligand complex and/or more than one MT-CMSO or MT-SO (or a combination of an MT-CMSO and an MT-SO) if desired and/or more than one olefin. Additionally, a mixture or combination of two or more diluents can be employed.

As above, any suitable reactor, vessel, or container can be used to contact the transition metal precursors, first ligands, second ligands, olefin, diluent, MT-CMSO or MT-SO, and carbon dioxide, whether using a fixed bed of the MT-CMSO or MT-SO, a stirred tank for contacting (or mixing), or some other reactor configuration and process. While not wishing to be bound by the following theory, a proposed and illustrative reaction scheme for this process is provided below as Scheme 2.

Scheme 2

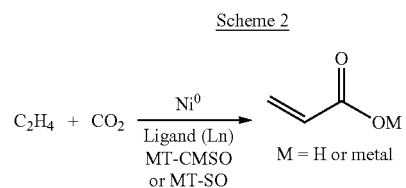

Independently, the contacting and forming steps of any of the processes disclosed herein (i.e., for performing a metalalactone elimination reaction, for producing an α,β-unsaturated carboxylic acid, or a salt thereof), can be conducted at a variety of temperatures, pressures, and time periods. For instance, the temperature at which the components in step a) are initially contacted can be the same as, or different from, the temperature at which the forming step b) is performed. As an illustrative example, in the contacting step, the components can be contacted initially at temperature T1 and, after this initial combining, the temperature can be increased to a temperature T2 for the forming step (e.g., to form the α,β-unsaturated carboxylic acid, or the salt thereof). Likewise, the pressure can be different in the contacting step and the forming step. Often, the time period in the contacting step can be referred to as the contact time, while the time period in forming step can be referred to as the reaction time. The contact time and the reaction time can be, and often are, different.

In an aspect, the contacting step and/or the forming step of the processes disclosed herein can be conducted at a temperature in a range from 0° C. to 250° C.; alternatively, from 20° C. to 200° C.; alternatively, from 0° C. to 95° C.; alternatively, from 10° C. to 75° C.; alternatively, from 20° C. to 50° C.; or alternatively, from 15° C. to 70° C., or alternatively, from 25° C. to 75° C. In these and other aspects, after the initial contacting, the temperature can be changed, if desired, to another temperature for the forming step. These temperature ranges also are meant to encompass circumstances where the contacting step and/or the forming step can be conducted at a series of different temperatures, instead of at a single fixed temperature, falling within the respective ranges.

In an aspect, any contacting step and/or the forming step of the processes disclosed herein can be conducted at a total pressure in a range of, for example, from 5 (34 KPa) to 5,000 psig (34,474 KPa), such as from 5 psig (34 KPa) to 2500 psig (17,237 KPa). In some aspects, the total pressure can be in a range from 5 psig (34 KPa) to 500 psig (3,447 KPa); alternatively, from 25 psig (172 KPa) to 3000 psig (20,684

KPa); alternatively, from 45 psig (310 KPa) to 1000 psig (6,895 KPa); or alternatively, from 50 psig (345 KPa) to 250 psig (1,724 KPa).

In another aspect, the processes disclosed herein can be conducted at a transition metal (catalyst) concentration of less than about 0.2 mM. Although the reaction works at higher concentrations, it has been discovered that at catalyst concentrations of less than about 0.2 mM, the acrylate yield (and turnover number) increase relative to the acrylate yield and turnover number of the 0.2 mM concentration processes, when conducted under otherwise similar or identical conditions. For example, the metalalactone or the transition metal precursor compound can be present in the reaction mixture at a concentration of less than about 0.18 mM (millimolar), less than about 0.15 mM, less than about 0.10 mM, less than about 0.05 mM, less than about 0.02 mM, less than about 0.015 mM, less than about 0.010 mM, less than about 0.005 mM, or less than about 0.002 mM. In these processes, the lower end of the catalyst concentration can be about 0.0001 mM, about 0.0002 mM, about 0.0005 mM, or about 0.001 mM.

The contacting step of the processes is not limited to any particular duration of time. That is, the respective components can be initially contacted rapidly, or over a longer period of time, before commencing the forming step. Hence, the contacting step can be conducted, for example, in a time period ranging from as little as 1-30 seconds to as long as 1-12 hours, or more. In non-continuous or batch operations, the appropriate reaction time for the forming step can depend upon, for example, the reaction temperature, the reaction pressure, and the ratios of the respective components in the contacting step, among other variables. Generally, however, the forming step can occur over a time period that can be in a range from 1 minute to 96 hours, such as, for example, from 2 minutes to 96 hours, from 5 minutes to 72 hours, from 10 minutes to 72 hours, or from 15 minutes to 48 hours.

If the process employed is a continuous process in a diluent, then the metalalactone and MT-CMSO and catalyst contact and reaction time (or the transition metal precursors, first ligands, second ligands, olefin, diluent, MT-CMSO or MT-SO, and carbon dioxide contact/reaction time) can be expressed in terms of weight hourly space velocity (WHSV), which is the ratio of (a) the weight of the metalalactone-containing solution or transition metal-containing solution which contains all the components of the catalysis except for the solid MT-CMSO or MT-SO to (b) the weight of MT-CMSO or MT-SO which that solution contacts in the continuous process, per unit time (for example, $hr^{-1}$). The weight of the metalalactone-containing solution or transition metal-containing solution includes the combined weights of the metalalactone or transition metal precursor compound, first ligands, second ligands, olefin, diluent, carbon dioxide, and anything else in the solution. While not limited thereto, the WHSV employed, based on the amount of the MT-CMSO or MT-SO, can be in a range from 0.05 to 100 $hr^{-1}$, from 0.05 to 50 $hr^{-1}$, from 0.075 to 50 $hr^{-1}$, from 0.1 to 25 $hr^{-1}$, from 0.5 to 10 $hr^{-1}$, from 1 to 25 $hr^{-1}$, or from 1 to 5 $hr^{-1}$.

In the processes disclosed herein, the molar yield of the $\alpha,\beta$-unsaturated carboxylic acid, or the salt thereof), based on the metalalactone (or the metal precursors) is at least 2%, and more often can be at least 5%, at least 10%, or at least 15%. In particular aspects of this disclosure, the molar yield can be at least 18%, at least 20%, at least 25%, at least 35%, at least 50%, at least 60%, at least 75%, or at least 85%, or at least 90%, or at least 95%, or at least 100%. That is, catalytic formation of the $\alpha,\beta$-unsaturated carboxylic acid or the salt thereof can be effected with the disclosed system. For example, the molar yield of the $\alpha,\beta$-unsaturated carboxylic acid, or the salt thereof, based on the metalalactone or based on the transition metal precursor compound can be at least 20%, at least 40%, at least 60%, at least 80%, at least 100%, at least 120%, at least 140%, at least 160%, at least 180%, at least 200%, at least 250%, at least 300%, at least 350%, at least 400%, at least 450%, at least 500%, at least 600%, at least 700%, at least 800%, at least 900%, at least 1000%, at least 1250%, at least 1500%, at least 1750%, at least 2000%, at least 2500%, at least 3000%, at least 3500%, at least 4000%, at least 5000%, or even greater.

The specific $\alpha,\beta$-unsaturated carboxylic acid (or salt thereof) that can be formed or produced using the processes of this disclosure is not particularly limited. Illustrative and non-limiting examples of the $\alpha,\beta$-unsaturated carboxylic acid can include acrylic acid, methacrylic acid, 2-ethylacrylic acid, cinnamic acid, and the like, as well as combinations thereof. Illustrative and non-limiting examples of the salt of the $\alpha,\beta$-unsaturated carboxylic acid can include sodium acrylate, potassium acrylate, magnesium acrylate, sodium (meth)acrylate, and the like, as well as combinations thereof.

Once formed, the $\alpha,\beta$-unsaturated carboxylic acid (or the salt thereof) can be purified and/or isolated and/or separated using suitable techniques which can include, but are not limited to, evaporation, distillation, chromatography, crystallization, extraction, washing, decanting, filtering, drying, and the like, including combinations of more than one of these techniques. In an aspect, the process for performing a metalalactone elimination reaction (or the process for producing an $\alpha,\beta$-unsaturated carboxylic acid, or a salt thereof) can further comprise a step of separating or isolating the $\alpha,\beta$-unsaturated carboxylic acid (or the salt thereof) from other components, e.g., the diluent and the MT-CMSO.

EXAMPLES

The invention is further illustrated by the following examples, which are not to be construed in any way as imposing limitations upon the scope of this invention. Various other aspects, embodiments, modifications, and equivalents thereof which, after reading the description herein, can suggest themselves to one of ordinary skill in the art without departing from the spirit of the present invention or the scope of the appended claims.

The general experimental and spectroscopic details and calculation methods are provided below. Some additional aspects of the experimental conditions, methods, and tests can be found in the following patents and applications by the Applicant, each of which is incorporated herein by reference in its entirety: U.S. Pat. Nos. 10,160,711; 10,392,336; 10,544,080; and 10,550,061.

A. Preparation of Various Metal-Treated Chemically-Modified Solid Oxide Activators Abbreviations. The specific MT-CMSO abbreviated "S-SSA" is sulfated alumina, and the specific MT-CMSO abbreviated "M-SSA" is fluorided silica-coated alumina. According to this disclosure, the CMSO is metal-treated using, for example, sodium tert-butoxide (NaO-t-Bu) or potassium tert-butoxide (KO-t-Bu) to form the metal-treated activators described herein. The following examples primarily employ sodium tert-butoxide sulfated alumina, which is abbreviated Na—S-SSA or S-SSA-Na, although any of the disclosed MT-CMSO can be used in these reactions. Other representative preparations of some of the metal-treated chemically-modified solid oxides are disclosed in U.S. Pat. No. 9,725,393, which is incorporated herein in its entirety.

Unless otherwise indicated, the nickelalactone comprising a bis(dicyclohexyl-phosphino)ethane ligand, ($C_6H_{11}$)$_2PCH_2CH_2P(C_6H_{11})_2$), was used in the catalytic runs. Using the same metalalactone removed any variability due to the nickel catalyst. The bis(dicyclohexyl-phosphino)ethane ligand is abbreviated "dcpe", therefore the nickelalactone is (dcpe)Ni(OC(O)$CH_2CH_2$), where the —OC(O)$CH_2CH_2$— ligand forms a metalacyclic structure with the nickel. This nickelalactone is abbreviated (dcpe)NiLac, where the "Lac" is shorthand for the —OC(O)$CH_2CH_2$— moiety forming the metalalactone.

Sulfated Alumina (S-SSA). Alumina was mixed with a solution of sulfuric acid in methanol, to result in approximately 15 wt. % (weight percent) sulfate based on the weight of the sulfated alumina. After drying under vacuum at 110° C. overnight, the dried powder was calcined at 600° C. in dry air for three hours. After being allowed to cool to ambient temperature, the resulting sulfated alumina (S-SSA) was used to prepare the metal-treated sulfated alumina.

Fluorided Silica-Coated Alumina (Mullite) (M-SSA). The fluorided silica-coated alumina SSA was prepared by first contacting alumina with tetraethylorthosilicate in isopropanol to equal 25 wt. % $SiO_2$. After drying, the silica-coated alumina was calcined at 600° C. for 3 hours, and then allowed to cool to ambient temperature. The fluorided silica-coated alumina (7 wt. % F) was prepared by impregnating the calcined silica-coated alumina with an ammonium bifluoride solution in methanol, drying the resulting solid, and then calcining at 600° C. for 3 hours. After being allowed to cool to ambient temperature, the resulting fluorided silica-coated alumina (M-SSA) was used to prepare the metal-treated fluorided silica-coated alumina.

Sodium-Treated Sulfated Alumina (NaO-t-Bu on S-SSA). The sulfated alumina (S-SSA) prepared as above (4.2 g) and sodium tert-butoxide (2 g) were combined in 60 mL of toluene, forming a yellow suspension. This mixture was stirred at ambient temperature for 18 hours, the solid was filtered off and washed with 10 mL of toluene, forming the colorless solid of sodium-treated sulfated alumina (Na—S-SSA).

Sodium-Treated Fluorided Silica-Coated Alumina (NaO-t-Bu on M-SSA). Fluorided silica-coated alumina (5 g) and sodium tert-butoxide (2 g) were combined in 60 mL of toluene forming a yellow suspension. The mixture was stirred at ambient temperature for 18 hours, the solid was filtered off and washed with 10 mL of toluene, forming the colorless solid of filtered and washed with 10 mL toluene forming a colorless solid of sodium-treated fluorided silica-coated alumina.

Sodium-Treated Sulfated Alumina using a Sodium Salt and an Acid (NaCl/$H_2SO_4$/S-SSA). A metal-treated sulfated alumina (S-SSA), specifically sodium-treated sulfated alumina, can be prepared by the alternative method of treating the S-SSA with the combination of a sodium-containing salt and an acid, as follows. Sulfated alumina (2.5 g) prepared as described above was taken up in 25 mL of water followed by 1 mL of concentrated sulfuric acid. The suspension was left to stir for 30-60 minutes, after which a saturated brine (NaCl) solution (25 mL) was added. After stirring this mixture overnight, the resulting suspension was filtered off, and the collected solid was washed with DI (deionized) water (3×100 mL). The washed solid was dried under vacuum at 60° C. for about 5 hours.

Sodium-treated MCM-41 silica (Na-MCM-41). A 1.5 g sample of mesostructured silica, MCM-41 type (hexagonal), from Aldrich Chemical Company were mixed with 50 mL of distilled water in a 100 mL one neck round bottom flask. The mixture was sonicated for 1 h at room temperature. A 10 mL portion of $NaNO_3$ solution (1.35 g) was added dropwise to the resulting MCM-41 slurry in the flask with stirring, and this mixture was stirred for 24 h at room temperature. After this time, the water was gradually evaporated at 90° C. with slow stirring. The flask containing $NaNO_3$ treated MCM-41 (Na-MCM-41) was left overnight in a vacuum oven for drying and later calcined in a muffle furnace at 550° C. (at a 1° C./min ramp) in flowing air for 5 h.

Sodium-Treated Al-KIT-6 silica (Na/Al-KIT-6). The following one-pot synthesis was used to prepare the Al-KIT-6 catalyst (Si/Al molar ratio=10). A 4.0 g portion of triblock copolymer Pluronic P123 was dissolved in 160 mL of DI water and 6.9 g of 37.1 wt. % HCl at 37±2° C. Then, 4.0 g of 1-butanol was added, and the mixture was stirred for 1 h. Following this step, 8.7 g of TEOS (tetraethyl orthosilicate (TEOS, 98%) is a silica source) and the desired amount (1.245 g) of aluminum nitrate ($Al_2(NO_3)_2 \cdot 9H_2O$, Sigma Aldrich) were added and the stirring continued for 24 h. The resulting mixture was transferred into a Teflon-lined autoclave and heated to 100° C. for 24 h. The solid product was collected and washed by DI water, then dried at 100° C. overnight. The resulting sample was calcined in flowing air at 550° C. for 10 h at a ramp rate of 1° C./min. The calcined solids are termed as Al-KIT-6 (Si/Al=10).

For preparing the sodium treated Al-KIT-6, termed Na/Al-KIT-6 (Na=3%), a wet impregnation procedure was used as follows. The Al-KIT-6 support prepared as described above was placed in an aqueous solution of sodium aluminate (Na$Al_2O_3$) (0.283 g of Na$Al_2O_3$ dissolved in 5 g of DI water), followed by sonication for 0.5 h and stirring of the suspended solid slurry for 24 h at room temperature. The aqueous carrier was evaporated in a rotary evaporator at 45° C. The resulting solid residue was dried at 100° C. overnight in an oven, then calcined in flowing air in a muffle furnace at 550° C. (T ramp rate of 1° C./min) for 5 h, and then allowed to cool to room temperature. The molar Si/Al ratio and Na content in the resulting solid (Na/Al-KIT-6), obtained by XRF analysis, were 10 and 3.3 wt. %, respectively.

B. Experimental Considerations

The overall catalytic system is complex and involves multiple steps in multiple phases. The reaction was typically carried out in a liquid phase containing a solvent (such as THF or toluene) in which the nickel complex was soluble at ambient conditions. The reactants, ethylene ($P_c$=5.07 MPa, $T_c$=9.4° C.) and $CO_2$ ($P_c$=7.3 MPa, $T_c$=31.1° C.) were dissolved in the liquid phase under pressure. Thermodynamic solubility measurements performed in a view cell established conditions for homogenous reaction conditions (that is, without (dcpe)NiLac precipitation) at reaction conditions. The ternary phase equilibria ($CO_2/C_2H_4$/solvent) at various pressures and temperatures were also modeled using AspenPlus® Process Simulation Software, allowing us to rationally choose operating conditions.

C. Catalytic Reactor System and Test Method

The diluent or solvent in the metal-mediated ethylene and carbon dioxide coupling process may function in various roles, for example, the diluent may be a catalyst carrier to transport the Group 8-11 metal catalyst from one metal site on the metal-treated chemically-modified solid oxide to another metal site. As disclosed herein, the metal of the metal-treated chemically-modified solid oxide can comprise or be selected from a Group 1, 2, 12, or 13 metal cation, such as lithium, sodium, potassium, magnesium, calcium, zinc or aluminum cations. For these exemplary embodiments, sodium was the principal metal cation used.

As explained herein, the catalytic formation of acrylic acid or a metal acrylate is catalytic in the Group 8-11 metal catalyst, but stoichiometric in the Group 1, 2, 12, or 13 metal cation as well as ethylene and carbon dioxide. Because the metal-treated chemically-modified solid oxide (MT-CMSO) is a heterogeneous activating support, reliably assessing the activity of the Group 8-11 metal catalyst and the activating support, mass transfer limitations were reduced or minimized to the extent possible using a spinning basket reactor to limit mass transfer or mass transport resistances. These mass transfer resistances are thought to involve (a) a stagnant boundary layer at the solid-liquid interface and (a) pore-diffusion rates of the liquid phase. Therefore, the thickness of the boundary layer was reduced or minimized by stirring while the pore-diffusion path for a given solid could be minimized by reducing the particle size.

Based on these considerations, a spinning basket system which housed the solid activating support was used to conduct the catalytic reactions under pressure, which reduced or minimized to the extent possible mass transfer or boundary layer limitations. A 50 mL PARR® reactor was fitted with twin cylindrical baskets to house the solid particles. Each cylindrical basket was made with a double layer screen of stainless-steel mesh (SS 316, 325×2300 mesh size, 0.0014 inch/0.001 inch wire diameter) to contain the Na—S-SSA solid particles, and two such baskets were mounted to opposite sides of a stirring rod element of the PARR® Reactor, with the cylinder axes parallel to the stirring rod element and to each other. Each twin basket could contain approximately half of the total solid activator of about 700 mg to 800 mg of solid activator. Vigorously stirring the baskets allowed them to function as stirrer blades and reduce or minimize the stagnant boundary layer at the solid-liquid interface, without any visible evidence of solid escaping from the baskets into the liquid phase. Thus, the liquid phase following each run was observed to be clear. For recovering the metal acrylate from the solid phase, the catalytic reaction solvent was replaced with an extraction medium such as water such that subsequent stirring extracted the metal acrylate from the solid into the liquid phase.

D. Turnover Number (TON) and Sodium Conversion Calculation Methods.

For the acrylic acid turnover numbers (TONs) reported herein, the TONs were calculated as follows.

(i) Acrylic Acid/Acrylate TON calculated by Q-NMR (Quantitative NMR) with a sorbic acid standard. Using a sorbic acid internal standard, the TON could be calculated as follows.

$$\text{Moles Sodium Acrylate Produced} = \frac{\text{moles sorbic Acid in Standard}}{1 \text{ g of Standard}} \times$$

$$xg \text{ standard added to } NMR \times \frac{QNMR \text{ moles sodium acrylate}}{QNMR \text{ moles sorbic acid}}$$

$$TON = \frac{\text{moles of sodium acrylate produced}}{\text{moles of nickelalactone in reactor}}$$

(ii) Acrylic Acid/Acrylate TON calculated by gas chromatography (GC). TON could also be calculated using GC as follows. GC data was obtained with an Agilent 6890N GC, with a Flame Ionization Detector and a G4513A auto injector, with 25 m CP-Wax 58 (FFAP) CB Capillary column.

$$\text{Concentration of acrylic acid} = \frac{\text{Acrylic acid peak area}}{\text{calibration response factor}}$$

$$TON = \frac{\text{Moles of acrylic acid}}{\text{Moles of Nickelalactone in Reactor}}$$

(iii) Sodium conversion calculations. The percent sodium conversion could be calculated as set out in the following example using the Na—S-SSA metal-treated chemically-modified solid oxide, which contained 21.5 wt. % Na, using the equivalent relationships shown here.

(i) concentration of production of acrylic acid (mole) =concentration of nickelalactone×TON (ii) 1 mole acrylic acid product needs 1 mole of Na consumption, therefore the number of moles of Na consumption=number of moles of acrylic acid production (iii) weight of Na consumption in the experiment=number of moles of Na consumption÷22.9 (g/mol)

(iv) wt. % of Na consumption=(weight of Na consumption÷weight of Na—S-SSA)×100

(v) Na wt. % in Na—S-SSA=21.5%

(vi) Na conversion (%)=(wt. % of Na consumption÷21.5)×100

Example 1. Benchmark Reactions for Acrylic Acid Formation in the Presence and Absence of a Metal-Treated Chemically-Modified Solid Oxide (a) Reactions absent a metal-treated chemically-modified solid oxide. An initial comparison of the formation of acrylic acid was carried out using the nickelalactone (dcpe)Ni(OC(O)CH$_2$CH$_2$), abbreviated (dcpe)NiLac, in the absence of a metal-treated chemically-modified solid oxide (MT-CMSO), as follows.

A solution of nickelalactone (dcpe)NiLac was prepared under inert atmosphere conditions from 0.049 grams (g) of (dcpe)NiLac (8.85×10$^{-5}$ mole) dissolved in 25 milliliters (mL) of dry THF. A 0.210-g portion of sodium tert-butoxide was dissolved in this mixture, and the mixture was charged to a PARR® reactor, along with 150 psig C$_2$H$_4$ (~1 MPa) and 150 psig CO$_2$ (~1 MPa) at 25° C. This reaction mixture was heated to 40° C. (over about 45 min (minutes)), and the reaction mixture was allowed to proceed for 20 h (hours). Following the 20 h run, the reactor was cooled to room temperature over about 30 min with a cooling fan. The reaction vessel was slowly depressurized to ambient pressure (over 50 min) by releasing the gases gradually to avoid cooling upon rapid expansion.

Because this reaction was carried out in the absence of a MT-CMSO, the sodium acrylate could be extracted from reaction solids by the following extraction procedure. For NMR analysis, the liquid phase from the reaction above containing the sodium tert-butoxide co-catalyst was evaporated to dryness using a rotary evaporator, and the resulting residue was extracted with 10 mL of D$_2$O, and the sodium acrylate content was measured. For a GC analysis, the liquid phase from the reaction above containing the sodium tert-butoxide co-catalyst was evaporated to dryness and the resulting residue was extracted with 10 mL of H$_2$O. The H$_2$O solution was then transferred to a vial, and 0.5 mL of 1 M NaHSO$_4$ solution in THF was added. This THF-diluted sample was used for acrylic acid analysis by GC.

As indicated in Table 1, there was no significant acrylic acid production under these conditions using the nickelalactone (dcpe)NiLac as the catalyst and free sodium tert-butoxide as the co-catalyst at 40° C.

(b) Reactions in the presence of a metal-treated chemically-modified solid oxide. Reactions using a MT-CMSO were conducted using the same reaction conditions (reactants, amounts, temperature, pressure, cooling and depressurization procedures, and the like) as used in the reactions absent the MT-CMSO described above, except for the presence of an added MT-CMSO. In this Example, the reaction used Na—S-SSA solid as the MT-CMSO.

Extraction Procedure A. Following the reaction, the THF liquid phase was separated out and the MT-CMSO solid phase was vacuum dried for 1 h (hour). The solid MT-CMSO was placed in a round bottom flask and extracted using 4.5 mL of deionized (DI) $D_2O$ with stirring for a time period of from about 2 h to about 12 h. The resulting $D_2O$ solution was saved and fresh DI $D_2O$ was added to the vessel to the flask, and the extraction process was repeated for up to 12 times. The $D_2O$ solutions were then transferred to a vial, and 0.5 mL of 1 M $NaHSO_4$ solution in THF was added to acidify the solution. This THF-diluted sample was used for acrylic acid analysis by GC, and the acrylic acid TON was calculated as described above.

The extraction procedure described above using $D_2O$ can be carried out with other extraction solvents. For example, $H_2O$, THF, ethanol, n-propanol, i-propanol, ethyl acetate, and other light, polar solvents are useful for the extraction. Mixtures of these solvents, including an amount of water mixed with smaller amounts of the organic solvents such as mixtures of THF and $H_2O$ work well. While THF and $H_2O$ mixtures can span a wide relative concentration range, THF:$H_2O$ weight ratios of about 15:85, 30:70, or 50:50 have been found to work well.

In this experiment, the TON for acrylic acid formation was low, only 0.8 as shown in Table 1. While not intending to be bound by theory, this low TON is believed to be due to the limited solubility of the nickelalactone (dcpe)NiLac catalyst in THF, when $C_2H_4$ and $CO_2$ are substantially dissolved in the solvent to form a $(C_2H_4+CO_2)$-expanded THF solution. In this case, only the soluble fraction of the nickelalactone complex contributes to acrylate formation, even though TON is calculated based on the total nickelalactone charged to the reactor. Therefore, smaller amounts of nickelalactone complex were used in the subsequent Examples. See for example, Example 2.

TABLE 1

Estimated acrylic acid turnover numbers (TONs) in absence and presence of metal-treated chemically-modified solid oxide, based on total amount of nickelalactone.

| Weight (mole) of (dcpe)NiLac | Co-catalyst | Weight of co-catalyst (g) | Reaction temperature (° C.) | Acrylic acid TON |
|---|---|---|---|---|
| 49 mg (8.85 × $10^{-5}$) | free sodium tert-butoxide | 0.210 | 40-50 | 0 |
| 43 mg (7.85 × $10^{-5}$) | Na—S-SSA | 0.150 | 40 | 0.8 |

Example 2. Acrylate Production with a Nickelalactone Catalyst and a Metal-Treated Chemically-Modified Solid Oxide (MT-CMSO)

The Example 2 catalytic reactions were performed using lower nickelalactone (dcpe)NiLac concentrations as compared to the Example 1 runs in Table 1, in order to ensure complete solubility of the Ni complex in the gas-expanded reaction mixture, as follows. A solution of nickelalactone (dcpe)Ni(OC(O)$CH_2CH_2$), "(dcpe)NiLac", was prepared in an inert atmosphere (under nitrogen) by dissolving a 0.0056 g sample of (dcpe)NiLac (1.01×$10^{-5}$ mole) in 30 mL of dry THF. The twin-basket assembly loaded with Na—S-SSA (~700 mg equally divided between the two baskets) was attached to the stirrer rod of a 50 mL PARR® reactor as described above. The Na—S-SSA was used without any pretreatment. The reactor was sealed and flushed with $N_2$ gas (HP grade, 99.99%) for 15 minutes. A liquid solution containing the nickelalactone was injected into the PARR® reactor via 50 mL airtight syringe, and the nickelalactone solution was stirred at ~300 rpm while the reactor was pressurized first with ethylene (UHP grade, 99.95%; 150 psig partial pressure at 25° C.), followed by pressuring the reactor with $CO_2$ (HP grade, 99.995%; 150 psig partial pressure), each from separate cylinders, for a total pressure of 300 psig at 25° C.

The charged reactor was heated to the desired temperature (40° C.) over approximately 45 minutes. The stirring rate was then increased to 800 rpm signaling the start of reaction. The increased stirring promoted mixing of the pressurized gas and liquid phases as well as enhances the interphase mass transfer rates between the liquid and solid phases. This reaction was run for 20 h, after which the reactor was cooled to room temperature and the reaction vessel was slowly depressurized to ambient pressure.

Extraction Procedure B. Following the reaction, the two baskets were transferred to another 50 mL PARR® reactor to extract the acrylate with water, as follows. A 10 mL portion of DI (deionized) $H_2O$ and 20 mL of THF were added into the reactor used as the extraction vessel and stirred at 800 rpm for 6 h at room temperature for a single extraction cycle. The resulting solution was saved and a fresh mixture of 10 mL of DI $H_2O$ and 20 mL of THF was added to the vessel to repeat the extraction process. This extraction cycle was repeated (about 4-5 times) until no more products were extracted from the basket, as determined from analysis of the liquid phase. The THF was evaporated from the combined liquid phase extract with flowing $N_2$ in approximately 1 h. The remaining liquid (mostly water) was then transferred to a vial, and 0.5 mL of 1 M $NaHSO_4$ solution was added to the remaining liquid in 20 mL vials and stirred for 1 h at 400 rpm. The final mixture was diluted with THF to a total volume of 5 mL. The THF-diluted samples were injected to GC for acrylic acid analysis, and the acrylic acid TON was calculated as described above.

Table 2 summarizes the TON for four repeated runs performed under nearly identical reaction conditions with the same metal-treated chemically-modified solid oxide taken from the same batch (Na—S-SSA).

For the first three runs, acrylic acid was recovered following the conventional procedure for extracting the sodium acrylate from the resins according to Extraction Procedure A, set out in Example 1. For the fourth run, the acrylate was extracted following the Extraction Procedure B, set out above in Example 2. All four results provided consistent TON values of 19±0.9, confirming that the reaction and product collection procedures are reproducible. Further, the TON value based on results from the conventional product extraction procedure of Example 1 is more or less identical to that based on extraction in the PARR® reactor of Example 2. Therefore, the PARR® reactor was used for product extraction in all subsequent experiments.

TABLE 2

Estimated turnover numbers (TONs) with optimized experimental and extraction conditions

| Run No.[A] | Weight (mole) of (dcpe)NiLac | Weight of co-catalyst (g) Na—S-SSA | Na conversion (%) | Acrylic Acid TON |
|---|---|---|---|---|
| 1 | 5.6 mg (1.0 × 10$^{-5}$) | 0.712 | 2.8 | 18.4 |
| 2 | 5.4 mg (9.7 × 10$^{-6}$) | 0.748 | 2.8 | 20.0 |
| 3 | 5.4 mg (9.7 × 10$^{-6}$) | 0.716 | 2.7 | 18.6 |
| 4 | 5.25 mg (9.6 × 10$^{-6}$) | 0.637 | 3.0 | 18.6 |

[A] Sodium acrylate extraction from the MT-CMSO was carried out using Extraction Procedure A for Run numbers 1-3 and Extraction Procedure B for Run number 4.

Example 3. Temperature Dependence of Acrylic Acid Production

The following experiments were performed to determine the effect of temperature on the acrylic acid TONs using the MT-CMSO activating supports. The procedure was identical to that described in Example 2, except that the reactor temperature was allowed to run for 20 h at 50° C. and 80° C. before the sodium acrylate was extracted from the MT-CMSO in the baskets. These experiments were performed with the same batch of Na—S-SSA solid activating support as used in Example 2.

As demonstrated in the Table 3 data, higher reaction temperatures led to progressively lower TON for acrylic acid formation and lower Na conversion. While not intending to be bound by theory, these observations were attributed to (a) the decreased solubility of reactants and nickelalactone in the liquid phase at the higher temperatures, and/or (b) the increased formation of malonate at higher temperatures due to over-oxidation of the Ni complex.

TABLE 3

Temperature dependence of acrylic acid production

| Weight (moles) of (dcpe)NiLac | Weight of co-catalyst (g) Na—S-SSA | Temperature (° C.) | Na Conversion (%) | Acrylic acid (AA) TON |
|---|---|---|---|---|
| Benchmark 5.25 mg (9.6 × 10$^{-6}$) | 0.725 | 40 | 2.6 | 19.0 |
| 5.6 mg (1.0 × 10$^{-5}$) | 0.737 | 50 | 2.5 | 16.9 |
| 5.5 mg (9.94 × 10$^{-6}$) | 0.894 | 80 | 0.4 | 3.0 |

Example 4. Pressure Dependence of Acrylic Acid Production

The following experiments were performed to determine the effect of total pressure on the observed acrylic acid TONs at 40° C. The procedure was identical to that described in Example 2, except that the partial pressures of $C_2H_4$ and $CO_2$ were increased from 150 psi each at 25° C. to 200 psi each at 25° C. Two identical runs were carried out using the 200 psi pressure conditions. The reaction was allowed to run for 20 h at 40° C. at the higher total pressure before the sodium acrylate was extracted from the MT-CMSO in the baskets. These experiments also were performed with the same batch of Na—S-SSA solid activating support as used in Examples 2 and 3.

As demonstrated in the Table 4 data, the higher partial pressures of $C_2H_4$ and $CO_2$ show lower and nearly identical TON (within experimental error) for acrylic acid formation in both the repeated runs. It was believed that this observation may be attributed to the higher pressures inducing precipitation of the (dcpe)NiLac nickelalactone complex from solution, because the non-polar gases in the liquid phase likely act to reduce solvation strength of the solvent with increasing non-polar gas concentration at higher pressures.

TABLE 4

Pressure dependence of acrylic acid production

| Weight (moles) of (dcpe)NiLac | Weight of co-catalyst (g) Na—S-SSA | $C_2H_4$/ $CO_2$ (psig) at 25° C. | Acrylic Acid TON |
|---|---|---|---|
| 5.25 mg (9.6 × 10$^{-6}$) | 0.725 | 150/150 | 19.0 |
| 5.2 mg (9.4 × 10$^{-6}$) | 0.759 | 200/200 | 12.9 |
| 5.2 mg (9.4 × 10$^{-6}$) | 0.716 | 200/200 | 14.3 |

To test the possible precipitation of the (dcpe)NiLac at higher ethylene and $CO_2$ pressures, a THF solution of the (dcpe)NiLac was examined when the solution was pressurized with $P_{C2H4}$ (ethylene pressure)=100 psig and $P_{CO2}$ (carbon dioxide pressure)=190 psig at 25° C., for a total pressure (P) of 290 psig at 25° C., and the liquid phase solution was observed to be clear. However, when the THF solution of the (dcpe)NiLac was pressurized with $P_{C2H4}$ (ethylene pressure)=150 psig and $P_{CO2}$ (carbon dioxide pressure)=300 psig at 40° C., for a total pressure (P) of 450 psig at 40° C., and the liquid phase was observed to be cloudy, indicating some precipitation of the (dcpe)NiLac.

Example 5. Reaction Time Dependence of Acrylic Acid Formation

The following experiments were performed for various time periods to determine the effect of batch reaction time on the observed acrylic acid TONs at 40° C. The reaction procedure was identical to that described in Example 2 using $C_2H_4/CO_2$ (psig)=150/150 at 40° C., except that the reaction was allowed to run for 5, 10, 20, and 40 h (hours) before the sodium acrylate was extracted from the baskets. These experiments were performed with the Na—S-SSA solid from the same batch as that used for the temperature and pressure effect runs of Examples 3 and 4. As demonstrated in Table 5, there is no substantial increase in the estimated TON for acrylic acid formation after 20 h. On this basis, 20 h was used as a standard batch reaction duration for these studies.

TABLE 5

Reaction time dependence of acrylic acid formation

| Weight (moles) of (dcpe)NiLac | Weight of co-catalyst (g) Na—S-SSA | Reaction Time (h) | Na Conversion (%) | Acrylic Acid TON |
|---|---|---|---|---|
| 5.25 mg (9.6 × 10$^{-6}$) | 0.637 | 5 | 0.2% | 1.5 |

TABLE 5-continued

Reaction time dependence of acrylic acid formation

| Weight (moles) of (dcpe)NiLac | Weight of co-catalyst (g) Na—S-SSA | Reaction Time (h) | Na Conversion (%) | Acrylic Acid TON |
|---|---|---|---|---|
| 5.25 mg ($9.6 \times 10^{-6}$) | 0.637 | 10 | 0.7% | 4.2 |
| 5.25 mg ($9.6 \times 10^{-6}$) | 0.725 | 20 | 2.6% | 19.0 |
| 5.6 mg ($1.0 \times 10^{-5}$) | 0.727 | 40 | 3.0% | 19.9 |

Example 6. Effect of Replacing the Solid MT-CMSO ("Solid Base") after First Run

As a result of the observations from the reaction time studies of acrylic acid formation, studies were carried out to determine whether the plateauing of the TON after 20 h likely was related to the possible depletion and/or degradation of the nickelalactone (dcpe)NiLac, or whether the TON plateauing likely was related to the lack of available catalytic sites and/or deactivation of the sites within the sodium-treated CMSO solid base.

To examine possible deactivation of the solid base as causing or related to the plateauing of the TON after 20 h, a first 20 h run was conducted using the same experimental conditions and procedure as used in Example 2 of $C_2H_4/CO_2$ (psig)=150/150 at 25° C. and Reaction T (temperature)=40° C. After the first 20 h run, the spent MT-CMSO solid was replaced with fresh solid from the same Na—S-SSA batch. The remaining reaction mixture was not removed except for a small amount that may have escaped during the depressurization step. Instead, the baskets were replaced with ones containing fresh solid from the same Na—S-SSA batch that was used in the first 20 h run. A second 20 h run was then performed using the same conditions and procedures as those used for the first 20 h run of $C_2H_4/CO_2$ (psig)=150/150 at 25° C. and Reaction T (temperature)=40° C.

As summarized in Table 6, the measured TON for acrylic acid formation was 18 during the first 20 h run, remarkably consistent with results from previous runs under these conditions. However, the TON following the second 20 h run decreased dramatically to 2, suggesting that deactivation of the solid base is not the cause of the observed loss of activity after 20 h. Based on this information, the effect of increasing (dcpe)NiLac nickelalactone concentration on acrylic acid formation activity was subsequently investigated.

TABLE 6

Effect of replacing the solid base MT-CMSO after first run

| Run | Weight (moles) of (dcpe)NiLac | Weight of co-catalyst (g) Na—S-SSA | Acrylic Acid TON |
|---|---|---|---|
| First 20 h run | 5.25 mg ($9.6 \times 10^{-6}$) | 0.672 | 18.0 |
| Second 20 h run, with fresh MT-CMSO | 5.25 mg ($9.6 \times 10^{-6}$) | 0.692 | 2.0 |

Example 7. Effect of Increasing the Nickelalactone Concentration

Because the previous experiment suggested that deactivation of the solid base is not the cause of the observed loss of activity after 20 h, the effect of increasing nickelalactone (dcpe)NiLac concentration was examined to determine how (dcpe)NiLac availability influences the observed TON for acrylic acid formation. In these experiments, two (dcpe)NiLac concentrations were used in the reaction mixture, the first being nearly identical to those in Example 2 and Table 2, and the second being approximately double that concentration. The doubled concentration value was still below the limit that causes (dcpe)NiLac precipitation from THF solution upon pressurization with $CO_2$ and $C_2H_4$ gases.

Using an activator solid from the same Na—S-SSA batch as used in the previous experiments, a 20 h run was conducted using the same experimental conditions and procedures as used in Example 2 of $C_2H_4/CO_2$ (psig)=150/150 at 25° C. and Reaction T (temperature)=40° C. for each (dcpe)NiLac concentration. As summarized in Table 7, the measured TONs for acrylic acid formation (moles of acrylic acid produced per moles of (dcpe)NiLac in the reactor) after each 20 h run was approximately 20, which is similar to the TON values obtained at the lower (dcpe)NiLac concentration (Table 2). This data indicates a proportional doubling of the acrylic acid formation with (dcpe)NiLac concentration as also approximately reflected in the Na conversion percentage.

TABLE 7

Effect of doubling nickelalactone concentration

| Weight (moles) of (dcpe)NiLac | Weight of co-catalyst (g) Na—S-SSA | Na conversion (%) | Acrylic Acid TON |
|---|---|---|---|
| 5.25 mg ($9.6 \times 10^{-6}$) | 0.725 | 2.6 | 19.0 |
| 11.0 mg ($1.99 \times 10^{-5}$) | 0.699 | 6.1 | 20.0 |

Example 8. Effect of Replenishing the Catalyst with Afresh Nickelalactone Solution Using an activator solid from the same Na—S-SSA batch as used in the previous experiments, a first 20 h run was performed under experimental conditions and procedures similar to those of Example 2 of $C_2H_4/CO_2$ (psig)=150/150 at 25° C. and Reaction T (temperature)=40° C. The reactor was cooled and the gases were released according to the procedures described in Example 2, after which the THF solution was removed from the reactor. Without removing the solids from the baskets, the reactor was closed and flushed with $N_2$ (HP grade, 99.99%) for 5-10 min at ambient temperature.

Following the first 20 h run after which the THF solution was removed from the reactor, a second 20 h run was performed in which the reactor was replenished with a fresh THF solution (30 mL) containing nickelalactone (dcpe)NiLac at an identical concentration (5.25 mg (dcpe)NiLac in 30 mL THF), but using the same MT-CMSO retained in the baskets from the first 20 h run. After this second 20 h run, the baskets containing the solids were removed and the acrylic acid was harvested according to the Extraction Procedure B of Example 2. As summarized in Table 8, the measured TON for acrylic acid formation after the first and second 20 h runs was approximately 16.2. This value is close to the TON value of 19 observed in a benchmark 20 h run, performed according to Example 2 which is shown in Table 8, suggesting that the amount of acrylic acid formation increased nearly proportionally with the cumulative amount of (dcpe)NiLac used in the two runs. This observation is also reflected in the stoichiometrically equivalent increase in Na conversion.

This result indicates that the metal-treated chemically-modified solid oxide was still active for acrylate formation after the first 20 h run. The fact that the acrylate formation activity was nearly lost during the second 20 h run when the (dcpe)NiLac solution was not replenished, but instead only the solid base MT-CMSO was replaced after first run (Example 6 and Table 6) suggests one or more of the following possibilities: (a) The (dcpe)NiLac nickelalactone complex should be replenished to sustain acrylic acid formation; (b) potential byproducts may build up in the solvent that should be removed to sustain acrylic acid formation; and/or (c) the (dcpe)NiLac nickelalactone complex was removed with the solid cocatalyst. As demonstrated further experiments, this latter possible reason was shown to be a causative factor.

TABLE 8

Effect of replacing nickelalactone on acrylic acid formation

| Run | Weight (moles) of (dcpe)NiLac | Weight of co-catalyst (g) Na—S-SSA | Na conversion (%) | Acrylic Acid TON |
|---|---|---|---|---|
| Benchmark | 5.25 mg $(9.6 \times 10^{-6})$ | 0.725 | 2.6 | 19.0 |
| First 20 h | 5.25 mg $(9.6 \times 10^{-6})$ | 0.674 | — | — |
| Second 20 h [A] | 5.25 mg $(9.6 \times 10^{-6})$ | Not replaced | 4.8 | 16.2 |

[A] Liquid phase removed after the first 20 h run and replaced with fresh nickelalactone (dcpe)NiLac solution. TON estimated from extracting acrylate from MT-CMSO solids following the second 20 h run.

Example 9. Effect of Replenishing the Nickelalactone Catalyst Only

This example varies from Example 8 by replenishing the catalyst by reloading the (dcpe)NiLac nickelalactone only rather than replenishing the catalyst with a fresh (dcpe)NiLac nickelalactone solution as in Example 8. Using activator solid from the same Na—S-SSA batch as used in the previous experiments, a first 20 h run was performed using the same experimental conditions and procedures as used in Example 2 of $C_2H_4/CO_2$ (psig)=150/150 at 25° C. and Reaction T (temperature)=40° C.

After the first 20 h run, the reactor was cooled to room temperature and the pressure decreased to ~25 psig by gas release, without opening the reactor lid. Neither the liquid phase nor the solid was removed to investigate if reaction byproducts were inhibiting the reaction. While retaining these liquid phase and solid components, a solution containing 5.25 mg nickelalactone in 5 mL THF was added through the injection port with a gastight syringe before performing the second 20 h run under the same reaction conditions as the first 20 h run.

Following the second 20 h run, the baskets containing the solids were removed and the acrylic acid was harvested. As summarized in Table 9, the measured TON for acrylic acid formation after the first two 20 h runs was approximately 17.5. This value is again close to the TON value of 19 observed in the benchmark 20 h run, suggesting that the amount of acrylic acid formation increased more or less proportionally with the cumulative amount of nickelalactone used in the two runs. The increase in Na conversion (from 2.6 wt. % to 4.8 wt. %) also tracks the amount of acrylic acid formed. Therefore, this Example demonstrates that byproducts from the reaction are not inhibiting the reaction, because the second 20 h run was conducted in the presence of any byproducts that might have been generated from the first 20 h run. However questions remain as to whether the (dcpe)NiLac nickelalactone complex should be replenished to sustain acrylic acid formation, or the (dcpe)NiLac nickelalactone complex was removed with the solid co-catalyst.

TABLE 9

Effect of replacing nickelalactone on acrylic acid formation

| Run [A] | Weight (moles) of (dcpe)NiLac | Weight of co-catalyst (g) Na—S-SSA | Na conversion (%) | Acrylic Acid TON |
|---|---|---|---|---|
| Benchmark | 5.25 mg $(9.6 \times 10^{-6})$ | 0.725 | 2.6 | 19.0 |
| First 20 h | 5.25 mg $(9.6 \times 10^{-6})$ | 0.736 | — | — |
| Second 20 h | 5.25 mg $(9.6 \times 10^{-6})$ | Not replaced | 4.8 | 17.5 |

[A] Neither liquid phase nor solid phase removed after the first 20 h run; instead, 5.25 mg nickelalactone (dcpe)NiLac in 5 mL of THF were added after the first 20 h run. TON estimated from extracting acrylate from solids following the second 20 h run.

Example 10. Effect of Periodic Replenishment of Solvent Only without Additional Nickelalactone This Example was carried out in the same manner as Example 8, with the exception that the liquid phase was removed after the first 20 h run, and was replaced with fresh THF solvent only (30 mL), and the experiment was repeated without removing the solid from the catalyst basket. Following the second 20 h run, the reactor was cooled down, the gases released and the solids from the baskets processed to harvest acrylic acid as described in Example 2 according to Extraction Procedure B.

As shown in Table 10, the TON for acrylic acid formation and Na conversion nearly doubled suggesting that neither the depletion of (dcpe)NiLac nickelalactone nor the deactivation of the solid base was causative for the plateauing of the TON after 20 h. Therefore, the nickelalactone was neither largely functioning in solution such that it was removed with the solvent, nor was the solid base somehow exhausted. Rather, merely stopping the reaction, removing solvent, and re-pressurizing the reaction vessel induced further reaction and sodium acrylate formation.

TABLE 10

Acrylic acid formation following solvent replacement after 1st 20 h run

| Weight (moles) of (dcpe)NiLac | Weight of co-catalyst (g) Na—S-SSA | Number of 20 h reaction cycles | Na Conversion (%) | Acrylic Acid TON |
|---|---|---|---|---|
| Benchmark 5.25 mg $(9.6 \times 10^{-6})$ | 0.725 g | 1 | 2.6 | 19.0 |
| 5.6 mg $(1.0 \times 10^{-5})$ | 0.701 g | 2 | 5.3 (2 cycles) | 34.4 (2 cycles) |

Thus, while not intending to be bound by theory, it thus appears that the (dcpe)NiLac nickelalactone impregnates itself into or onto the solid resin during the first 20 h run, and the $C_2H_4$ and $CO_2$ react exclusively on the solid MT-CMSO to form sodium acrylate in subsequent 20 h runs with simple solvent replacement. This observation raises another question of whether the pressure swing or temperature swing (during the steps of releasing the gas pressure and cooling after 20 h, replacing solvent with a fresh batch and re-pressurizing the reactor with $CO_2$ and $C_2H_4$ and reheating for the next cycle) somehow reactivates the solid MT-CMSO without the need for fresh solvent addition every 20 h. To investigate this possibility, designed pressure swing experiments were performed without solvent replacement, as explained in the next Example.

Example 11. Pressure Swing Experiments with and without Solvent Replacement after 20 h The following reaction runs were performed in order to uncouple the pressure, solvent replacement, and temperature effects during the pressure-cycles every 20 h and obtain evidence for the influence of each of these on the reaction.

A. Isothermal pressure (P) swing with no solvent replacement. The various steps in the isothermal pressure swing experiments are shown in FIG. 4. This run is also termed Example 11A as well as simply run A of this example.

Following a 20 h run with the MT-CMSO solid according to Example 2, the gases were released at 40° C. without cooling the reactor through tuning of the temperature controller. At the set temperature, approximately 0.9 mL (~3%) of the solvent phase was also lost and was not replenished. Without replacing any solvent, the reactor was then repressurized gradually to the original operating pressure at 40° C. (420 psig) with equal partial pressures of $C_2H_4$ and $CO_2$, while maintaining the reactor temperature at 40° C.

Following another 20 h, the reactor was cooled to room temperature, the gases slowly released, and the product extracted following Extraction Procedure B as explained in Example 2. Thus, in this run there was one pressure swing after 20 h with a total run time of 40 h. As seen from pressure and temperature profiles, excellent temperature control was maintained throughout the 40 h run with an overshoot of only approximately 2° C. during the repressurization step.

B. Non-isothermal pressure (P) swing with solvent replacement. The experimental procedure was similar to Example 11A was used except that the liquid phase was removed after the first 20 h while maintaining the temperature at 40° C., then the reactor was recharged with 30 mL of fresh THF at 40° C. The reactor was then repressurized with $CO_2$ and $C_2H_4$ back to the operating pressure of the first 20 h run at equal partial pressures of ethylene and $CO_2$ for the second 20 h run at 40° C. There was one pressure swing after 20 h with a total run time of 40 h.

C. Non-isothermal pressure (P) swings with solvent replaced every 20 h. The experimental procedure used in this test was similar to that of Example 11B with solvent replacement, except that the pressure swing experiment was continued for two more cycles at 40° C. In all, there were three pressure swings after 20 h each with a total run time of 80 h. The product was recovered from the basket and extracted after the total 80 h run time.

D. Non-isothermal pressure (P) swing with no solvent replacement. The experimental procedure used in this test was similar to that of Example 11A, except that the reactor was cooled down to room temperature after 20 h before repressurization and reheating to 40° C. without solvent removal or replacement. In all, there was one pressure swing after 20 h with a total run time of 40 h.

As shown in Table 11, the isothermal pressure swing after 20 h without replacement of the original liquid phase containing dissolved (dcpe)NiLac nickelalactone (run A), or the non-isothermal pressure swing with replacement of the liquid phase with only fresh THF (run B), results in similar TON enhancements compared to either the 20 h (run B1) or the 40 h (run B2) baseline runs without any pressure swings. Further, the TON continues to increase with successive non-isothermal pressure swings at 20 h intervals, reaching approximately 73 in an 80 h run interspersed with three pressure swings at 20 h, 40 h, and 60 h, with fresh solvent replacement after each pressure release (run C). These data translate to roughly a TON enhancement of 18 per every 20 h segment.

These observations demonstrate the following: (a) the TON reaches a plateau of ~20 after 20 h without a pressure swing; and (b) the beneficial role of a pressure swing in "reactivating" the solid after every 20 h and enhancing the acrylic acid TON is observed. It was also found that the TON enhancement is independent of whether the pressure swing was performed isothermally at the reactor temperature (run A) or non-isothermally with cooling to ambient temperature prior to solvent replacement (run D). Further, the sodium (Na) conversion based on the amount of Na in the starting and spent solids also increases with acrylic acid TON and that the TON approximately scales with the amount of solid (with an identical Na weight fraction) used in the experiments (runs B and D).

TABLE 11

Effect of pressure swing after 20 h on TON of the Example 11 runs

| Run | Weight (moles) of (dcpe)NiLac | Weight of co-catalyst (g) Na—S-SSA | Number of 20 h Pressure Swings | Na conversion (%) | Total time (h) | Acrylic Acid TON |
|---|---|---|---|---|---|---|
| B1: Benchmark (20 h run) | 5.2 mg (9.4 × 10$^{-6}$) | 0.725 g | 0 | 2.6 | 20 | 19.0 ± 0.5 |
| B2: Benchmark (40 h run) | 5.6 mg (1.01 × 10$^{-5}$) | 0.727 g | 0 | 3.0 | 40 | 19.9 |
| A. Isothermal P swing with no solvent replacement | 5.7 mg (1.03 × 10$^{-6}$) | 0.656 g | 1 | 5.9 | 40 | 35.2 |
| B. Non-isothermal P swing with solvent replacement | 5.6 mg (1.01 × 10$^{-5}$) | 0.729 g | 1 | 5.3 | 40 | 33.4 ± 0.8 |
| C. Non-isothermal P swings with solvent replaced every 20 h | 5.7 mg (1.03 × 10$^{-6}$) | 0.716 g | 3 | 11.1 | 80 | 72.6 |

TABLE 11-continued

Effect of pressure swing after 20 h on TON of the Example 11 runs

| Run | Weight (moles) of (dcpe)NiLac | Weight of co-catalyst (g) Na—S-SSA | Number of 20 h Pressure Swings | Na conversion (%) | Total time (h) | Acrylic Acid TON |
|---|---|---|---|---|---|---|
| D. Non-isothermal P swing with no solvent replacement | 5.7 mg (1.03 × 10$^{-6}$) | 0.590 g | 1 | 5.2 | 40 | 27.7 |

Example 12. Quantitative Nuclear Magnetic Resonance Studies

To complement the pressure-swing experiments, proton and proton-decoupled phosphorus Nuclear Magnetic Resonance ($^1$H and $^{31}$P{$^1$H} NMR, respectively) studies were performed to assess the fate of the (dcpe)NiLac nickelalactone catalyst. Specifically the amount of nickelalactone catalyst that may be lost from the heterogeneous base material following catalysis, including multiple runs with the same impregnated solid-catalyst material, was examined.

The $^{31}$P{$^1$H} NMR spectrum of the nickelalactone complex (dcpe)NiLac carried out under stringent air-free and moisture-free conditions revealed two singlets at δ 68.52 and δ 62.39. These two resonances correspond to the two inequivalent P atoms contained in the dcpe ligand (bis(dicyclohexylphosphino)ethane ligand, $(C_6H_{11})_2$ $PCH_2CH_2P(C_6H_{11})_2$) when bound to Ni. The signals are downfield of the free ligand, consistent with the P atoms being bound to the nickel center.

Each extraction sample following a catalytic run was also examined by $^{31}$P{$^1$H} NMR and each sample revealed a singlet at ca. δ 48.5 ppm. The presence of this single resonance suggests a chemical change in the nickelalactone material following catalysis, and the upfield shift may indicate that the P atoms are no longer bound to a nickel center. Additionally, the lone singlet indicates that the species is a more symmetric compound, likely one in which the two P atoms of the ligand are magnetically equivalent. Comparison of literature reports suggests that this signal corresponds to the oxidized form of the bis(dicyclohexylphosphino)ethane (dcpe) ligand, $(C_6H_{11})_2P(O)CH_2CH_2P(O)(C_6H_{11})_2)$, in which each phosphorus atom is converted to a phosphine oxide moiety. The $^{31}$P{$^1$H} NMR signal for this compound is reported at δ 51.9 in deuterated chloroform (see Baldwin, L. C.; Fink, M. J. J. Organomet. Chem. 2002, 646, 230-238) and this slight variation in chemical shift among differing solvents is to be expected.

Quantitative $^{31}$P{$^1$H} NMR studies were carried out with a known amount of triphenylphosphine oxide (TPPO) as an internal standard. Volatiles of the extraction samples following catalysis were removed in vacuo to provide extraction solids, and a solution of each extraction solid sample was prepared in deuterated benzene ($C_6D_6$) to examine the non-volatile material remaining. The internal standard TPPO is observed as a singlet at δ 25.08, which allowed a quantitative analysis of the amount of the compound assigned as the oxidized form of the bis(dicyclohexylphosphino)ethane (dcpe), $(C_6H_{11})_2P(O)CH_2CH_2P(O)(C_6H_{11})_2)$.

The extraction material was integrated in comparison to the known internal standard TPPO for the quantitative analysis. The calculation for finding the amount of phosphorus (P) containing material from the sample extractions were based on the integration of TPPO divided by the of the number of P atoms in TPPO, as illustrated in the following equation.

$$\text{Amount of } P \text{ containing product} = \frac{(\text{mol of } TPPO \text{ interal standard})}{2} (\text{Integration of } P \text{ containing extraction product})$$

The values shown for the integration of TPPO versus the amount of P containing material from the extraction sample are shown in Table 12, which reveals that only relatively small amounts of catalyst material were lost during extraction. The Run numbers in Table 12 include the Example procedure (e.g., "Example 16") and run number for that example (e.g., "-2"). The samples for Runs 7-1 to 17-4 resulted in a range of 2.93 mol % loss to 38.7 mol % loss of catalyst from the extraction (see Table 12 footnotes for the explanations for the higher percent loss for Runs 17-5 through and 17-8). These results suggest that the majority of the nickelalactone-derived catalyst material is impregnated on or in the heterogeneous base material such that is it fixed and is not lost during extraction.

TABLE 12

Amount of phosphorus (P)-containing species (oxidized dcpe) in extraction samples by NMR calculation.

| Run (Example-Run | (dcpe)NiLac Nickelalactone impregnation time | Initial amount of nickelalactone catalyst loaded | Amount of oxidized dcpe found in solution by NMR | Mole percent of P-containing product found (as percentage of original nickelalactone catalyst loading) |
|---|---|---|---|---|
| Example 7-1 | 20 h | 1.9 × 10$^{-5}$ mol | 5.57 × 10$^{-7}$ mol | 2.93% |
| Example 10-1 $^A$ | 20 h | 1.0 × 10$^{-5}$ mol | 5.38 × 10$^{-7}$ mol | 5.53% |
| Example 10-2 $^A$ | 20 h | 1.0 × 10$^{-5}$ mol | 4.27 × 10$^{-7}$ mol | 4.27% |
| Standard run | 20 h | 1.0 × 10$^{-5}$ mol | 1.42 × 10$^{-6}$ mol | 14.2% |

TABLE 12-continued

Amount of phosphorus (P)-containing species (oxidized dcpe) in extraction samples by NMR calculation.

| Run (Example-Run | (dcpe)NiLac Nickelalactone impregnation time | Initial amount of nickelalactone catalyst loaded | Amount of oxidized dcpe found in solution by NMR | Mole percent of P-containing product found (as percentage of original nickelalactone catalyst loading) |
|---|---|---|---|---|
| Example 16-1 | 20 h | $1.0 \times 10^{-5}$ mol | $1.93 \times 10^{-6}$ mol | 19.3% |
| Example 16-2 | 20 h | $1.0 \times 10^{-5}$ mol | $3.40 \times 10^{-6}$ mol | 34.0% |
| Example 16-3 | 20 h | $1.0 \times 10^{-5}$ mol | $2.19 \times 10^{-6}$ mol | 21.9% |
| Example 16-4 [B] | 20 h | $1.0 \times 10^{-5}$ mol | $1.53 \times 10^{-6}$ mol | 15.3% |
| Example 16-5 | 20 h | $1.0 \times 10^{-5}$ mol | $2.30 \times 10^{-6}$ mol | 23.0% |
| Example 16-6 | 20 h | $1.0 \times 10^{-5}$ mol | $4.05 \times 10^{-7}$ mol | 4.01% |
| Example 17-1 [C] | 2 h | $1.05 \times 10^{-5}$ mol | $2.52 \times 10^{-6}$ mol | 24.0% |
| Example 17-2 [C] | 2 h | $1.05 \times 10^{-5}$ mol | $2.47 \times 10^{-6}$ mol | 23.5% |
| Example 17-3 [C] | 2 h | $1.05 \times 10^{-5}$ mol | $4.06 \times 10^{-6}$ mol | 38.7% |
| Example 17-4 [C] | 2 h | $1.05 \times 10^{-5}$ mol | $3.91 \times 10^{-6}$ mol | 37.2% |
| Example 17-5 [C] | 2 h | $9.94 \times 10^{-6}$ mol | $4.52 \times 10^{-6}$ mol | 45.5% |
| Example 17-6 [C] | 2 h | $9.94 \times 10^{-6}$ mol | $4.63 \times 10^{-6}$ mol | 46.6% |
| Example 17-7 [C,D] | 2 h | $9.94 \times 10^{-6}$ mol | $4.13 \times 10^{-6}$ mol | 41.6% |
| Example 17-8 [C,D] | 2 h | $9.94 \times 10^{-6}$ mol | $4.22 \times 10^{-6}$ mol | 42.5% |

[A] Runs 10-1 and 10-2 are the first extraction and the second extraction, respectively, of the same sample run.
[B] Power outage occurred 15 h into the run
[C] 2 h impregnation time with THF at 40 psig mixed gas condition, new batch of Na—S-SSA
[D] Only used 400 mg of Na—S-SSA, which is ½ of the usual amount of 800 mg of Na—S-SSA. After normalized by amount of Na—S-SSA, (dcpe)NiLac percent in the liquid phase = 20.8%

These results revealed that only a small percentage of detectable $^{31}$P-containing material was observed in the liquid phase removed from the reactor after each batch run, specifically on the order of about 2 mol % to about 5 mol % of total initial loading of (dcpe)NiLac per reaction cycle. This data indicates that the (dcpe)NiLac, or in particular its dcpe ligand component, remains tightly associated with the solid base material following each batch run.

Example 13. Solvent Effects

Catalytic runs were also carried out using toluene as the solvent according to the procedure of Example 2 for a comparison with the runs using THF as the solvent. The results are provided in Table 13 as the first two entries. A significantly greater TON value was observed when using toluene as the solvent (TON=32.1) as compared to THF as the solvent (TON=19) for almost identical operating conditions. This observation is consistent with the greater stability encountered in control NMR experiments with use of toluene in place of THF. The TON enhancement is also seen in the pressure swing experiments of Table 12, comparing the third and fourth entries, although the difference is less pronounced as compared to the runs without the pressure swing. These observations with different solvents also confirm the beneficial role of periodic pressure swings on the observed TON.

TABLE 13

Effect of toluene versus THF as solvent on TON

| Solvent | Weight (moles) of (dcpe)NiEac | Weight of co-catalyst (g) Na—S-SSA | Number of 20 h Pressure Swings | Total time (h) | Na conversion (%) | Acrylic Acid TON |
|---|---|---|---|---|---|---|
| THF (20 h run) | 5.2 mg ($9.4 \times 10^{-6}$) | 0.725 g | 0 | 20 | 2.6 | 19.0 ± 0.5 |
| Toluene (20 h run) | 5.6 mg ($1.01 \times 10^{-5}$) | 0.758 g | 0 | 20 | 4.6 | 32.1 |
| THF (Isothermal) | 5.7 mg ($1.03 \times 10^{-6}$) | 0.656 g | 1 | 40 | 5.9 | 35.2 |
| Toluene (Isothermal) | 5.6 mg ($1.01 \times 10^{-5}$) | 0.647 g | 1 | 40 | 7.0 | 42.1 |

Example 14. Metal-Treated Solid Oxide ("Solid Base") Effects

A sample of Na—Y zeolite was purchased from Alfa Aesar and used without any further treatment. The Na-MCM-41 and Na/Al-KIT-6 solid oxides were prepared as described above. The Na content of each of the Na—Y zeolite, Na-MCM-41 and Na/Al-KIT-6 samples were measured to be 9 wt. %, 3.8 wt. %, and 3.3 wt. %, respectively, as summarized in Table 14 along with other physical properties of these materials. These sodium weight percent values are lower than the Na content in Na—S-SSA solid, which averaged 21.5 wt. %.

TABLE 14

Physical properties of Na—Y zeolite, Na-MCM-41 and Al/Na-KIT-6

| Metal-Treated Solid Oxide | Na—Y zeolite | Na-MCM-41 | Na/Al-KIT-6 |
|---|---|---|---|
| Na (wt. %) | 9.0 | 3.80 | 3.34 |
| Average Pore Diameter | 0.8 nm | 3.3 nm | 7.6 nm |
| Si/Al ratio | 1:1 | 12:1 | 10:1 |

Experiments were performed using Na—Y zeolite, Na-MCM-41 and Na/Al-KIT-6 as co-catalysts, employing the method and other conditions described in Example 2, using a $C_2H_4/CO_2$ (psig) ratio of 150/150 at 40° C. for 20 h reaction time. The results are outlined in Table 15 and demonstrate that the TON values for acrylic acid formation with Na—Y zeolite, Na-MCM-41 and Na/Al-KIT-6 are less than that obtained with Na—S-SSA solid, even after accounting for the differences in the amount of solid oxides and their Na contents. These observations may indicate that other features such as pore structure in the solid may also have an effect on the observed TON.

TABLE 15

Effect of co-catalyst

| Co-catalyst | Weight (moles) of (dcpe)NiLac | Na content (wt. %) | Total time (h) | Acrylic Acid TON |
|---|---|---|---|---|
| 0.725 g Na—S-SSA | 5.2 mg (9.4 × 10⁻⁶) | 21.5 | 20 | 19.0 ± 0.5 |
| 1.4 g Na—Y zeolite | 5.2 mg (9.4 × 10⁻⁶) | 9.0 | 20 | 7.0 |
| 0.9 g Na-MCM-41 | 5.2 mg (9.4 × 10⁻⁶) | 3.8 | 20 | 4.9 |
| 1.0 g Na/Al-KIT-6 | 5.2 mg (9.4 × 10⁻⁶) | 3.3 | 20 | 2.6 |

Example 15. Nickelalactone Impregnation into the Treated Solid Oxide for Gas-Phase Reaction Studies Either 400 mg or 800 mg of sodium treated SSA Na—S-SSA were equally distributed into the two wire-mesh baskets attached to the stirrer rod as described above. The stirrer with the attached baskets was then installed in the 50 mL PARR® reactor, which was then closed and flushed with $N_2$ for 15 min. Approximately 5 mg of nickelalactone (dcpe) NiLac was dissolved in 30 mL of THF and the mixture was injected into the reactor. The data for these runs is presented in Table 16. The reactor was then charged at room temperature with equal partial pressures of $C_2H_4$ and $CO_2$ reaching a total pressure of either 300 psig (for high pressure runs) or 36 psig (for low pressure runs). The reactor contents were then heated to 40° C. with stirring, which was continued for either 2 or 20 h. Following either run period, the liquid phase was collected for NMR analysis. Table 16 summarizes the $^{31}P\{^1H\}$ NMR analysis results of phosphorus-containing materials in the liquid phase. The balance of the (dcpe) NiLac nickelalactone is indicated as impregnated. Oxidized dcpe ligand was typically detected in this work, possibly indicating loss of impregnated (dcpe)NiLac nickelalactone from the oxide surface followed by oxidation during workup of the reactor contents.

TABLE 16

$^{31}P\{^1H\}$ NMR analysis results of the liquid phase following (dcpe)NiLac impregnation

| Initial amount of (dcpe)NiLac nickelalactone in solution (×10⁻⁵ mol) | Nickelalactone impregnation time (h) | Amount of nickelalactone in liquid phase from $^{31}P\{^1H\}$ NMR (×10⁻⁶ mol) | Nickelalactone (%) in liquid phase by NMR | Nickelalactone (%) impregnated in Na—S-SSA |
|---|---|---|---|---|
| 1.00 ᴬ | 20 | 2.01 ᴬ | 20.1 | 79.9% |
| 1.05 ᴰ | 2 | 2.50 ᴮ | 23.8 | 76.2 |
| 1.05 ᴰ | 2 | 4.06 | 38.7 | 61.3 |
| 0.994 ᴰ | 2 | 4.52 | 45.2 | 54.8 |
| 0.994 ᴰ | 2 | 4.13 ᶜ | 41.55 | 68.45 |

ᴬ Average of 3 experiments. Conditions: 300 psig of $C_2H_4$ and $CO_2$ (150 psig each) charged initially at RT.
ᴮ Average of 2 experiments
ᶜ Used ~400 mg of Na—S-SSA
ᴰ Reactor pressure: 36 psig of $C_2H_4$ and $CO_2$ (18 psig each) charged initially at RT Based on the first and second row entries in Table 16, 75% to 80% (by weight or mole) of (dcpe)NiLac nickelalactone from solution was impregnated into or onto the solid phase at both impregnation times (2 or 20 h) and total gas pressures (36 or 300 psig at RT). In some of the runs (see third and fourth row entries in Table 16), only 55% to about 60% (dcpe)NiLac impregnation was achieved. A repeat run (fifth row entry) confirmed the achievement of 68% (dcpe)NiLac loading in the solid phase in 2 h at 36 psig gas pressure (RT). As a result, a (dcpe)NiLac impregnation time of 2 h was used in all subsequent runs.

Example 16. High Pressure Gas-Phase Reaction Study

The (dcpe)NiLac was impregnated on Na—S-SSA over 20 h using the procedure described in Example 14, with 5.6 mg (1.0×10⁻⁵ mol) of nickelalactone in 30 mL THF, after which the PARR® reactor was cooled to room temperature. The liquid phase was then removed for NMR analysis and the reactor containing the baskets loaded with (dcpe)NiLac-impregnated solid was dried for 1 h at either room temperature (RT) or at 40° C. under vacuum. The reactor was then charged with $C_2H_4$ first (150 psig partial pressure at RT) followed by $CO_2$ next (150 psig partial pressure at RT), each from separate cylinders, to attain a total reactor pressure of 300 psig at RT. No solvent or liquid carrier was used. The reactor was then heated to various operating temperatures and the run performed for 20 h, as shown in Table 17. After each run, the reactor was cooled down and the acrylate product was extracted from the basket following the procedure explained in Example 2 (Extraction Procedure B). Table 17 summarizes the results from various runs performed using this procedure.

TABLE 17

Gas phase reactions in the absence of a liquid carrier [A]

| Run | Na—S-SSA loading (g) | (dcpe)NiLac impregnation time (h), T (° C.) | Impregnation + reaction time (h) | Gas phase reaction T (° C.) | Reactor pressure (psig) | TON |
|---|---|---|---|---|---|---|
| A | 0.690 | 20/40 | 40 | 40 | 430 | 96.8 |
| B | 0.723 | 20/40 | 40 | 40 | 452 | 122.0 |
| C | 0.950 | 20/40 | 40 | 40 | 447 | 75.3 |
| D | 0.788 | 20/40 | 40 | 60 | 541 | 95.5 |
| E | 0.650 | 20/40 | 40 | 80 | 375 [B] | 87.6 |
| F | 0.788 [C] | 20/40 | 40 | 80 | 353 [B] | 90.7 |

[A] Reaction conditions: (dcpe)NiLac: 5.6 mg (1.0 × 10$^{-5}$ mol) in 30 mL THF, Na—S-SSA;
[B] Reactor pressure regulator recalibrated
[C] Used new batch of Na—S-SSA As the Table 17 data illustrate, the gas phase runs at 40° C. produced TON values ranging from 75-122. These values are generally greater than those produced during liquid phase runs at 40° C. (see Table 11, Example 11). Gas phase runs at 60° C. and 80° C. also yielded similar turnover numbers (TONs). The rather weak temperature dependence of TON on temperature strongly suggests that the overall conversion is limited by pore diffusion rates at the operating pressures. To alleviate pore diffusion limitations, reactions were performed at lower pressures as shown in the following example.

Example 17. Low Pressure Gas-Phase Reaction Study

The reactor set-up used above for the high-pressure gas studies was modified for use in the low-pressure gas phase runs as follows. First, the 50 mL PARR® reactor was switched to one with a liquid outlet at the bottom of the vessel, which permitted withdrawal of the liquid phase following impregnation while avoiding contact with air. Secondly, a 150 mL external cylinder was used to store the mixed gas of $C_2H_4$ and $CO_2$ in equimolar amounts at pressures where the mixture exists as a single phase at RT. The external cylinder was equipped with a thermocouple, pressure transducer and a jacket for circulating a heat transfer medium such as water to maintain a constant temperature.

In this set of experiments, the procedure for (dcpe)NiLac impregnation was similar to that described in Example 15, except that the impregnation time was 2 h instead of 20 h. The extent (dcpe)NiLac impregnation into Na—S-SSA was determined from $^{31}P\{^1H\}$ NMR analysis, as summarized in Example 15 and Table 16. Following the 2 h impregnation followed by removal of the liquid phase, the reactor was vacuum-dried at 60° C. for 1 h and then flushed with $N_2$ for 15 minutes. The reactor was heated to the desired reaction temperature and then supplied with mixed gas. The mixed gas from the external reservoir (initial mixed gas pressure at ~130 psig at 25° C.) was supplied continuously to the reactor to maintain a constant reactor pressure of ~36 psig. As summarized in Table 18, the max TON attained was 148 at 120° C. Note that this TON value was attained in 22 h, including impregnation time of 2 h.

TABLE 18

Gas phase reaction at lower pressures and higher temperatures [A]

| Run | Na—S-SSA | (dcpe)NiLac impregnation time (h)/T (° C.) | Total reaction time (h) | Gas phase reaction temp (° C.) | Reactor pressure (psig) | TON |
|---|---|---|---|---|---|---|
| A | 0.743 | 2/40 | 22 | 80 | 35 | 102.1 |
| B | 0.785 | 2/40 | 22 | 80 | 36 | 100.3 |
| C | 0.812 | 2/40 | 22 | 120 | 36 | 148.2 |

[A] (dcpe)NiLac: 5.8 mg (1.07 × 10$^{-5}$ mole) in 30 mL THF solvent, (dcpe)NiLac impregnation at 40 psig ($C_2H_4$ + $CO_2$) for 2 h and gas phase reaction at 36 psig for 20 h.

Even though a 50% increase in TON values was observed at 120° C. (compared to 80° C.), the enhancement is not characteristic of typical temperature effect on kinetically controlled reaction rates. While not intending to be bound by theory, it is believed that the overall conversion is subject to mass transfer limitations.

Example 18. Product Extraction Methods

Product extraction from the Ni—S-SSA was found to be a very slow step and could require tens of hours per batch to completely extract the acrylate formed. Four different methods to improve the extraction time were tested. The sample to be extracted was prepared by using ~800 mg of Na—S-SSA in a low-pressure gas phase run at 120° ° C. using the conditions provided in Table 18. Following the 22 h reaction, the Na—S-SSA sample (800 mg) was divided into 4 batches of 200 mg each. The following extraction methods were investigated, each method used on one of the divided samples. Each extraction method consisted of eight repeated extractions (8 h each) carried out in a spinning basket extractor as detailed in Example 2 with different extraction media and operating temperature as follows.

Method 1. Method 1 involved a room temperature extraction with a water and THF mixture, using 15 mL of $H_2O$ and 15 mL of THF for eight extractions of eight hours each.

Method 2. Method 2 performed the extraction at 95° C. with $H_2O$ only, for eight extractions of eight hours each.

Method 3. This method utilized a pH 3 aqueous solution, acidified with $HNO_3$, at 95° C., for eight extractions of eight hours each.

Method 4. In this method, a pH 10 aqueous NaOH solution at 95° C. was used, for eight extractions of eight hours each.

A comparison of acrylic acid extraction using the various extraction methods is provided in the FIG. 7, showing the number of turnovers (TON) based on acrylic acid collected for each extraction cycle, and FIG. 8, showing the cumulative acrylic acid TON for all eight extraction cycles. Therefore, the data from FIG. 7 are plotted in terms of cumulative TON in FIG. 8. For example, extraction with the THF/$H_2O$ mixture (Method 1) for this 200 mg Na—S-SSA sample produces the expected TON of ~25, which is ¼ (one fourth) of the TON observed with 800 mg Na—S-SSA.

As seen in both FIG. 7 and FIG. 8, the TON with THF/$H_2O$ mixture (Method 1) increases sharply from a cumulative TON of ~3 after the third extraction step to a cumulative TON of ~7 after the fourth extraction step. While not intending to be theory-bound, it is believed that attaining an intermediate TON between 2 and 7 removes enough acrylate from the pores to alleviate pore diffusion limitations which cause an increase in the extraction rate until all of the acrylate has been extracted (corresponding to a TON of ~25).

Extraction with water alone at 95° C. (Method 2, FIG. 8) is considerably slower and produces a cumulative TON of only ~5-10, even after eight extraction cycles. This trend is more or less similar for the acidic and basic aqueous extraction media (Method 3 and Method 4, respectively) as well. While not theory bound, this observation may be attributed to the surface tension of water in the pores which make extraction difficult. As more acrylate is extracted in each cycle and the cumulative TON increases, the extraction rate also starts to increase in subsequent cycles. Therefore, it is possible that the sharp increase may occur after 9 or 10 cycles. Because THF reduces the surface tension of water, more acrylate can be extracted with THF present as in Method 1 as compared to water alone as solvent in Method 2. This observation may account for the sharp increase in TON with THF/$H_2O$ mix after 3 extraction cycles.

The surface area and pore volume of the fresh solid base, the spent solid following use in a reaction run, and samples following extractions of acrylate product using various protocols are summarized in Table 19. The decrease in surface area and pore volume following treatment of the solid support with the base (rows 2 and 3 of Table 19) are consistent with incorporation of the base. The values following extraction are somewhat scattered.

In these Example, a maximum turnover number (TON) of ~20 for acrylic acid (sodium acrylate) formation was achieved during a 20 h run at the following reaction conditions: $C_2H_4$/$CO_2$ (psig)=150/150 at 25° C., T=40° C., 5.6 mg (dcpe)NiLac in 30 mL THF, 700 mg Na—S-SSA]. These Examples also reveal that during this period, the (dcpe)NiLac complex impregnates itself into the MT-CMSO. The catalytic reaction appears to stop after about 20 h, but catalytic activity is recovered by a pressure-swing (release of reactor gas pressure to ambient conditions followed by repressurization). Following such pressure-swings every 20 h, acrylate formation continues to occur on the solid phase without any further (dcpe)NiLac addition for up to 80 h over which the reaction was investigated, reaching a TON of ~73. Under more extreme conditions such as higher temperatures and excess $CO_2$, (dcpe)NiLac was observed to undergo a second $CO_2$ insertion reaction into the nickelalactone nickel-carbon bond that resulted in the formation of a nickel(II) methyl malonate complex (dcpe)Ni(OC(O)$CH_2$$CH_2$C(O)O), where the —OC(O)$CH_2$$CH_2$C(O)O— ligand forms a metalacyclic structure with the nickel. If the desired product is the metal acrylate, this second insertion forming the methyl malonate complex diverts some of the catalyst toward the undesired product. This methyl malonate complex may be abbreviated herein as "(dcpe)NiM". While not intending to be bound by theory, it is believed that these results suggest that the overall acrylate formation rate in the liquid phase is constrained by pore diffusion limitations.

The invention is described above with reference to numerous aspects and embodiments, and specific examples. Many variations will suggest themselves to those skilled in the art in light of the above detailed description. All such obvious variations are within the full intended scope of the appended claims. Other aspects of the invention can include, but are not limited to, the following aspects. Many aspects are described as "comprising" certain components or steps, but alternatively, can "consist essentially of" or "consist of" those components or steps unless specifically stated otherwise.

Aspects of the Disclosure

Aspect 1. A process for preparing a catalyst composition, the process comprising contacting in any order:
  (i) a Group 8-11 transition metal precursor compound comprising at least one first ligand;
  (ii) optionally, at least one second ligand;
  (iii) a first olefin;

TABLE 19

Comparison of surface area/pore volume values of fresh and processed solid base

| | | | After extraction | | | |
|---|---|---|---|---|---|---|
| | S-SSA | Na—S-SSA | Method 1. THF/$H_2O$ at 30° C. | Method 2. $H_2O$ at 95 ° C. | Method 3. pH 3 $HNO_3$ (aq) | Method 4. pH 10 NaOH (aq) |
| Surface area ($m^2$/g) | | | | | | |
| Single point BET | 269.4 | 109.9 | 308.4 | 143.1 | 327.8 | 368.0 |
| Multi point BET | 280.5 | 118.8 | 316.8 | 145.1 | 335.5 | 377.5 |
| Pore volume (cc/g) | 1.11 | 0.70 | 1.21 | 0.63 | 1.26 | 1.40 |
| Average pore diameter (nm) | 15.9 | 23.4 | 15.2 | 17.5 | 15.1 | 14.8 |

(iv) carbon dioxide ($CO_2$);
(v) a diluent; and
(vi) [A] a metal-treated chemically-modified solid oxide, wherein the chemically-modified solid oxide comprises at least one solid oxide which has been treated with at least one electron-withdrawing anion or [B] a metal-treated solid oxide, to provide a first reaction mixture; wherein the contacting is optionally carried out at a total pressure greater than ambient pressure; and wherein at least a portion of the Group 8-11 transition metal is deposited on the metal-treated chemically-modified solid oxide or the metal-treated solid oxide to provide a catalyst composition.

Aspect 2. The process for preparing a catalyst composition according to Aspect 1, wherein the first reaction mixture comprises a metalalactone.

Aspect 3. The process for preparing a catalyst composition according to Aspect 2, wherein the first reaction mixture comprises an adduct of the metalalactone and the metal-treated chemically-modified solid oxide or the metal-treated solid oxide.

Aspect 4. A process for preparing a catalyst composition, the process comprising contacting in any order:
(i) a metalalactone compound comprising a Group 8-11 transition metal, a metalalactone moiety, and at least one ligand in addition to the metalalactone moiety;
(ii) a first olefin;
(iii) carbon dioxide ($CO_2$);
(iv) a diluent; and
(v) [A] a metal-treated chemically-modified solid oxide, wherein the chemically-modified solid oxide comprises at least one solid oxide which has been treated with at least one electron-withdrawing anion or [B] a metal-treated solid oxide, to provide a first reaction mixture; wherein the contacting is optionally carried out at a total pressure greater than ambient pressure, and wherein at least a portion of the Group 8-11 transition metal is deposited on the metal-treated chemically-modified solid oxide or the metal-treated solid oxide to provide a catalyst composition.

Aspect 5. The process for preparing a catalyst composition according to any of Aspects 1-4, wherein the first olefin comprises or is independently selected from ethylene, propylene, butene (e.g., 1-butene), pentene, hexene (e.g., 1-hexene), heptene, octene (e.g., 1-octene), or styrene.

Aspect 6. The process for forming an α,β-unsaturated carboxylic acid or a salt thereof according to any of Aspects 1-5, wherein the first reaction mixture is pressurized with $CO_2$ to a $CO_2$ partial pressure greater than ambient pressure.

Aspect 7. The process for forming an α,β-unsaturated carboxylic acid or a salt thereof according to any of Aspects 1-6, wherein if applicable, the first reaction mixture is pressurized with the first olefin to a total pressure greater than ambient pressure.

Aspect 8. The process for preparing a catalyst composition according to any of Aspects 1-7, further comprising the steps of releasing the pressure from the first reaction mixture if applicable, and removing the diluent from the first reaction mixture to provide the catalyst composition as a solid catalyst composition.

Aspect 9. The process for preparing a catalyst composition according to Aspect 8, wherein the solid catalyst composition (a) comprises less than 10 wt. %, less than 5 wt. %, less than 1 wt. %, or less than 0.5 wt. % diluent and/or (b) the solid catalyst composition comprises a free-flowing solid.

Aspect 10. A process for forming an α,β-unsaturated carboxylic acid or a salt thereof, the process comprising:
(a) contacting in any order (i) a Group 8-11 transition metal precursor compound comprising at least one first ligand, (ii) optionally, at least one second ligand, (iii) a first olefin, (iv) carbon dioxide ($CO_2$), (v) a diluent, and (vi) [A] a metal-treated chemically-modified solid oxide, wherein the chemically-modified solid oxide comprises at least one solid oxide which has been treated with at least one electron-withdrawing anion, or [B] a metal-treated solid oxide, to provide a first reaction mixture,
wherein the contacting is optionally carried out at a total pressure greater than ambient pressure, and
wherein at least a portion of the Group 8-11 transition metal is deposited on the metal-treated chemically-modified solid oxide or the metal-treated solid oxide;
(b) releasing the pressure from the first reaction mixture if applicable, and removing the diluent from the first reaction mixture to provide the catalyst composition as a solid catalyst composition; and
(c) contacting in any order (i) the solid catalyst composition, (ii) a second olefin, and (iii) carbon dioxide ($CO_2$) at a total pressure greater than ambient pressure to provide a second reaction mixture comprising an α,β-unsaturated carboxylic acid or a salt thereof.

Aspect 11. The process for forming an α,β-unsaturated carboxylic acid or a salt thereof according to Aspect 10, wherein the first reaction mixture or the second reaction mixture, independently, comprises a metalalactone.

Aspect 12. The process for forming an α,β-unsaturated carboxylic acid or a salt thereof according to Aspect 11, wherein the first reaction mixture or the second reaction mixture, independently, comprises an adduct of the metalalactone and the metal-treated chemically-modified solid oxide or the metal-treated solid oxide.

Aspect 13. A process for forming an α,β-unsaturated carboxylic acid or a salt thereof, the process comprising:
(a) contacting in any order (i) a Group 8-11 transition metal metalalactone compound comprising a metalalactone moiety and at least one ligand in addition to the metalalactone moiety, (ii) a first olefin, (iii) carbon dioxide ($CO_2$), (iv) a diluent, and (v) [A] a metal-treated chemically-modified solid oxide, wherein the chemically-modified solid oxide comprises at least one solid oxide which has been treated with at least one electron-withdrawing anion, or [B] a metal-treated solid oxide, to provide a first reaction mixture,
wherein the contacting is optionally carried out at a total pressure greater than ambient pressure, and
wherein at least a portion of the Group 8-11 transition metal metalalactone compound is deposited on the metal-treated chemically-modified solid oxide or the metal-treated solid oxide;
(b) releasing the pressure from the first reaction mixture if applicable, and removing the diluent from the first reaction mixture to provide the catalyst composition as a solid catalyst composition; and
(c) contacting in any order (i) the solid catalyst composition, (ii) the second olefin, and (iii) carbon dioxide ($CO_2$) at a total pressure greater than ambient pressure to provide a second reaction mixture comprising an α,β-unsaturated carboxylic acid or a salt thereof.

Aspect 14. The process for forming an α,β-unsaturated carboxylic acid or a salt thereof according to any of Aspects 10-13, further comprising the steps of:

(d) releasing at least a fraction of the total pressure from the second reaction mixture; and (e) contacting in any order (i) the solid catalyst composition, (ii) the second olefin, and (iii) carbon dioxide ($CO_2$) at a total pressure greater than ambient pressure to provide a subsequent reaction mixture comprising an α,β-unsaturated carboxylic acid or a salt thereof.

Aspect 15. The process for forming an α,β-unsaturated carboxylic acid or a salt thereof according to Aspect 14, further comprising the step of:

(f) repeating steps (d) and (e) any number of times, for example from 1 to 30 times, to provide further subsequent reaction mixtures comprising the α,β-unsaturated carboxylic acid or a salt thereof.

Aspect 16. The process for forming an α,β-unsaturated carboxylic acid or a salt thereof according to Aspect 15, wherein steps (d) and (e) are repeated 1, 2, 3, 4, 5, 6, 7, 8, 9, 10, 11, 12, 13, 14, 15, 16, 17, 18, 19, or 20 times.

Aspect 17. The process for forming an α,β-unsaturated carboxylic acid or a salt thereof according to any of Aspects 10-16, wherein the first reaction mixture is pressurized with $CO_2$ to a $CO_2$ partial pressure greater than ambient pressure.

Aspect 18. The process for forming an α,β-unsaturated carboxylic acid or a salt thereof according to any of Aspects 10-17, wherein if applicable, the first reaction mixture is pressurized with the first olefin to a total pressure greater than ambient pressure.

Aspect 19. The process for forming an α,β-unsaturated carboxylic acid or a salt thereof according to any of Aspects 10-18, wherein the solid catalyst composition comprises less than 10 wt. %, less than 5 wt. %, less than 1 wt. %, or less than 0.5 wt. % diluent and/or the solid catalyst composition comprises a free-flowing solid.

Aspect 20. The process for forming an α,β-unsaturated carboxylic acid or a salt thereof according to any of Aspects 10-19, wherein in each occurrence, the step of contacting the solid catalyst composition, the second olefin, and carbon dioxide ($CO_2$) independently is carried out in the substantial absence of a diluent other than the second olefin and carbon dioxide, and wherein in the substantial absence of a diluent (a) the solid catalyst composition resulting from removing the diluent from the first reaction mixture comprises less than 10 wt. %, less than 5 wt. %, less than 1 wt. %, or less than 0.5 wt. % diluent and/or (b) the solid catalyst composition comprises a free-flowing solid.

Aspect 21. The process for forming an α,β-unsaturated carboxylic acid or a salt thereof according to any of Aspects 10-19, wherein in each occurrence, the step of contacting the solid catalyst composition, the second olefin, and carbon dioxide ($CO_2$) independently is carried out in the presence of a diluent in addition to the second olefin and carbon dioxide.

Aspect 22. The process for forming an α,β-unsaturated carboxylic acid or a salt thereof according to any of Aspects 10-21, wherein the first olefin is the same as the second olefin.

Aspect 23. The process for forming an α,β-unsaturated carboxylic acid or a salt thereof according to any of Aspects 10-21, wherein the first olefin is different from the second olefin.

Aspect 24. The process for forming an α,β-unsaturated carboxylic acid or a salt thereof according to any of Aspects 10-21, wherein the first olefin and the second olefin independently comprise or independently are selected from, ethylene, propylene, butene (e.g., 1-butene), pentene, hexene (e.g., 1-hexene), heptene, octene (e.g., 1-octene), or styrene.

Aspect 25. The process for forming an α,β-unsaturated carboxylic acid or a salt thereof according to any of Aspects 10-21, wherein the first olefin and the second olefin are ethylene.

Aspect 26. The process for forming an α,β-unsaturated carboxylic acid or a salt thereof according to any of Aspects 10-21, wherein:

the first olefin is ethylene and the first reaction mixture is pressurized with ethylene to an ethylene partial pressure greater than ambient pressure; and the second olefin is selected from ethylene, propylene, butene (e.g., 1-butene), pentene, hexene (e.g., 1-hexene), heptene, octene (e.g., 1-octene), or styrene.

Aspect 27. The process for forming an α,β-unsaturated carboxylic acid or a salt thereof according to any of Aspects 10-26, wherein the α,β-unsaturated carboxylic acid or a salt thereof comprises any suitable α,β-unsaturated carboxylic acid, or any α,β-unsaturated carboxylic acid disclosed herein, or a salt thereof, e.g., acrylic acid, methacrylic acid, 2-ethylacrylic acid, cinnamic acid, sodium acrylate, potassium acrylate, magnesium acrylate, sodium (meth)acrylate, etc.

Aspect 28. The process for forming an α,β-unsaturated carboxylic acid or a salt thereof according to any of Aspects 10-27, wherein the process further comprises a step of isolating the α,β-unsaturated carboxylic acid, or the salt thereof, using any suitable separation/purification procedure or any separation/purification procedure disclosed herein, e.g., evaporation, distillation, chromatography, and the like.

Aspect 29. The process for forming an α,β-unsaturated carboxylic acid or a salt thereof according to any of Aspects 10-28, further comprising a step of monitoring the concentration of at least one component of the first reaction mixture, the second reaction mixture, or any subsequent reaction mixture.

Aspect 30. The process for preparing a catalyst composition or the process for forming an α,β-unsaturated carboxylic acid or a salt thereof according to any of the preceding Aspects where applicable, wherein the contacting step to provide the first reaction mixture further comprises pressurizing the first reaction mixture with carbon dioxide ($CO_2$) and, if applicable, the first olefin to a total pressure greater than ambient pressure.

Aspect 31. The process for forming an α,β-unsaturated carboxylic acid or a salt thereof according to any of Aspects 10-30 as applicable, wherein the contacting step to provide the first reaction mixture and the contacting step to provide the second reaction mixture are conducted under conditions selected independently from each other.

Aspect 32. The process for forming an α,β-unsaturated carboxylic acid or a salt thereof according to any of Aspects 10-31 as applicable, wherein the conditions for the contacting step to provide the first reaction mixture and the conditions for the contacting step to provide the second reaction mixture comprise at least one common condition.

Aspect 33. The process for forming an α,β-unsaturated carboxylic acid or a salt thereof according to any of Aspects 10-32 as applicable, wherein the conditions for the contacting step to provide the first reaction mixture and the conditions for the contacting step to provide the second reaction mixture comprise at least one of a temperature and a pressure which are the same.

Aspect 34. The process for preparing a catalyst composition or the process for forming an α,β-unsaturated carboxylic acid or a salt thereof according to any of the preceding Aspects where applicable, wherein the Group 8-11 transition metal precursor compound or the Group 8-11 transition metal metalalactone compound are present in the first reaction mixture at a concentration of from 0.01 mM (millimolar) to 5 mM; alternatively, from 0.05 mM to 3 mM; alternatively, from 0.075 mM to 2 mM; or alternatively, from 0.1 mM (millimolar) to 1 mM.

Aspect 35. The process for preparing a catalyst composition or the process for forming an α,β-unsaturated carboxylic acid or a salt thereof according to any of the preceding Aspects where applicable, wherein the first olefin is ethylene, the second olefin is ethylene, and the ethylene and carbon dioxide ($CO_2$) are contacted, independently, in an ethylene:$CO_2$ molar ratio of from 5:1 to 1:5, from 3:1 to 1:3, from 2:1 to 1:2, or about 1:1 in the first reaction mixture or the second reaction mixture.

Aspect 36. The process for preparing a catalyst composition or the process for forming an α,β-unsaturated carboxylic acid or a salt thereof according to any of the preceding Aspects where applicable, wherein:
(a) the first olefin is ethylene, and contacting the Group 8-11 transition metal precursor compound or the Group 8-11 transition metal metalalactone compound with the ethylene and carbon dioxide ($CO_2$) is conducted using a constant addition of the ethylene and the carbon dioxide to the first reaction mixture; and/or
(b) the second olefin is ethylene, and contacting the solid catalyst composition with the ethylene and carbon dioxide ($CO_2$) is conducted using a constant addition of the ethylene and the carbon dioxide to the second reaction mixture.

Aspect 37. The process for preparing a catalyst composition or the process for forming an α,β-unsaturated carboxylic acid or a salt thereof according to any of the preceding Aspects where applicable, wherein the contacting step conditions to provide the first reaction mixture and the contacting step conditions to provide the second reaction mixture, independently, further comprise pressurizing the first reaction mixture or the second reaction mixture with carbon dioxide ($CO_2$) to or at a $CO_2$ partial pressure using any suitable pressure of $CO_2$, or to or at any pressure of $CO_2$ disclosed herein, such as, for example, from 5 psig (34 KPa) to 2,000 psig (13,790 KPa), from 15 psig (103 KPa) to 750 psig (5,171 KPa), from 25 psig (172 KPa) to 250 psig (1,724 KPa), or from 50 psig (345 KPa) to 150 psig (1,034 KPa), and the like.

Aspect 38. The process for preparing a catalyst composition or the process for forming an α,β-unsaturated carboxylic acid or a salt thereof according to any of the preceding Aspects where applicable, wherein the first olefin is ethylene, and the contacting step conditions to provide the first reaction mixture and the contacting step conditions to provide the second reaction mixture, independently, further comprise pressurizing the first reaction mixture or the second reaction mixture with ethylene to or at an ethylene partial pressure using any suitable pressure of ethylene, or to or at any pressure of ethylene disclosed herein, such as, for example, from 5 psig (34 KPa) to 1,000 psig (6,895 KPa), from 15 psig (103 KPa) to 500 psig (3,447 KPa), from 25 psig (172 KPa) to 250 psig (1,724 KPa), or from 50 psig (345 KPa) to 150 psig (1,034 KPa), and the like.

Aspect 39. The process for preparing a catalyst composition or the process for forming an α,β-unsaturated carboxylic acid or a salt thereof according to any of the preceding Aspects where applicable, wherein the contacting step conditions to provide the first reaction mixture and the contacting step conditions to provide the second reaction mixture, independently, further comprise pressurizing the first reaction mixture or the second reaction mixture to a total pressure of carbon dioxide ($CO_2$) and the first olefin to or at any suitable total pressure, or at any total pressure disclosed herein, such as, for example, from 5 (34 KPa) to 3,000 psig (20,684 KPa), from 15 (103 KPa) to 1,500 psig (10,342 KPa), from 25 (172 KPa) to 750 psig (5,171 KPa), from 50 (345 KPa) to 500 psig (3,447 KPa), or from 75 (34 KPa) to 250 psig (1,723 KPa), and the like.

Aspect 40. The process for preparing a catalyst composition or the process for forming an α,β-unsaturated carboxylic acid or a salt thereof according to any of the preceding Aspects where applicable, wherein the contacting step conditions to provide the first reaction mixture and the contacting step conditions to provide the second reaction mixture, independently, further comprise heating the first reaction mixture or the second reaction mixture to or at any suitable temperature, such as for example to or at any temperature within a range of from 5° C. to 750° C., from 10° C. to 500° C., from 15° C. to 200° C., from 20° C. to 100° C., from 25° C. to 75° C., from 25° C. to 50° C., or the like.

Aspect 41. The process for preparing a catalyst composition or the process for forming an α,β-unsaturated carboxylic acid or a salt thereof according to any of the preceding Aspects where applicable, wherein the contacting step to provide the first reaction mixture is conducted for a time period of from 0.25 h (hour) to 1,000 h, from 1 h to 500 h, from 5 h to 250 hour, or from 10 h to 100 h, or for any time period sufficient to deposit at least a portion of the Group 8-11 transition metal precursor compound or at least a portion of the Group 8-11 transition metal metalalactone compound on the metal-treated chemically-modified solid oxide or the metal-treated solid oxide.

Aspect 42. The process for forming an α,β-unsaturated carboxylic acid or a salt thereof according to any of Aspects 10-41 as applicable, wherein the contacting step to provide the second reaction mixture is conducted for a time period of from 0.5 h (hour) to 1,000 h, from 2 h to 500 h, from 10 h to 250 hour, or from 20 h to 100 h, or for any time period sufficient to produce the α,β-unsaturated carboxylic acid or a salt thereof.

Aspect 43. The process for preparing a catalyst composition or the process for forming an α,β-unsaturated carboxylic acid or a salt thereof according to any of the preceding Aspects where applicable, further comprising the step of drying the solid catalyst composition following the steps of releasing the pressure if applicable, and removing the diluent from the reaction mixture.

Aspect 44. The process for preparing a catalyst composition or the process for forming an α,β-unsaturated carboxylic acid or a salt thereof according to any of Aspects 1-3, 5-12, and 14-43 as applicable, wherein in the contacting step to provide the first reaction mixture, a first portion of components selected from any of (i)-(vi) are pre-contacted to form a pre-contacted mixture, and wherein the pre-contacted mixture is subsequently contacted in any order with a second portion of components selected from rom any of (i)-(vi) which are not pre-contacted.

Aspect 45. The process for preparing a catalyst composition or the process for forming an α,β-unsaturated carboxylic acid or a salt thereof according to any of Aspects 4-9 and 13-43 as applicable, wherein in the contacting step to provide the first reaction mixture, a first portion of components selected from any of (i)-(v) are pre-contacted to form a pre-contacted mixture, and wherein the pre-contacted mixture is subsequently contacted in any order with a second portion of components selected from rom any of (i)-(v) which are not pre-contacted.

Aspect 46. The process for preparing a catalyst composition or the process for forming an α,β-unsaturated carboxylic acid or a salt thereof according to any of Aspects 1-3, 5-12, and 14-44 as applicable, wherein the contacting step comprises contacting the Group 8-11 transition metal precursor compound with the at least one second ligand.

Aspect 47. The process for preparing a catalyst composition or the process for forming an α,β-unsaturated carboxylic acid or a salt thereof according to any of Aspects 1-3, 5-12, 14-44, and 46 as applicable, wherein the contacting step to provide the first reaction mixture comprises contacting in any order (i) the Group 8-11 transition metal precursor compound, (ii) the at least one second ligand, (v) the diluent, and (vi) [A] the metal-treated chemically-modified solid oxide or [B] the metal-treated solid oxide to form a pre-contacted mixture, followed by contacting the pre-contacted mixture with the remaining components (iii)-(iv) in any order to provide the first reaction mixture.

Aspect 48. The process for preparing a catalyst composition or the process for forming an α,β-unsaturated carboxylic acid or a salt thereof according to any of Aspects 4-9, 13-43, and 45 as applicable, wherein the contacting step to provide the first reaction mixture comprises contacting in any order (i) the Group 8-11 transition metal metalalactone compound and at least one ligand in addition to the metalalactone moiety, (iv) the diluent, and (v) [A] the metal-treated chemically-modified solid oxide or [B] the metal-treated solid oxide to provide a pre-contacted mixture, followed by contacting the pre-contacted mixture with the remaining components (ii)-(iii) in any order to provide the first reaction mixture.

Aspect 49. The process for forming an α,β-unsaturated carboxylic acid or a salt thereof according to any of Aspects 10-48 as applicable, wherein the process further comprises regenerating the metal-treated chemically-modified solid oxide or the metal-treated solid oxide following the formation of the α,β-unsaturated carboxylic acid or a salt thereof by contacting the chemically-modified solid oxide or the metal-treated solid oxide with (a) a metal-containing base, (b) a metal-containing salt, or (c) a metal-containing salt in combination with a non-metal-containing base to form a regenerated metal-treated chemically-modified solid oxide or the regenerated metal-treated solid oxide.

Aspect 50. The process for preparing a catalyst composition or the process for forming an α,β-unsaturated carboxylic acid or a salt thereof according to Aspect 49, further comprising a step of washing the regenerated metal-treated chemically-modified solid oxide or the regenerated metal-treated solid oxide with a solvent or the diluent.

Aspect 51. The process for preparing a catalyst composition or the process for forming an α,β-unsaturated carboxylic acid or a salt thereof according to any of Aspects 49-50, further comprising a step of drying the regenerated metal-treated chemically-modified solid oxide or the regenerated metal-treated solid oxide under vacuum or at atmosphere pressure.

Aspect 52. The process for preparing a catalyst composition or the process for forming an α,β-unsaturated carboxylic acid or a salt thereof according to any of the preceding Aspects where applicable, wherein the contacting step to provide the first reaction mixture and the contacting step to provide the second reaction mixture, independently, further comprise contacting the first reaction mixture or the second reaction mixture with any suitable solvent or diluent, or any solvent or diluent disclosed herein, e.g., carbonyl-containing solvents such as ketones, esters, amides, etc. (e.g., acetone, ethyl acetate, N,N-dimethylformamide), alcohols, water, etc., or combinations thereof.

Aspect 53. A process for forming an α,β-unsaturated carboxylic acid or a salt thereof, the process comprising:
(a) contacting in any order (i) a Group 8-11 transition metal precursor compound comprising at least one first ligand, (ii) optionally, at least one second ligand, (iii) a first olefin, (iv) carbon dioxide ($CO_2$), (v) a diluent, and (vi) [A] a metal-treated chemically-modified solid oxide, wherein the chemically-modified solid oxide comprises at least one solid oxide which has been treated with at least one electron-withdrawing anion, or [B] a metal-treated solid oxide, to provide a first reaction mixture;
(b) pressurizing the first reaction mixture with carbon dioxide ($CO_2$) and, if applicable, the first olefin to a total pressure greater than ambient pressure to produce an α,β-unsaturated carboxylic acid or a salt thereof;
(c) releasing at least a fraction of the total pressure from the first reaction mixture to provide a second reaction mixture; and
(d) repressurizing the second reaction mixture with carbon dioxide ($CO_2$) and, if applicable, the first olefin to a total pressure greater than ambient pressure to produce additional α,β-unsaturated carboxylic acid or a salt thereof.

Aspect 54. A process for forming an α,β-unsaturated carboxylic acid or a salt thereof, the process comprising:
(a) contacting in any order (i) a Group 8-11 transition metal metalalactone compound comprising a metalalactone moiety and at least one ligand in addition to the metalalactone moiety, (ii) a first olefin, (iii) carbon dioxide ($CO_2$), (iv) a diluent, and (v) [A] a metal-treated chemically-modified solid oxide, wherein the chemically-modified solid oxide comprises at least one solid oxide which has been treated with at least one electron-withdrawing anion, or [B] a metal-treated solid oxide to provide a first reaction mixture;
(b) pressurizing the first reaction mixture with carbon dioxide ($CO_2$) and, if applicable, the first olefin to a total pressure greater than ambient pressure to produce an α,β-unsaturated carboxylic acid or a salt thereof;
(c) releasing at least a fraction of the total pressure from the first reaction mixture to provide a second reaction mixture; and
(d) repressurizing the second reaction mixture with carbon dioxide ($CO_2$) and, if applicable, the first olefin to a total pressure greater than ambient pressure to produce additional α,β-unsaturated carboxylic acid or a salt thereof.

Aspect 55. The process for forming an α,β-unsaturated carboxylic acid or a salt thereof according to any of Aspects 53-54, further comprising the steps of:
(e) releasing at least a fraction of the total pressure from the second reaction mixture to provide a subsequent reaction mixture; and
(f) repressurizing the subsequent reaction mixture with carbon dioxide ($CO_2$) and, if applicable, the first olefin to a total pressure greater than ambient pressure to produce additional α,β-unsaturated carboxylic acid or a salt thereof.

Aspect 56. The process for forming an α,β-unsaturated carboxylic acid or a salt thereof according to Aspect 55, further comprising the step of:
(g) repeating steps (e) and (f) any number of times, for example from 1 to 30 times, to provide further subsequent reaction mixtures and to produce the α,β-unsaturated carboxylic acid or a salt thereof.

Aspect 57. The process for forming an α,β-unsaturated carboxylic acid or a salt thereof according to Aspect 56, wherein steps (e) and (f) are repeated 1, 2, 3, 4, 5, 6, 7, 8, 9, 10, 11, 12, 13, 14, 15, 16, 17, 18, 19, or 20 times.

Aspect 58. A process for forming an α,β-unsaturated carboxylic acid or a salt thereof according to any of Aspects 53-57, wherein the step of releasing at least a fraction of the pressure from the first reaction mixture or the step of releasing at least a fraction of the pressure from the second reaction mixture, independently, does not remove all of the diluent from the first reaction mixture or the second reaction mixture, respectively.

Aspect 59. A process for forming an α,β-unsaturated carboxylic acid or a salt thereof according to any of Aspects 53-58, wherein the step of releasing at least a fraction of the pressure from the first reaction mixture or the step of releasing at least a fraction of the pressure from the second reaction mixture, independently, removes less than 20 wt. %, less than 10 wt. %, less than 5 wt. %, or less than 2 wt. % of the diluent from the first reaction mixture or the second reaction mixture, respectively.

Aspect 60. A process for forming an α,β-unsaturated carboxylic acid or a salt thereof according to any of Aspects 53-59, wherein the step of releasing at least a fraction of the pressure from the first reaction mixture or the step of releasing at least a fraction of the pressure from the second reaction mixture, independently, does not release the pressure to ambient pressure.

Aspect 61. A process for forming an α,β-unsaturated carboxylic acid or a salt thereof according to any of Aspects 53-59, wherein the step of releasing at least a fraction of the pressure from the first reaction mixture or the step of releasing at least a fraction of the pressure from the second reaction mixture, independently, releases the pressure to ambient pressure.

Aspect 62. A catalyst system for producing an α,β-unsaturated carboxylic acid or a salt thereof, the catalyst system comprising:
  (a) a Group 8-11 transition metal precursor compound comprising at least one first ligand and/or at least one second ligand; and
  (b) (i) a metal-treated chemically-modified solid oxide, wherein the chemically-modified solid oxide comprises at least one solid oxide which has been treated with at least one electron-withdrawing anion or (ii) a metal-treated solid oxide;
  wherein at least a portion of Group 8-11 transition metal precursor compound is deposited on the metal-treated chemically-modified solid oxide or the metal-treated solid oxide.

Aspect 63. A catalyst system for producing an α,β-unsaturated carboxylic acid or a salt thereof, the solid catalyst system comprising:
  (a) a Group 8-11 transition metal metalalactone compound comprising a metalalactone moiety and at least one ligand in addition to the metalalactone moiety; and
  (b) (i) a metal-treated chemically-modified solid oxide, wherein the chemically-modified solid oxide comprises at least one solid oxide which has been treated with at least one electron-withdrawing anion or (ii) a metal-treated solid oxide;
  wherein at least a portion of Group 8-11 transition metal metalalactone compound is deposited on the metal-treated chemically-modified solid oxide or the metal-treated solid oxide.

Aspect 64. The catalyst system for producing an α,β-unsaturated carboxylic acid or a salt thereof according to any of Aspects 62-63, wherein the catalyst system comprises (a) a solid which comprises less than 10 wt. %, less than 5 wt. %, less than 1 wt. %, or less than 0.5 wt. % diluent and/or (b) a free-flowing solid.

Aspect 65. The catalyst system for producing an α,β-unsaturated carboxylic acid or a salt thereof according to Aspect 64, wherein the solid comprises less than 1 wt. % diluent.

Aspect 66. The catalyst system for producing an α,β-unsaturated carboxylic acid or a salt thereof according to any of Aspects 62-63, wherein the catalyst system further comprises a diluent.

Aspect 67. A catalyst system for producing an α,β-unsaturated carboxylic acid or a salt thereof, the catalyst system comprising the contact product of, or the catalyst system prepared by contacting:
  (i) a Group 8-11 transition metal precursor compound comprising at least one first ligand;
  (ii) optionally, at least one second ligand;
  (iii) a first olefin such as ethylene;
  (iv) carbon dioxide ($CO_2$);
  (v) a diluent; and
  (vi) [A] a metal-treated chemically-modified solid oxide, wherein the chemically-modified solid oxide comprises at least one solid oxide which has been treated with at least one electron-withdrawing anion or [B] a metal-treated solid oxide.

Aspect 68. A catalyst system for producing an α,β-unsaturated carboxylic acid or a salt thereof, the catalyst system comprising the contact product of, or the catalyst system prepared by contacting:
  (i) a Group 8-11 transition metal metalalactone compound comprising a metalalactone moiety and at least one ligand in addition to the metalalactone moiety;
  (ii) optionally, a first olefin such as ethylene;
  (iii) optionally, carbon dioxide ($CO_2$);
  (iv) a diluent; and
  (v) [A] a metal-treated chemically-modified solid oxide, wherein the chemically-modified solid oxide comprises at least one solid oxide which has been treated with at least one electron-withdrawing anion, or [B] a metal-treated solid oxide;

Aspect 69. The catalyst system according to Aspect 68, wherein the catalyst system comprises the contact product of, or the catalyst system is prepared by contacting (ii) the first olefin, such as ethylene and (iii) carbon dioxide ($CO_2$), that is, the optional first olefin and the optional carbon dioxide ($CO_2$) are present.

Aspect 70. The catalyst system for producing an α,β-unsaturated carboxylic acid or a salt thereof, according to any of Aspects 67-69, wherein the first olefin is independently selected from ethylene, propylene, butene (e.g., 1-butene), pentene, hexene (e.g., 1-hexene), heptene, octene (e.g., 1-octene), or styrene.

Aspect 71. The catalyst system for producing an α,β-unsaturated carboxylic acid or a salt thereof, according to any of Aspects 67-70, wherein at least a portion of the Group 8-11 transition metal precursor compound or the Group 8-11 transition metal metalalactone compound is deposited on the metal-treated chemically-modified solid oxide or the metal-treated solid oxide.

Aspect 72. The catalyst system for producing an α,β-unsaturated carboxylic acid or a salt thereof, according to any of Aspects 67-71, wherein the diluent is substantially removed from the contact product (or further comprising the step of substantially removing the diluent from the contact product), following the step of contacting, and the catalyst system comprises (a) a solid which is substantially absent the diluent (comprising less than less than 10 wt. %, less than 5 wt. %, or less than 1 wt. % diluent) and/or (b) a free-flowing solid.

Aspect 73. The process for preparing a catalyst composition, the process for forming an α,β-unsaturated carboxylic acid or a salt thereof, or the catalyst system according to any of Aspects 1-72, wherein the metal of the Group 8-11 transition metal precursor compound or the metal of the Group 8-11 transition metal metalalactone compound is a Group 8 metal.

Aspect 74. The process for preparing a catalyst composition, the process for forming an α,β-unsaturated carboxylic acid or a salt thereof, or the catalyst system according any of Aspects 1-72, wherein the metal of the Group 8-11 transition metal precursor compound or the metal of the Group 8-11 transition metal metalalactone compound is a Group 9 metal.

Aspect 75. The process for preparing a catalyst composition, the process for forming an α,β-unsaturated carboxylic acid or a salt thereof, or the catalyst system according to any of Aspects 1-72, wherein the metal of the Group 8-11 transition metal precursor compound or the metal of the Group 8-11 transition metal metalalactone compound is a Group 10 metal.

Aspect 76. The process for preparing a catalyst composition, the process for forming an α,β-unsaturated carboxylic acid or a salt thereof, or the catalyst system according to any of Aspects 1-72, wherein the metal of the Group 8-11 transition metal precursor compound or the metal of the Group 8-11 transition metal metalalactone compound is a Group 11 metal.

Aspect 77. The process for preparing a catalyst composition, the process for forming an α,β-unsaturated carboxylic acid or a salt thereof, or the catalyst system according to any of Aspects 1-72, wherein the metal of the Group 8-11 transition metal precursor compound or the metal of the Group 8-11 transition metal metalalactone compound is selected from Fe, Co, Ni, Cu, Ru, Rh, Pd, Ir, or Pt.

Aspect 78. The process for preparing a catalyst composition, the process for forming an α,β-unsaturated carboxylic acid or a salt thereof, or the catalyst system according to any of Aspects 1-72, wherein the metal of the Group 8-11 transition metal precursor compound or the metal of the Group 8-11 transition metal metalalactone compound is Ni.

Aspect 79. The process for preparing a catalyst composition, the process for forming an α,β-unsaturated carboxylic acid or a salt thereof, or the catalyst system according to any of the preceding Aspects where applicable, wherein the first ligand, the second ligand, and the ligand in addition to the metalalactone moiety are, independently, any suitable neutral electron donor group and/or Lewis base, or any neutral electron donor group and/or Lewis base disclosed herein.

Aspect 80. The process for preparing a catalyst composition, the process for forming an α,β-unsaturated carboxylic acid or a salt thereof, or the catalyst system according to any of the preceding Aspects where applicable, wherein the first ligand, the second ligand, or the ligand in addition to the metalalactone moiety are, independently, a bidentate ligand.

Aspect 81. The process for preparing a catalyst composition, the process for forming an α,β-unsaturated carboxylic acid or a salt thereof, or the catalyst system according to any of the preceding Aspects where applicable, wherein the first ligand, the second ligand, or the ligand in addition to the metalalactone moiety, independently, comprise at least one of a nitrogen, phosphorus, sulfur, or oxygen heteroatom, or a combination thereof.

Aspect 82. The process for preparing a catalyst composition, the process for forming an α,β-unsaturated carboxylic acid or a salt thereof, or the catalyst system according to any of the preceding Aspects where applicable, wherein the first ligand, the second ligand, or the ligand in addition to the metalalactone moiety, independently, comprise or are selected from a diphosphine ligand, a diamine ligand, a diene ligand, a diether ligand, or dithioether ligand.

Aspect 83. The process for preparing a catalyst composition, the process for forming an α,β-unsaturated carboxylic acid or a salt thereof, or the catalyst system according to any of the preceding Aspects where applicable, wherein the first ligand, the second ligand, or the ligand in addition to the metalalactone moiety, independently, comprise or are selected from an ether ligand, an organic carbonyl ligand, a thioether ligand, an amine ligand, a nitrile ligand, a phosphine ligand, a diene ligand, or a carbene ligand.

Aspect 84. The process for preparing a catalyst composition, the process for forming an α,β-unsaturated carboxylic acid or a salt thereof, or the catalyst system according to any of the preceding Aspects where applicable, wherein first ligand is a diene ligand and the second ligand or the ligand in addition to the metalalactone moiety is a diphosphine ligand.

Aspect 85. The process for preparing a catalyst composition, the process for forming an α,β-unsaturated carboxylic acid or a salt thereof, or the catalyst system according to any of the preceding Aspects where applicable, wherein the first ligand, the second ligand, or the ligand in addition to the metalalactone moiety, independently, comprise or are selected from trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, tricyclohexylphosphine, trimethyl phosphite, triethyl phosphite, tripropyl phosphite, triisopropyl phosphite, tributyl phosphite and tricyclohexyl phosphite, 2-(di-t-butylphosphino)biphenyl, 2-di-t-butylphosphino-1,1'-binaphthyl, 2-(di-t-butylphosphino)-3,6-dimethoxy-2',4',6'-tri-i-propyl-1,1'-biphenyl, 2-(di-t-butylphosphino-2'-methylbiphenyl, 2-(di-t-butylphosphinomethyl)pyridine, 2-di-t-butylphosphino-2',4',6'-tri-i-propyl-1,1'-biphenyl, 2-(dicyclohexylphosphino)biphenyl, (S)-(+)-(3,5-dioxa-4-phospha-cyclohepta[2,1-a;3,4-a']dinaphthalen-4-yl)dimethylamine, 2-(diphenylphosphino)-2'-methoxy-1,1'-binaphthyl, 1,2,3,4,5-pentaphenyl-1'-(di-t-butylphosphino)ferrocene, 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(di-t-butyl-phosphino)ethane, 1,2-bis(dicyclohexylphosphino)ethane, 1,3-bis(dicyclohexylphosphino)propane, 1,4-bis(dicyclohexylphosphino)butane, 1,3-bis(diisopropylphosphino)propane, 1,3-bis(diphenylphosphino)propane, 1,3-bis(di-t-butylphosphino)propane, 1,4-bis(diisopropylphosphino)butane, 1,4-bis(diphenylphosphino)butane, 2,2'-bis[bis(3,5-dimethylphenyl)phosphino]-4,4',6,6'-tetramethoxybiphenyl, 2,6-bis(di-t-butylphosphinomethyl)pyridine, 2,2'-bis(dicyclohexylphosphino)-1,1'-biphenyl, bis(2-dicyclohexylphosphinophenyl)ether, 5,5'-bis(diphenylphosphino)-4,4'-bi-1,3- benzodioxole, 2-t-butylphosphinomethylpyridine, bis(diphenylphosphino)ferrocene, bis(diphenylphosphino)methane, bis(dicyclohexylphosphino)methane, bis(di-t-butylphosphino)methane, or TMEDA.

Aspect 86. The process for preparing a catalyst composition, the process for forming an α,β-unsaturated carboxylic acid or a salt thereof, or the catalyst system according to any of the preceding Aspects where applicable, wherein the first ligand, the second ligand, or the ligand in addition to the metalalactone moiety, independently, comprise or are selected from

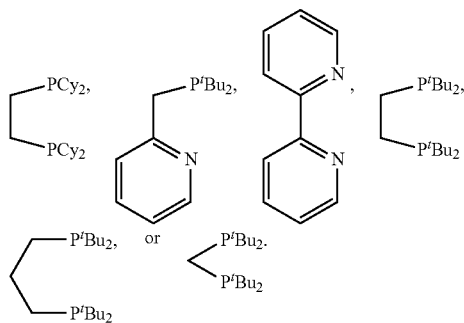

Aspect 87. The process for preparing a catalyst composition, the process for forming an α,β-unsaturated carboxylic acid or a salt thereof, or the catalyst system according to any of the preceding Aspects where applicable, wherein the first ligand, the second ligand, or the ligand in addition to the metalalactone moiety, independently, comprise or are selected from:
(1R,1'R,2S,2'S)-2,2'-Di-tert-butyl-2,3,2',3'-tetrahydro-1H,1'H-(1,1')biisophosphindolyl (also designated (1R,1'R,2S,2'S)-DuanPhos or simply DuanPhos in the structures provided herein);
(3S,3'S,4S,4'S,11bS,11'bS)-(+)-4,4'-Di-t-butyl-4,4',5,5'-tetrahydro-3,3'-bi-3H-dinaphtho[2,1-c:1',2'-e]phosphepin (also designated (S)-BINAPINE or simply Binapine in the structures provided herein);
(1S,1S',2R,2R')-1,1'-Di-tert-butyl-(2,2')-diphospholane (also designated (S,S',R,R')-TangPhos or simply TangPhos in the structures provided herein);
(−)-1,2-Bis[(2S,5S)-2,5-diisopropylphospholano]benzene (also designated (S,S)-i-Pr-DUPHOS or simply iPr-DUPHOS in the structures provided herein);
(+)-1,2-Bis[(2R,5R)-2,5-diisopropylphospholano]benzene (also designated (R,R)-i-Pr-DUPHOS);
a racemic mixture of (S,S)-i-Pr-DUPHOS and (R,R)-i-Pr-DUPHOS);
(−)-1,2-Bis[(2S,5S)-2,5-dimethylphospholano]benzene (also designated (S,S)-Me-DUPHOS);
(+)-1,2-Bis[(2R,5R)-2,5-dimethylphospholano]benzene (also designated (R,R)-Me-DUPHOS or simply Me-DUPHOS in the structures provided herein);
A racemic mixture of (S,S)-Me-DUPHOS) and (R,R)-Me-DUPHOS;
(R,R)-(−)-2,3-Bis(tert-butylmethylphosphino)quinoxaline (also designated (R)-QuinoxP or simply QuinoxP in the structures provided herein); or
(R,R)-(+)-1,2-Bis(t-butylmethylphosphino)benzene (also designated (R,R)-BenzP* or simply BenzP* in the structures provided herein).

Aspect 88. The process for preparing a catalyst composition, the process for forming an α,β-unsaturated carboxylic acid or a salt thereof, or the catalyst system according to any of the preceding Aspects where applicable, wherein the first ligand is 1,5-cyclooctadiene or TMEDA, and the second ligand or the ligand in addition to the metalalactone moiety is 1,2-bis(dicyclohexylphosphino)ethane or TMEDA.

Aspect 89. The process for preparing a catalyst composition, the process for forming an α,β-unsaturated carboxylic acid or a salt thereof, or the catalyst system according to any of the preceding Aspects where applicable, wherein the solid oxide of [A] the metal-treated chemically-modified solid oxide or [B] the metal-treated solid oxide comprises or is selected from $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, $Na_2O$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, $K_2O$, CaO, $La_2O_3$, $Ce_2O_3$, mixtures thereof, mixed oxides thereof (for example, silica-alumina), and any combinations thereof.

Aspect 90. The process for preparing a catalyst composition, the process for forming an α,β-unsaturated carboxylic acid or a salt thereof, or the catalyst system according to any of the preceding Aspects where applicable, wherein the solid oxide of [A] the metal-treated chemically-modified solid oxide or [B] the metal-treated solid oxide comprises or is selected from silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, heteropolytungstate, a mixed oxide thereof, or any combination thereof.

Aspect 91. The process for preparing a catalyst composition, the process for forming an α,β-unsaturated carboxylic acid or a salt thereof, or the catalyst system according to any of the preceding Aspects where applicable, wherein the solid oxide of [A] the metal-treated chemically-modified solid oxide or [B] the metal-treated solid oxide comprises or is selected from a silica, a silicate, or an aluminosilicate.

Aspect 92. The process for preparing a catalyst composition, the process for forming an α,β-unsaturated carboxylic acid or a salt thereof, or the catalyst system according to any of the preceding Aspects where applicable, wherein the solid oxide of [A] the metal-treated chemically-modified solid oxide or [B] the metal-treated solid oxide comprises or is selected from a mesoporous silica, a mesostructured cellular foam (MCF) silica, a molecular sieve, a zeolite, or any combination thereof.

Aspect 93. The process for preparing a catalyst composition, the process for forming an α,β-unsaturated carboxylic acid or a salt thereof, or the catalyst system according to any of the preceding Aspects where applicable, wherein the solid oxide of [A] the metal-treated chemically-modified solid oxide or [B] the metal-treated solid oxide comprises or is selected from Na-MCM-41, Na/Al-KIT-6, Na—Y zeolite, Na-SBA-15, Na-treated trimodal porous silica (TMS), potassium L-zeolite, or any combination thereof.

Aspect 94. The process for preparing a catalyst composition, the process for forming an α,β-unsaturated carboxylic acid or a salt thereof, or the catalyst system according to any of the preceding Aspects where applicable, wherein the chemically-modified solid oxide is generated by treatment of a solid oxide with an acid of an electron-withdrawing anion, a salt of an electron-withdrawing anion, or a combination thereof.

Aspect 95. The process for preparing a catalyst composition, the process for forming an α,β-unsaturated carboxylic acid or a salt thereof, or the catalyst system according to any of the preceding Aspects where applicable, wherein following treatment of the solid oxide with an electron-withdrawing anion, the chemically-modified solid oxide is dried and calcined.

Aspect 96. The process for preparing a catalyst composition, the process for forming an α,β-unsaturated carboxylic acid or a salt thereof, or the catalyst system according to any of the preceding Aspects where applicable, wherein the chemically-modified solid oxide is produced by a process comprising contacting any suitable solid oxide and any suitable solid oxide with an electron-withdrawing anion to provide a contact product, and concurrently and/or subsequently drying and/or calcining the contact product.

Aspect 97. The process for preparing a catalyst composition, the process for forming an α,β-unsaturated carboxylic acid or a salt thereof, or the catalyst system according to any of the preceding Aspects where applicable, wherein the electron-withdrawing anion comprises or is selected from sulfate, bisulfate, fluorosulfate, phosphate, fluorophosphate, triflate, mesylate, tosylate, thiosulfate, $C_1$-$C_{10}$ alkyl sulfonate, $C_6$-$C_{14}$ aryl sulfonate, fluoride, chloride, or any combination thereof.

Aspect 98. The process for preparing a catalyst composition, the process for forming an α,β-unsaturated carboxylic acid or a salt thereof, or the catalyst system according to any of the preceding Aspects where applicable, wherein the chemically-modified solid oxide is generated by treatment of a solid oxide with sulfuric acid, sulfate ion, bisulfate ion, fluorosulfuric acid, fluorosulfate ion, phosphoric acid, phosphate ion, fluorophosphoric acid, monofluorophosphate ion, triflic (trifluoromethanesulfonic) acid, triflate trifluoromethanesulfonate) ion, methanesulfonic acid, mesylate (methanesulfonate) ion, toluenesulfonic acid, tosylate (toluenesulfonate) ion, thiosulfate ion, $C_1$-$C_{10}$ alkyl sulfonic acid, $C_1$-$C_{10}$ alkyl sulfonate ion, $C_6$-$C_{14}$ aryl sulfonic acid, $C_6$-$C_{14}$ aryl sulfonate ion, fluoride ion, chloride ion, or any combination thereof.

Aspect 99. The process for preparing a catalyst composition, the process for forming an α,β-unsaturated carboxylic acid or a salt thereof, or the catalyst system according to any of the preceding Aspects where applicable, wherein the chemically-modified solid oxide comprises a sulfur oxoacid anion-modified solid oxide, a phosphorus oxoacid anion-modified solid oxide, or a halide ion-modified solid oxide.

Aspect 100. The process for preparing a catalyst composition, the process for forming an α,β-unsaturated carboxylic acid or a salt thereof, or the catalyst system according to any of the preceding Aspects where applicable, wherein the chemically-modified solid oxide comprises a sulfated solid oxide, bisulfated (hydrogen sulfated) solid oxide, fluorosulfated solid oxide, phosphated solid oxide, fluorophosphated solid oxide, fluorided solid oxide, or chlorided solid oxide.

Aspect 101. The process for preparing a catalyst composition, the process for forming an α,β-unsaturated carboxylic acid or a salt thereof, or the catalyst system according to any of the preceding Aspects where applicable, wherein the chemically-modified solid oxide comprises a sulfated solid oxide or a phosphated solid oxide.

Aspect 102. The process for preparing a catalyst composition, the process for forming an α,β-unsaturated carboxylic acid or a salt thereof, or the catalyst system according to any of the preceding Aspects where applicable, wherein the chemically-modified solid oxide comprises a sulfur oxoacid anion-modified solid oxide generated by sulfuric acid treatment or sulfate ion treatment.

Aspect 103. The process for preparing a catalyst composition, the process for forming an α,β-unsaturated carboxylic acid or a salt thereof, or the catalyst system according to any of the preceding Aspects where applicable, wherein the chemically-modified solid oxide comprises a phosphorus oxoacid anion-modified solid oxide generated by phosphoric acid treatment or phosphate ion treatment.

Aspect 104. The process for preparing a catalyst composition, the process for forming an α,β-unsaturated carboxylic acid or a salt thereof, or the catalyst system according to any of the preceding Aspects where applicable, wherein the chemically-modified solid oxide comprises a sulfated solid oxide.

Aspect 105. The process for preparing a catalyst composition, the process for forming an α,β-unsaturated carboxylic acid or a salt thereof, or the catalyst system according to any of the preceding Aspects where applicable, wherein the chemically-modified solid oxide comprises a solid oxide that is chemically-modified with an electron-withdrawing anion, wherein:

the solid oxide comprises or is selected from silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof; and the electron-withdrawing anion comprises or is selected from sulfate, bisulfate, fluorosulfate, phosphate, fluorophosphates, fluoride, or chloride.

Aspect 106. The process for preparing a catalyst composition, the process for forming an α,β-unsaturated carboxylic acid or a salt thereof, or the catalyst system according to any of the preceding Aspects where applicable, wherein:

the chemically-modified solid oxide comprises a solid oxide comprising or selected from alumina, silica-alumina, silica-coated alumina, or a mixture thereof, and the electron-withdrawing anion comprises or is selected from sulfate, phosphate, or fluoride.

Aspect 107. The process for preparing a catalyst composition, the process for forming an α,β-unsaturated carboxylic acid or a salt thereof, or the catalyst system according to any of the preceding Aspects where applicable, wherein the sulfur oxoacid anion is provided by a sulfur oxoacid or a sulfur oxoacid salt, the phosphorus oxoacid anion is provided by a phosphorus oxoacid or a phosphorus oxoacid salt, and the halide ion is provided by a hydrohalic acid or a halide salt.

Aspect 108. The process for preparing a catalyst composition, the process for forming an α,β-unsaturated carboxylic acid or a salt thereof, or the catalyst system according to any of the preceding Aspects where applicable, wherein the sulfur oxoacid anion is provided sulfuric acid or a sulfate salt, the phosphorus oxoacid anion is provided by phosphoric acid or a phosphate salt, and the halide ion is provided by a hydrochloric acid, hydrofluoric acid, a chloride salt, or a fluoride salt.

Aspect 109. The process for preparing a catalyst composition, the process for forming an α,β-unsaturated carboxylic acid or a salt thereof, or the catalyst system according to any of the preceding Aspects where applicable, wherein the metal-treated chemically-modified solid oxide is prepared by (a) contacting a solid oxide with a sulfur oxoacid anion, a phosphorus oxoacid anion, or a halide ion to provide the chemically-modified solid oxide, followed by (b) contacting the chemically-modified solid oxide with (i) a metal-containing base or (ii) a metal-containing salt in combination with a non-metal containing base.

Aspect 110. The process for preparing a catalyst composition, the process for forming an α,β-unsaturated carboxylic acid or a salt thereof, or the catalyst system according to any of the preceding Aspects where applicable, wherein the metal-treated chemically-modified solid oxide is produced by a process comprising contacting any suitable solid oxide with an electron-withdrawing anion to form a first mixture and concurrently and/or subsequently drying and/or calcining the first mixture, followed by contacting the dried and/or calcined first mixture with any suitable metal-containing base to provide a second mixture, and concurrently and/or subsequently drying and/or calcining the second mixture.

Aspect 111. The process for preparing a catalyst composition, the process for forming an α,β-unsaturated carboxylic acid or a salt thereof, or the catalyst system according to any of the preceding Aspects where applicable, wherein the metal-treated chemically-modified solid oxide comprises a metal in a concentration of from 1 wt. % to 35 wt. %, from 2 wt. % to 30 wt. %, from 3 wt. % to 25 wt. %, or from 5 wt. % to 20 wt. %, based on the total weight of the metal-treated chemically-modified solid oxide.

Aspect 112. The process for preparing a catalyst composition, the process for forming an α,β-unsaturated carboxylic acid or a salt thereof, or the catalyst system according to any of the preceding Aspects where applicable, wherein [A] the metal-treated chemically-modified solid oxide or [B] the metal-treated solid oxide is prepared by contacting the chemically-modified solid oxide or the solid oxide, respectively, with (a) a metal-containing base, (b) a metal-containing salt in combination with a non-metal containing base, or (c) a metal-containing salt.

Aspect 113. The process for preparing a catalyst composition, the process for forming an α,β-unsaturated carboxylic acid or a salt thereof, or the catalyst system according to any of the preceding Aspects where applicable, wherein [A] the metal-treated chemically-modified solid oxide or [B] the metal-treated solid oxide comprises metal cations selected from a Group 1, 2, 12, or 13 metal.

Aspect 114. The process for preparing a catalyst composition, the process for forming an α,β-unsaturated carboxylic acid or a salt thereof, or the catalyst system according to any of the preceding Aspects where applicable, wherein [A] the metal-treated chemically-modified solid oxide or [B] the metal-treated solid oxide comprises an alkali metal cation, an alkaline earth metal cation, or any combination thereof.

Aspect 115. The process for preparing a catalyst composition, the process for forming an α,β-unsaturated carboxylic acid or a salt thereof, or the catalyst system according to any of the preceding Aspects where applicable, wherein [A] the metal-treated chemically-modified solid oxide or [B] the metal-treated solid oxide comprises cations selected from lithium, sodium, potassium, rubidium, cesium, magnesium, calcium, strontium, barium, copper, zinc, aluminum, or gallium cations.

Aspect 116. The process for preparing a catalyst composition, the process for forming an α,β-unsaturated carboxylic acid or a salt thereof, or the catalyst system according to any of the preceding Aspects where applicable, wherein [A] the metal-treated chemically-modified solid oxide or [B] the metal-treated solid oxide comprises any suitable Lewis acidic metal cation or any Lewis acidic metal cation disclosed herein.

Aspect 117. The process for preparing a catalyst composition, the process for forming an α,β-unsaturated carboxylic acid or a salt thereof, or the catalyst system according to any of the preceding Aspects where applicable, wherein [A] the metal-treated chemically-modified solid oxide or [B] the metal-treated solid oxide comprises sodium ions or potassium ions.

Aspect 118. The process for preparing a catalyst composition, the process for forming an α,β-unsaturated carboxylic acid or a salt thereof, or the catalyst system according to any of the preceding Aspects where applicable, wherein, independently, the metal-containing base comprises any suitable base or any base disclosed herein, e.g., carbonates (e.g., $Na_2CO_3$, $K_2CO_3$, $Cs_2CO_3$, $CaCO_3$, $MgCO_3$), hydroxides (e.g., NaOH, KOH, $Mg(OH)_2$), alkoxides (e.g., $Na(O^tBu)$, $K(O^tBu)$, $Mg(OEt)_2$, $Al(O^iPr)_3$), aryloxides which can be unsubstituted, hydrocarbyl-substituted, or halide-substituted (e.g. $Na(OC_6H_5)$, $K(OC_6H_5)$, $Na(O-2-C_6H_4F)$, $K(O-2-C_6H_4F)$, $Na(O-2-C_6H_4Cl)$, $K(O-2-C_6H_4Cl)$, $Na(O-4-C_6H_4F)$, $K(O-4-C_6H_4F)$, $Na(O-4-C_6H_4Cl)$, $K(O-4-C_6H_4Cl)$, $Na(O-2-C_6H_4Me)$, $K(O-2-C_6H_4Me)$, $Na(O-4-C_6H_4Me)$, $K(O-4-C_6H_4Me)$, $Na(O-2,6-C_6H_3Me_2)$, $K(O-2,6-C_6H_3Me_2)$, $Na(O-2,4,6-C_6H_2Me_3)$, $K(O-2,4,6-C_6H_2Me_3)$, $Na(O-2,6-C_6H_4-i-Pr_2)$, $K(O-2,6-C_6H_4-i-Pr_2)$, $Na(O-3,5-C_6H_3Me_2)$, $K(O-3,5-C_6H_3Me_2)$, sulfates (e.g. $Na_2SO_4$, $K_2SO_4$, $CaSO_4$, $MgSO_4$), and phosphates (e.g. $Na_3PO_4$, $K_3PO_4$), and the like.

Aspect 119. The process for preparing a catalyst composition, the process for forming an α,β-unsaturated carboxylic acid or a salt thereof, or the catalyst system according to any of the preceding Aspects where applicable, wherein [A] the metal-treated chemically-modified solid oxide or [B] the metal-treated solid oxide is prepared by contacting the chemically-modified solid oxide or the solid oxide, respectively, with $Na_2CO_3$, $Cs_2CO_3$, $MgCO_3$, $Mg(OH)_2$, NaOH, $Al(O^iPr)_3$, $Na(O^tBu)$, $Mg(OEt)_2$), and the like, or combinations thereof.

Aspect 120. The process for preparing a catalyst composition, the process for forming an α,β-unsaturated carboxylic acid or a salt thereof, or the catalyst system according to any of the preceding Aspects where applicable, wherein [A] the metal-treated chemically-modified solid oxide or [B] the metal-treated solid oxide is produced by a process comprising contacting any suitable chemically-modified solid oxide or any chemically-modified solid oxide disclosed herein, or any suitable solid oxide or any solid oxide disclosed herein, respectively, with any suitable metal-containing base or any metal-containing base disclosed herein to provide a mixture, and concurrently and/or subsequently drying and/or calcining the mixture.

Aspect 121. The process for preparing a catalyst composition, the process for forming an α,β-unsaturated carboxylic acid or a salt thereof, or the catalyst system according to any of the preceding Aspects where applicable, wherein the metal-treated solid oxide is generated by treatment of a silica, a silicate, or an aluminosilicate with (i) a metal-containing salt or (ii) a metal-containing base.

Aspect 122. The process for preparing a catalyst composition, the process for forming an α,β-unsaturated carboxylic acid or a salt thereof, or the catalyst system according to any of the preceding Aspects where applicable, wherein the metal-treated solid oxide is dried and calcined.

Aspect 123. The process for preparing a catalyst composition, the process for forming an α,β-unsaturated carboxylic acid or a salt thereof, or the catalyst system according to any of the preceding Aspects where applicable, wherein the metal-treated solid oxide is produced by a process comprising contacting any suitable solid oxide with any suitable metal-containing salt or any suitable metal-containing base to provide a mixture, and concurrently and/or subsequently drying and/or calcining the mixture.

Aspect 124. The process for preparing a catalyst composition, the process for forming an α,β-unsaturated carboxylic acid or a salt thereof, or the catalyst system according to any of the preceding Aspects where applicable, wherein the metal-treated solid oxide is generated by contacting any suitable silica, silicate, or aluminosilicate with any suitable metal-containing salt or any suitable metal-containing base to form a contact product, and concurrently and/or subsequently drying and/or calcining the contact product.

Aspect 125. The process for preparing a catalyst composition, the process for forming an α,β-unsaturated carboxylic acid or a salt thereof, or the catalyst system according to any of the preceding Aspects where applicable, wherein the metal-containing salt or the metal-containing base comprises a metal nitrate, carbonate, bicarbonate, sulfate, bisulfate, a phosphate, hydrogen phosphate salt, hydroxide, alkoxide, aryloxide, or amide, or alkylamide, or dialkylamide.

Aspect 126. The process for preparing a catalyst composition, the process for forming an α,β-unsaturated carboxylic acid or a salt thereof, or the catalyst system according to any of the preceding Aspects where applicable, wherein metal-treated solid oxide comprises a metal in a concentration of from 1 wt. % to 20 wt. %, from 2 wt. % to 15 wt. %, or from 3 wt. % to 10 wt. %, based on the total weight of the metal-treated solid oxide.

Aspect 127. The process for preparing a catalyst composition, the process for forming an α,β-unsaturated carboxylic acid or a salt thereof, or the catalyst system according to any of the preceding Aspects where applicable, wherein the metal-treated chemically-modified solid oxide or the metal-treated solid oxide is arranged as a fixed bed, a bubbling bed, a moving bed, or a stirred bed.

Aspect 128. The process for preparing a catalyst composition, the process for forming an α,β-unsaturated carboxylic acid or a salt thereof, or the catalyst system according to any of the preceding Aspects where applicable, wherein the diluent comprises any suitable non-protic solvent, or any non-protic solvent disclosed herein.

Aspect 129. The process for preparing a catalyst composition, the process for forming an α,β-unsaturated carboxylic acid or a salt thereof, or the catalyst system according to any of the preceding Aspects where applicable, wherein the diluent comprises any suitable weakly coordinating or non-coordinating solvent, or any weakly coordinating or non-coordinating solvent disclosed herein.

Aspect 130. The process for preparing a catalyst composition, the process for forming an α,β-unsaturated carboxylic acid or a salt thereof, or the catalyst system according to any of Aspects 1-129, wherein the diluent comprises any suitable aromatic hydrocarbon solvent, or any aromatic hydrocarbon solvent disclosed herein, e.g., benzene, xylene, toluene, etc.

Aspect 131. The process for preparing a catalyst composition, the process for forming an α,β-unsaturated carboxylic acid or a salt thereof, or the catalyst system according to any of Aspects 1-129, wherein the diluent comprises any suitable ether solvent, or any ether solvent disclosed herein, e.g., THF, dimethyl ether, diethyl ether, dibutyl ether, etc.

Aspect 132. The process for preparing a catalyst composition, the process for forming an α,β-unsaturated carboxylic acid or a salt thereof, or the catalyst system according to any of Aspects 1-129, wherein the diluent comprises any suitable carbonyl-containing solvent, or any carbonyl-containing solvent disclosed herein, e.g., ketones, esters, amides, etc. (e.g., acetone, ethyl acetate, N,N-dimethylformamide, etc.).

Aspect 133. The process for preparing a catalyst composition, the process for forming an α,β-unsaturated carboxylic acid or a salt thereof, or the catalyst system according to any of Aspects 1-129, wherein the diluent comprises any suitable halogenated aromatic hydrocarbon solvent, or any halogenated aromatic hydrocarbon solvent disclosed herein, e.g., chlorobenzene, dichlorobenzene, etc.

Aspect 134. The process for preparing a catalyst composition, the process for forming an α,β-unsaturated carboxylic acid or a salt thereof, or the catalyst system according to any of Aspects 1-129, wherein the diluent comprises THF, 2,5-$Me_2$THF, methanol, acetone, toluene, chlorobenzene, pyridine, or a combination thereof.

Aspect 135. The process for preparing a catalyst composition, the process for forming an α,β-unsaturated carboxylic acid or a salt thereof, or the catalyst system according to any of the preceding Aspects where applicable, wherein the diluent comprises or further comprises carbon dioxide.

Aspect 136. The process for preparing a catalyst composition, the process for forming an α,β-unsaturated carboxylic acid or a salt thereof, or the catalyst system according to any of the preceding Aspects where applicable, wherein the diluent comprises or further comprises the α,β-unsaturated carboxylic acid or the salt thereof.

Aspect 137. The process for preparing a catalyst composition, the process for forming an α,β-unsaturated carboxylic acid or a salt thereof, or the catalyst system according to any of the preceding Aspects where applicable, wherein the diluent further comprises the conjugate acid of the metal-containing base, e.g. HO$^t$Bu, HOEt, HO$^i$Pr, HOC$_6$H$_5$, HO-2-C$_6$H$_4$F, HO-2-C$_6$H$_4$Cl, HO-2-C$_6$H$_4$Me, HO-4-C$_6$H$_4$F, HO-4-C$_6$H$_4$Cl, HO-4-C$_6$H$_4$Me, HO-2,6-C$_6$H$_3$Me$_2$, HO-2,4,6-C$_6$H$_2$Me$_3$, HO-2,6-C$_6$H$_4$-i-Pr$_2$, HO-3,5-C$_6$H$_3$Me$_2$, [HCO$_3$]$^-$, H$_2$O, [HSO$_4$]$^-$, [HPO$_4$]$^{2-}$, [H$_2$PO$_4$]$^-$, and the like.

We claim:

1. A process for forming an α,β-unsaturated carboxylic acid or a salt thereof, the process comprising:
   (a) contacting in any order (i) a Group 8-11 transition metal precursor compound comprising at least one first ligand, (ii) optionally, at least one second ligand, (iii) a first olefin, (iv) carbon dioxide (CO$_2$), (v) a diluent, and (vi) [A] a metal-treated chemically-modified solid oxide, wherein the chemically-modified solid oxide comprises at least one solid oxide which has been treated with at least one electron-withdrawing anion, or [B] a metal-treated solid oxide, to provide a first reaction mixture,
   wherein the contacting is optionally carried out at a total pressure greater than ambient pressure, and
   wherein at least a portion of the Group 8-11 transition metal is deposited on the metal-treated chemically-modified solid oxide or the metal-treated solid oxide;
   (b) releasing the pressure from the first reaction mixture and removing the diluent from the first reaction mixture to provide the catalyst composition as a solid catalyst composition; and
   (c) contacting in any order (i) the solid catalyst composition, (ii) a second olefin, and (iii) carbon dioxide (CO$_2$) at a total pressure greater than ambient pressure to provide a second reaction mixture comprising an α,β-unsaturated carboxylic acid or a salt thereof.

2. The process for forming an α,β-unsaturated carboxylic acid or a salt thereof according to claim 1, wherein the first reaction mixture or the second reaction mixture, independently, comprises: a metalalactone; or an adduct of a metalalactone and the metal-treated chemically-modified solid oxide or the metal-treated solid oxide.

3. The process for forming an α,β-unsaturated carboxylic acid or a salt thereof according claim 1, further comprising the steps of:
(d) releasing at least a fraction of the total pressure from the second reaction mixture; and
(e) contacting in any order (i) the solid catalyst composition, (ii) the second olefin, and (iii) carbon dioxide ($CO_2$) at a total pressure greater than ambient pressure to provide a subsequent reaction mixture comprising an α,β-unsaturated carboxylic acid or a salt thereof.

4. The process for forming an α,β-unsaturated carboxylic acid or a salt thereof according to claim 3, further comprising the step of:
(f) repeating steps (d) and (e) any number of times to provide further subsequent reaction mixtures comprising the α,β-unsaturated carboxylic acid or a salt thereof.

5. The process for forming an α,β-unsaturated carboxylic acid or a salt thereof according to claim 1, wherein the first olefin and the second olefin independently are selected from ethylene, propylene, 1-butene, 1-pentene, 1-hexene, 1-heptene, 1-octene, or styrene.

6. The process for forming an α,β-unsaturated carboxylic acid or a salt thereof according to claim 1, wherein the first reaction mixture is pressurized with $CO_2$ to a $CO_2$ partial pressure greater than ambient pressure.

7. The process for forming an α,β-unsaturated carboxylic acid or a salt thereof according to claim 1, wherein the first olefin is ethylene and the first reaction mixture is pressurized with ethylene to an ethylene partial pressure greater than ambient pressure.

8. The process for forming an α,β-unsaturated carboxylic acid according to claim 1, wherein (a) the solid catalyst composition comprises less than 10 wt. % diluent, and/or (b) the solid catalyst composition comprises a free-flowing solid.

9. The process for forming an α,β-unsaturated carboxylic acid or a salt thereof according to claim 1, wherein the step of contacting the solid catalyst composition, the second olefin, and carbon dioxide ($CO_2$) is carried out in the substantial absence of a diluent.

10. The process for forming an α,β-unsaturated carboxylic acid or a salt thereof according to claim 1, wherein the step of contacting the solid catalyst composition, the second olefin, and carbon dioxide ($CO_2$) is carried out in the presence of a diluent.

11. The process for forming an α,β-unsaturated carboxylic acid or a salt thereof according to claim 1, wherein the metal of the Group 8-11 transition metal precursor compound is a Group 8 metal.

12. The process for forming an α,β-unsaturated carboxylic acid or a salt thereof according to claim 1, wherein the metal of the Group 8-11 transition metal precursor compound is a Group 9 metal.

13. The process for forming an α,β-unsaturated carboxylic acid or a salt thereof according to claim 1, wherein the metal of the Group 8-11 transition metal precursor compound is a Group 10 metal.

14. The process for forming an α,β-unsaturated carboxylic acid or a salt thereof according to claim 1, wherein the first ligand and the second ligand, independently, are selected from a diphosphine ligand, a diamine ligand, a diene ligand, a diether ligand, or dithioether ligand.

15. The process for forming an α,β-unsaturated carboxylic acid or a salt thereof according to claim 1, wherein the first ligand and the second ligand, independently, is selected from trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, tricyclohexylphosphine, trimethyl phosphite, triethyl phosphite, tripropyl phosphite, triisopropyl phosphite, tributyl phosphite and tricyclohexyl phosphite, 2-(di-t-butylphosphino) biphenyl, 2-di-t-butylphosphino-1,1'-binaphthyl, 2-(di-t-butylphosphino)-3,6-dimethoxy-2',4',6'-tri-i-propyl-1,1'-biphenyl, 2-di-t-butylphosphino-2'-methylbiphenyl, 2-(di-t-butylphosphinomethyl) pyridine, 2-di-t-butylphosphino-2',4',6'-tri-i-propyl-1,1'-biphenyl, 2-(dicyclohexylphosphino) biphenyl, (S)-(+)-(3,5-dioxa-4-phospha-cyclohepta [2,1-a;3,4-a'] dinaphthalen-4-yl) dimethylamine, 2-(diphenylphosphino)-2'-methoxy-1,1'-binaphthyl, 1,2,3,4,5-pentaphenyl-1'-(di-t-butylphosphino) ferrocene, 2,2'-bis (diphenylphosphino)-1,1'-binaphthyl (BINAP), 1,2-bis (dimethylphosphino) ethane, 1,2-bis (diethylphosphino) ethane, 1,2-bis (dipropylphosphino)-ethane, 1,2-bis (diisopropylphosphino) ethane, 1,2-bis (di-n-butylphosphino) ethane, 1,2-bis (di-t-butyl-phosphino) ethane, 1,2-bis (dicyclohexylphosphino) ethane, 1,3-bis (dicyclohexylphosphino) propane, 1,4-bis (dicyclohexylphosphino) butane, 1,3-bis (diisopropylphosphino) propane, 1,3-bis (diphenylphosphino) propane, 1,3-bis (di-t-butylphosphino) propane, 1,4-bis (diisopropylphosphino) butane, 1,4-bis (diphenylphosphino) butane, 2,2'-bis [bis (3,5-dimethylphenyl) phosphino]-4,4',6,6'-tetramethoxybiphenyl, 2,6-bis (di-t-butylphosphinomethyl) pyridine, 2,2'-bis (dicyclohexylphosphino)-1,1'-biphenyl, bis (2-dicyclohexylphosphinophenyl) ether, 5,5'-bis (diphenylphosphino)-4,4'-bi-1,3-benzodioxole, 2-t-butylphosphinomethylpyridine, bis (diphenylphosphino) ferrocene, bis (diphenylphosphino) methane, bis (dicyclohexylphosphino) methane, bis (di-t-butylphosphino) methane, TMEDA, 2,2'-bipyridine, or 2-((di-t-butylphosphino) methyl) pyridine.

16. The process for forming an α,β-unsaturated carboxylic acid or a salt thereof according to claim 1, wherein the first ligand and the second ligand, independently, is selected from:
(1R,1'R,2S,2'S)-2,2'-Di-tert-butyl-2,3,2',3'-tetrahydro-1H,1'H-(1,1') biisophosphindolyl (also designated (1R,1'R,2S,2'S)-DuanPhos);
(3S,3'S,4S,4'S,11bS,11'bS)-(+)-4,4'-Di-t-butyl-4,4',5,5'-tetrahydro-3,3'-bi-3H-dinaphtho [2,1-c: 1',2'-e] phosphepin (also designated(S)-BINAPINE);
(1S,1S',2R,2R')-1,1'-Di-tert-butyl-(2,2')-diphospholane (also designated (S,S',R,R')-TangPhos);
(−)-1,2-Bis [(2S,5S)-2,5-diisopropylpholano] benzene (also designated (S,S)-i-Pr-DUPHOS);
(+)-1,2-Bis [(2R,5R)-2,5-diisopropylpholano] benzene (also designated (R,R)-i-Pr-DUPHOS);
a racemic mixture of (S,S)-i-Pr-DUPHOS and (R,R)-i-Pr-DUPHOS);
(−)-1,2-Bis [(2S,5S)-2,5-dimethylpholano] benzene (also designated (S,S)-Me-DUPHOS);
(+)-1,2-Bis [(2R,5R)-2,5-dimethylpholano] benzene (also designated (R,R)-Me-DUPHOS);
a racemic mixture of (S,S)-Me-DUPHOS) and (R,R)-Me-DUPHOS;
(R,R)-(−)-2,3-Bis (tert-butylmethylphosphino) quinoxaline (also designated (R)-QuinoxP); or (R,R)-(+)-1,2-Bis (t-butylmethylphosphino) benzene (also designated (R,R)-BenzP*).

17. The process for forming an α,β-unsaturated carboxylic acid or a salt thereof according to claim 1, wherein the solid oxide of [A] the metal-treated chemically-modified solid oxide or [B] the metal-treated solid oxide is selected from $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, $Na_2O$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, $K_2O$, CaO, $La_2O_3$, $Ce_2O_3$, mixtures thereof, mixed oxides thereof, and any combinations thereof.

18. The process for forming an α,β-unsaturated carboxylic acid or a salt thereof according to claim 1, wherein the solid oxide of [A] the metal-treated chemically-modified solid oxide or [B] the metal-treated solid oxide is selected from silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, heteropolytungstate, a silicate, an aluminosilicate, or any combination thereof.

19. The process for forming an α,β-unsaturated carboxylic acid or a salt thereof according to claim 1, wherein the solid oxide of [A] the metal-treated chemically-modified solid oxide or [B] the metal-treated solid oxide is selected from a mesoporous silica, a mesostructured cellular foam (MCF) silica, a molecular sieve, a zeolite, or any combination thereof.

20. The process for forming an α,β-unsaturated carboxylic acid or a salt thereof according to claim 1, wherein the electron-withdrawing anion comprises is selected from the group consisting of sulfate, bisulfate, fluorosulfate, phosphate, fluorophosphate, triflate, mesylate, tosylate, thiosulfate, $C_1$-$C_{10}$ alkyl sulfonate, $C_6$-$C_{14}$ aryl sulfonate, fluoride, chloride, and any combination thereof.

21. The process for forming an α,β-unsaturated carboxylic acid or a salt thereof according to claim 1, wherein the chemically-modified solid oxide is generated by treatment of a solid oxide with sulfuric acid, sulfate ion, bisulfate ion, fluorosulfuric acid, fluorosulfate ion, phosphoric acid, phosphate ion, fluorophosphoric acid, monofluorophosphate ion, triflic (trifluoromethanesulfonic) acid, triflate trifluoromethanesulfonate) ion, methanesulfonic acid, mesylate (methanesulfonate) ion, toluenesulfonic acid, tosylate (toluenesulfonate) ion, thiosulfate ion, $C_1$-$C_{10}$ alkyl sulfonic acid, $C_1$-$C_{10}$ alkyl sulfonate ion, $C_6$-$C_{14}$ aryl sulfonic acid, $C_6$-$C_{14}$ aryl sulfonate ion, fluoride ion, chloride ion, or any combination thereof.

22. The process for forming an α,β-unsaturated carboxylic acid or a salt thereof according to claim 1, wherein the chemically-modified solid oxide comprises a solid oxide that is chemically-modified with an electron-withdrawing anion, wherein:

the solid oxide is selected from the group consisting of silica, alumina, silica-alumina, silica-coated alumina, aluminum phosphate, aluminophosphate, heteropolytungstate, titania, zirconia, magnesia, boria, zinc oxide, a mixed oxide thereof, and any mixture thereof; and the electron-withdrawing anion is selected from the group consisting of sulfate, bisulfate, fluorosulfate, phosphate, fluorophosphates, fluoride, and chloride.

23. The process for forming an α,β-unsaturated carboxylic acid or a salt thereof according to claim 1, wherein the metal-treated solid oxide is selected from the group consisting of Na-MCM-41, Na/Al-KIT-6, Na—Y zeolite, Na-SBA-15, Na-treated trimodal porous silica (TMS), potassium L-zeolite, and any combination thereof.

24. The process for forming an α,β-unsaturated carboxylic acid or a salt thereof according to claim 1, wherein [A] the metal-treated chemically-modified solid oxide or [B] the metal-treated solid oxide is prepared by contacting the chemically-modified solid oxide or the solid oxide, respectively, with (a) a metal-containing base, (b) a metal-containing salt in combination with a non-metal containing base, or (c) a metal-containing salt.

25. The process for forming an α,β-unsaturated carboxylic acid or a salt thereof according to claim 24, wherein the metal-containing base comprises is selected from the group consisting of: a metal carbonate; a metal hydroxide; a metal alkoxide; an unsubstituted, hydrocarbyl-substituted, or halide-substituted aryloxide; a sulfate; and a phosphate.

26. The process for forming an α,β-unsaturated carboxylic acid or a salt thereof according to claim 1, wherein [A] the metal-treated chemically-modified solid oxide or [B] the metal-treated solid oxide comprises metal cations selected from a Group 1, 2, 12, or 13 metal.

27. The process for forming an α,β-unsaturated carboxylic acid or a salt thereof according to claim 1, wherein [A] the metal-treated chemically-modified solid oxide or [B] the metal-treated solid oxide is calcining.

28. The process for forming an α,β-unsaturated carboxylic acid or a salt thereof according to claim 1, the metal-treated chemically-modified solid oxide or the metal-treated solid oxide is arranged as a fixed bed, a bubbling bed, a moving bed, or a stirred bed.

29. The process for forming an α,β-unsaturated carboxylic acid or a salt thereof according to claim 1, wherein the diluent is selected from a non-protic solvent.

30. The process for forming an α,β-unsaturated carboxylic acid or a salt thereof according to claim 1, wherein the diluent is selected from the group consisting of an aromatic hydrocarbon solvent, a halogenated aromatic hydrocarbon, an ether solvent, a carbonyl-containing solvent, and an alcohol solvent.

\* \* \* \* \*